(12) United States Patent
Lou et al.

(10) Patent No.: US 11,572,360 B2
(45) Date of Patent: Feb. 7, 2023

(54) SUBSTITUTED 4-AMINO-1H-IMIDAZO[4,5-C]QUINOLINE COMPOUNDS AND IMPROVED METHODS FOR THEIR PREPARATION

(71) Applicant: INNATE TUMOR IMMUNITY, INC, Princeton, NJ (US)

(72) Inventors: Sha Lou, North Brunswick, NJ (US); Adrian Ortiz, Oak Park, CA (US); Christopher Robert Jamison, Hillsborough, NJ (US); Victor W. Rosso, Monroe Township, NJ (US); Mansi S. Shah, Highland Park, NJ (US)

(73) Assignee: INNATE TUMOR IMMUNITY, INC., Princeton, NJ (US)

( * ) Notice: Subject to any disclaimer, the term of this patent is extended or adjusted under 35 U.S.C. 154(b) by 0 days.

(21) Appl. No.: 17/268,725

(22) PCT Filed: Aug. 15, 2019

(86) PCT No.: PCT/US2019/046594
§ 371 (c)(1),
(2) Date: Feb. 16, 2021

(87) PCT Pub. No.: WO2020/037094
PCT Pub. Date: Feb. 20, 2020

(65) Prior Publication Data
US 2021/0332040 A1    Oct. 28, 2021

Related U.S. Application Data

(60) Provisional application No. 62/720,970, filed on Aug. 22, 2018, provisional application No. 62/765,094, filed on Aug. 16, 2018.

(51) Int. Cl.
| | | |
|---|---|---|
| C07D 471/04 | (2006.01) | |
| C07D 233/64 | (2006.01) | |
| C07D 233/68 | (2006.01) | |
| C07D 233/90 | (2006.01) | |
| C07D 405/04 | (2006.01) | |

(52) U.S. Cl.
CPC ......... *C07D 471/04* (2013.01); *C07D 233/64* (2013.01); *C07D 233/68* (2013.01); *C07D 233/90* (2013.01); *C07D 405/04* (2013.01)

(58) Field of Classification Search
CPC .................................................. C07D 471/04
See application file for complete search history.

(56) References Cited

U.S. PATENT DOCUMENTS

| | | |
|---|---|---|
| 10,533,005 B2 | 1/2020 | Glick et al. |
| 10,533,007 B2 | 1/2020 | Glick et al. |
| 10,556,903 B2 | 2/2020 | Glick et al. |
| 2010/0183509 A1 | 7/2010 | Babich et al. |
| 2014/0249135 A1 | 9/2014 | Burger et al. |
| 2015/0299194 A1 | 10/2015 | Hoves et al. |
| 2020/0157096 A1 | 5/2020 | Glick et al. |
| 2020/0157097 A1 | 5/2020 | Glick et al. |

FOREIGN PATENT DOCUMENTS

| | | |
|---|---|---|
| WO | 199302057 A1 | 2/1993 |
| WO | 2006009832 A1 | 1/2006 |
| WO | 2008076805 A2 | 6/2008 |
| WO | 2010065899 A2 | 6/2010 |
| WO | 2011150243 A1 | 12/2011 |
| WO | 2012/080762 A1 | 6/2012 |
| WO | 2012148140 A2 | 11/2012 |
| WO | 2015/069310 A1 | 5/2015 |
| WO | 2016008010 A1 | 1/2016 |
| WO | 2016081290 A1 | 5/2016 |
| WO | 2017102091 A1 | 6/2017 |
| WO | 2017160922 A1 | 9/2017 |
| WO | 2017184735 A1 | 10/2017 |
| WO | 2017184746 A1 | 10/2017 |
| WO | 2018152396 A1 | 8/2018 |
| WO | 2019090088 A1 | 5/2019 |

OTHER PUBLICATIONS

CAS Registry No. 1176515-13-1; STN Entry Date Aug. 27, 2009; Benzenamine, 2-bromo-5-(5-thiazolyl)-[1].
CAS Registry No. 1553656-80-6; STN Entry Date Feb. 24, 2014; Thiazole, 4-(4-fluoro-3-nitrophenyl)-[1].
CAS Registry No. 2138084-49-6; STN Entry Date Nov. 2, 2017; Benzenamine, 2,3-difluoro-5-(1H-pyrazol-4-yl)-[1].
CAS Registry No. 2138207-17-5; STN Entry Date Nov. 2, 2017; Benzenamine, 2,6-difluoro-3-(5-thiazolyl)-[1].
CAS Registry No. 2224484-23-3; STN Entry Date May 21, 2018; Acetamide, 2-propoxy-N-[[5-(trifluoromethyl)-1H-imidazol-2-yl]methyl]-[1].
Stankova, et al., "Synthesis of Thiazole, Imidazole and Oxazole Containing Amino Acids for Peptide Backbone Modification", Journal of Peptide Science, vol. 5, pp. 392-398 (1999).
U.S. Appl. No. 17/049,612, filed Oct. 22, 2020, Zhang et al.
U.S. Appl. No. 17/267,513, filed Feb. 10, 2021, Zhang et al.
U.S. Appl. No. 17/267,516, filed Feb. 10, 2021, Zhang et al.
Shi, et al., Bisubstrate Inhibitors of Biotin Protein Ligase in *Mycobacterium tuberculosis* Resistant to Cyclonucleoside Formation, ACS Medicinal Chemistry Letters, vol. 4(12), 1213-1217 (2013).

*Primary Examiner* — Shawquia Jackson
(74) *Attorney, Agent, or Firm* — Jing G. Sun

(57) ABSTRACT

Improved methods and intermediates thereof for preparing substituted 4-amino-1H-imidazo[4,5-c]quinoline compounds are described. These compounds are useful as NLRP3 modulators.

2 Claims, 5 Drawing Sheets

Form A PXRD

Form B PXRD

SUBSTITUTED 4-AMINO-1H-IMIDAZO[4,5-C]QUINOLINE COMPOUNDS AND IMPROVED METHODS FOR THEIR PREPARATION

CROSS-REFERENCE TO RELATED APPLICATIONS

This application is a 371 of International Application No. PCT/US2019/046594 filed on Aug. 15, 2019, which claims the priority benefit of U.S. Provisional Application 62/765,094 filed Aug. 16, 2018 and 62/720,970 filed Aug. 22, 2018; each of which is incorporated herein by reference in its entirety.

TECHNICAL FIELD

The present invention relates to improved methods for preparing substituted 4-amino-1H-imidazo[4,5-c]quinoline compounds. The present invention also relates to solid forms of N-[[4-amino-7-(1H-pyrazol-3-yl)-1H-imidazo[4,5-c]quinolin-2-yl]methyl]-N-ethylacetamide, their salts and hydrates, processes for their production, pharmaceutical compositions comprising them, and methods of treatment using them.

BACKGROUND

Nucleotide-binding oligomerization domain-like receptors ("NLRs") include a family of intracellular receptors that detect pathogen-associated molecular patterns ("PAMPs") and endogenous molecules (see, e.g., Ting, J. P. Y. et al., "The NLR gene family a standard nomenclature," *Immunity*, 28(3):285-287, (2008)).

NLRPs represent a subfamily of NLRB that include a Pyrin domain and are constituted by proteins such as NLRP1, NLRP3, NLRP4, NLRP6, NLRP7, and NLRP12. NLRPs are believed to be involved with the formation of multiprotein complexes termed inflammasomes (see, e.g., Chaput, C. et al., "NOD-like receptors in lung diseases," *Frontiers in Immunology*, 4: article 393, (2013)). These complexes typically include one or two NLR proteins, the adapter molecule apoptosis associated speck-like containing a CARD domain (ASC) and pro-caspase-1 F (see, e.g., Bauernfeind, F and Hornung, V. "Of inflammasomes and pathogens—sensing of microbes by the inflammasome," *EMBO Molecular Medicine*, 5(6):814-826, (2013)).

One such inflammasome is formed by the NLRP3 scaffold, the ASC adaptor and pro-caspase-1 (see, e.g., Hirota, J. A., et al., "The airway epithelium nucleotide-binding domain and leucine-rich repeat protein 3 inflammasome is activated by urban particulate matter," *Journal of Allergy and Clinical Immunology*, 129(4):1116.e6-1125.e6, (2012)), and its expression is believed to be induced by inflammatory cytokines and TLR agonists in myeloid cells and human bronchial epithelial cells (Id.). The NLRP3 inflammasome is believed to mediate the caspase-1-dependent conversion of pro-IL-1β and pro-IL-18 to IL-1β and IL-18. Further, IL-1β and IL-18 have potential in the treatment of various types of cancer (see, e.g., Chen, L-C. et al., *EMBO Mol Med.*, 4(12):1276-1293 (2012) and Tse, B. W-C. et al., *PLoS One*, 6(9):e24241 (2011)). IL-18 has been shown to override resistance to checkpoint inhibitors in colon cancer animal tumor models (see e.g., Ma, Z. et al., *Clin. Cancer Res. Jan.* 11. (2016) DOI: 10.1158/1078-0432.CCR-15-1655).

Substituted 4-amino-JH-imidazo[4,5-c]quinoline NLRP3 modulators (e.g., agonists or partial agonists) that are useful for the treatment of cancer have been described. See, e.g., WO2017/184746 and WO2018/152396. Improved methods of making substituted 4-amino-1H-imidazo[4,5-c]quinoline compounds, which provide practical, large-scale synthesis, and improved production quality, efficiency and safety, are needed.

SUMMARY

The present invention provides novel processes, and novel intermediates thereof, for making substituted 4-amino-1H-imidazo[4,5-c]quinoline compounds.

The invention provides methods of making a compound of Formula (I), or a tautomer, a stereoisomer or a salt thereof:

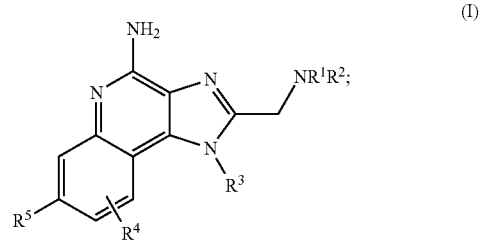

wherein $R^1$, $R^2$, $R^3$, $R^4$, and $R^5$ can be as defined below;
comprising (1) contacting a compound of Formula (II), or a tautomer, a stereoisomer, or a salt thereof:

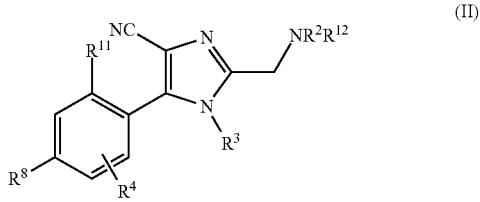

wherein $R^2$, $R^3$, $R^4$, $R^8$, $R^{11}$ and $R^{12}$ can be as defined below;
with a mixture of an acid, with or without a base, in a suitable organic solvent or organic solvent mixture;
for a time and at a temperature sufficient for cyclization and to produce a compound of Formula (III), or a tautomer, a stereoisomer, or a salt thereof:

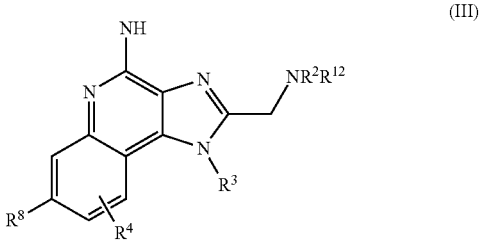

wherein $R^2$, $R^3$, $R^4$, $R^8$, and $R^{12}$ can be as defined below;
and (2) contacting the compound of Formula (III), or a tautomer, a stereoisomer, or a salt thereof, with a suitable acid, in a suitable aqueous solvent, for a time and at a temperature sufficient for hydrolysis and de-protection and to produce the compound of Formula (I), or a tautomer, a stereoisomer, or a salt thereof.

The invention provides methods of making a compound of Formula (II), or a tautomer, a stereoisomer or a salt thereof:

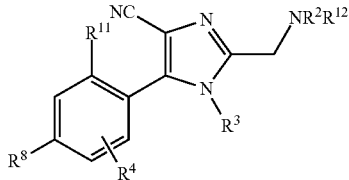
(II)

comprising contacting a compound of Formula (IV), or a tautomer, a stereoisomer, or a salt thereof:

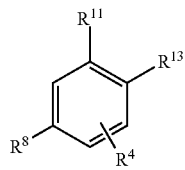
(IV)

wherein $R^4$, $R^8$, $R^{11}$ and $R^{13}$ can be as defined below;
with a compound of Formula (V), or a tautomer, a stereoisomer, or a salt thereof:

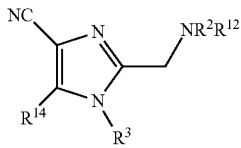
(V)

wherein $R^2$, $R^3$, $R^{12}$, and $R^{14}$ can be as defined below;
and with a mixture of a transition metal catalyst and a base in a suitable organic solvent or organic solvents mixture;
for a time and at a temperature sufficient for coupling and to produce a compound of Formula (II), or a tautomer, a stereoisomer, or a salt thereof.

Also described are methods of making intermediate compounds, such as compounds of Formula (II), (III), (IV) and (V), and stereoisomers thereof.

The disclosure also relates to solid forms of N-[[4-amino-7-(1H-pyrazol-3-yl)-1H-imidazo[4,5-c]quinolin-2-yl]methyl]-N-ethylacetamide (Compound 1) including solid forms of N-[[4-amino-7-(1H-pyrazol-3-yl)-1H-imidazo[4,5-c]quinolin-2-yl]methyl]-N-ethylacetamide free base monohydrate and in dehydrated state. Compositions comprising the described solid forms, as well as methods of preparing and using them in therapy, are also described.

DETAILED DESCRIPTION

Figure 1:
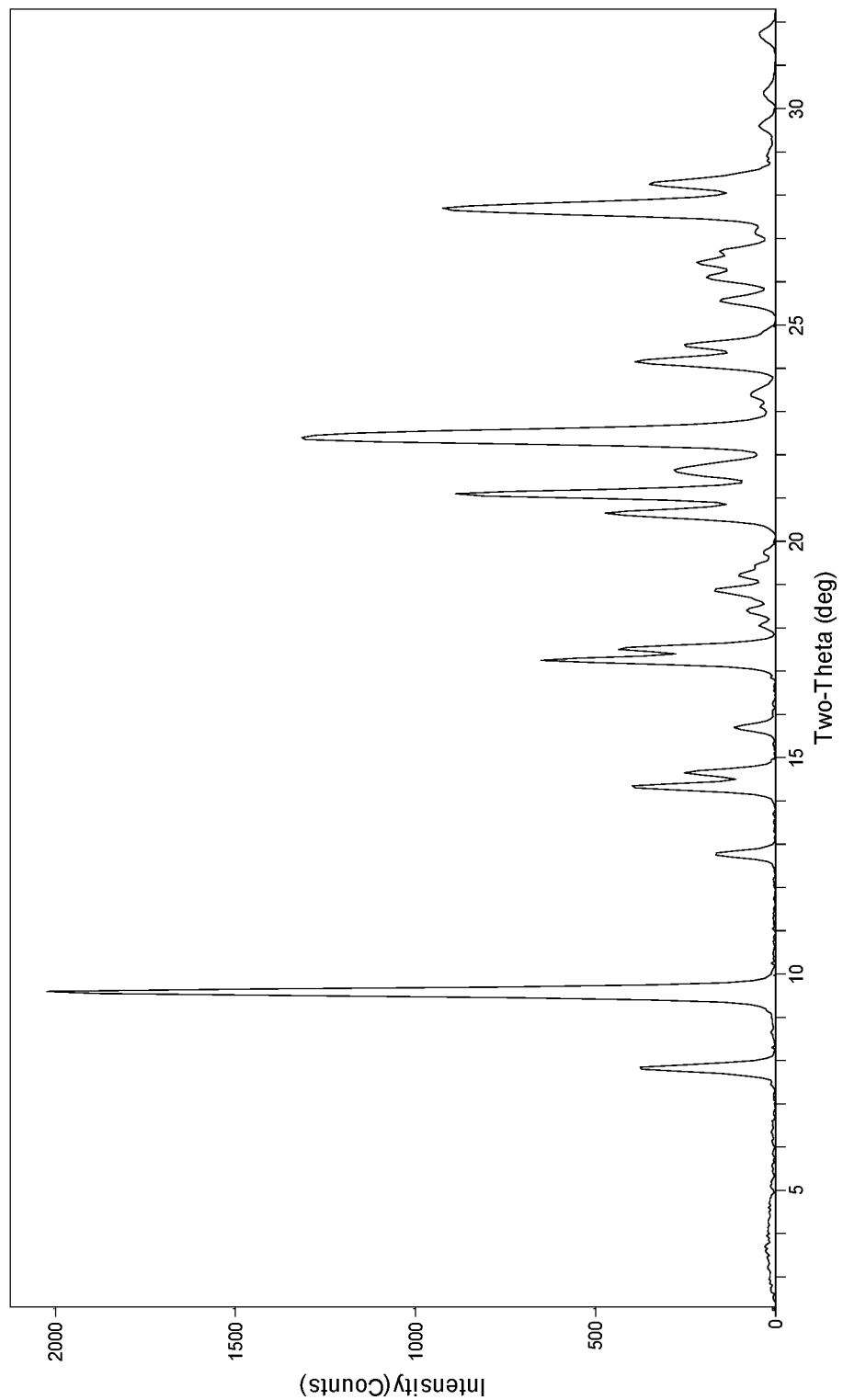
FIG. 1 depicts a powder X-ray diffraction pattern (CuKα at room temperature) of Form A of Compound 1.

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s). Such compounds are clearly contemplated within the scope of this disclosure, though such resonance forms or tautomers are not explicitly represented herein.

In a 1st aspect, the invention provides a method of making a compound of Formula (I), or a tautomer, a stereoisomer or a salt thereof:

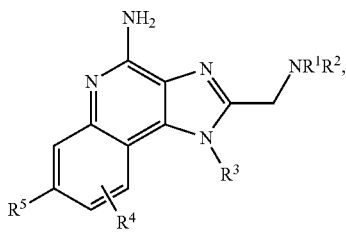
(I)

wherein:
$R^1$ is independently H, $C_{1-6}$ alkyl, $C(O)R^a$, $—C(O)OR^a$, $—S(O)_{1-2}(R^b)$, $—S(O)_{1-2}NR^cR^d$, or $—C(O)NR^cR^d$;
$R^2$ is independently H or $C_{1-6}$ alkyl;
$R^3$ is independently:
(i) H;
(ii) $C_{1-6}$ haloalkyl;
(iii) $C_{1-8}$ alkyl optionally substituted with $R^6$, wherein $R^6$ is —OH, $C_{1-4}$ alkoxy, $—(CH_2)^{1-4}O(CH)(CH_2)_{1-4}(C_{1-4}$ alkoxy), $C_{1-4}$ haloalkoxy, $CO_2R^a$, or $—CONR^cR^d$; or
(vi) $(C_{0-3}$ alkylene)-$R^7$, wherein $R^7$ is $C_{3-6}$ cycloalkyl, phenyl, 5- to 6-membered heterocycloalkyl containing from 1 to 4 ring atoms are each independently selected from N, $N(R^e)$, O, and S, or 5- to 6-membered heteroaryl containing from 1 to 4 ring atoms are each independently selected from N, $N(R^e)$, O, and S; and $R^7$ is optionally substituted with halogen, $C_{1-6}$ alkyl, $C_{1-4}$ haloalkyl, $C_{1-4}$ alkoxy, or $C_{1-4}$ haloalkoxy;
$R^4$ is independently H, halogen, cyano, OH, $C_{1-4}$ alkoxy, $C_{1-4}$ haloalkyl, $C_{1-4}$ haloalkoxy, $—C(O)OH$, $—C(O)OR^a$, $—NR^cR^d$, $—C(O)NR^cR^d$, $—S(O)_{1-2}(R^b)$, or $C_{1-4}$ alkyl substituted with from 0 to 2 $R^h$;
$R^5$ is independently halo or $—(C_{0-3}$ alkylene)-(5-membered heteroaryl) wherein the heteroaryl includes 1 to 4 ring carbon atoms and 1 to 4 ring heteroatoms are each independently selected from: N, $N(R^e)$, O, and S, and is substituted with from 0 to 3 $R^g$;

$R^a$ is, at each occurrence, independently:
(i) $C_{1-6}$ alkyl optionally substituted with from 1 to 2 $R^h$;
(ii) $C_{1-6}$ haloalkyl;
(iii) —($C_{0-3}$ alkylene)-$C_{3-6}$ cycloalkyl, wherein the cycloalkyl is optionally substituted with from 1 to 2 $R^f$;
(iv) —($C_{0-3}$ alkylene)-heterocyclyl including from 3 to 8 ring atoms, wherein from 1 to 3 ring atoms are each independently selected from $N(R^e)$, O, and S, wherein the heterocyclyl is optionally substituted with from 1 to 4 independently selected $R^f$;
(v) —($C_{0-3}$ alkylene)-phenyl optionally substituted with from 1 to 4 independently selected $R^g$; or
(vi) —($C_{0-3}$ alkylene)-heteroaryl including from 5 to 6 ring atoms, wherein from 1 to 4 ring atoms are each independently selected from N, $N(R^e)$, O, and S, wherein the heteroaryl is optionally substituted with from 1 to 3 independently selected $R^g$;

$R^b$ is $C_{1-6}$ alkyl;
each occurrence of $R^c$ and $R^d$ is independently H or $C_{1-4}$ alkyl;
each occurrence of $R^e$ is independently H or $C_{1-4}$ alkyl;
each occurrence of $R^f$ is independently $C_{1-6}$ alkyl, $C_{1-4}$ haloalkyl, OH, F, Cl, $C_{1-4}$ alkoxy, $C_{1-4}$ haloalkoxy, cyano, or phenyl optionally substituted with from 1 to 4 $R^g$;
each occurrence of $R^g$ is independently halogen, cyano, $C_{1-6}$ alkyl, $C_{1-4}$ haloalkyl, $C_{1-4}$ alkoxy, or $C_{1-4}$ haloalkoxy; and
each occurrence of $R^h$ is independently OH, F, Cl, $C_{1-4}$ alkoxy, $C_{1-4}$ haloalkoxy, or cyano;

comprising (1) contacting a compound of Formula (II), or a tautomer, a stereoisomer, or a salt thereof:

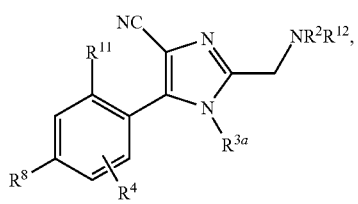
(II)

wherein $R^2$ and $R^4$ are as defined as above for Formula (I);
$R^{3a}$ is independently $R^3$, $C(O)R^a$, —$C(O)OR^a$, —$S(O)_{1-2}(R^b)$,

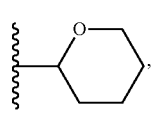, 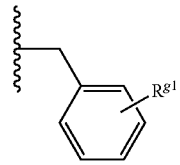

or

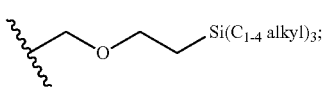

$R^8$ is independently halo or —($C_{0-3}$ alkylene)-(5-membered heteroaryl) wherein the heteroaryl includes 1 to 4 ring carbon atoms and 1 to 4 ring heteroatoms are each independently selected from: N, $N(R^{e1})$, O, and S, and is substituted with from 0 to 3 $R^g$;

$R^{11}$ is independently $NH_2$ or $NO_2$;
$R^{12}$ is independently H, $C_{1-6}$ alkyl, triphenylmethyl, $C(O)R^a$, —$C(O)OR^a$, —$S(O)_{1-2}(R^b)$, —$S(O)_{1-2}NR^cR^d$, —$C(O)NR^cR^d$, or

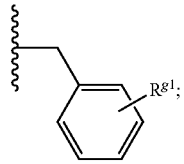

$R^{e1}$ is independently H, $C(O)R^a$, —$C(O)OR^a$, —$S(O)_{1-2}(R^h)$,

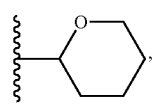, 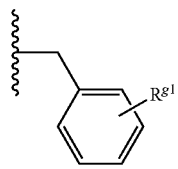

or;

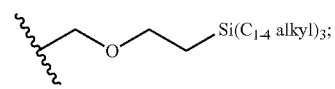

and
$R^{g1}$ is independently H, halo, cyano, $C_{1-6}$ alkyl, $C_{1-4}$ haloalkyl, $C_{1-4}$ alkoxy, or $C_{1-4}$ haloalkoxy;

with a mixture of Reagent 1 selected from a Brønsted acid, a Lewis acid, and a transition metal catalyst or a combination thereof, with or without Base 1 selected from a Brønsted base and a Lewis base, with or without an additive, in Solvent 1 that is a protic, aprotic or polar organic solvent or organic solvent mixture;
for a time and at a temperature sufficient for cyclization and to produce a compound of Formula (III), or a tautomer, a stereoisomer, or a salt thereof:

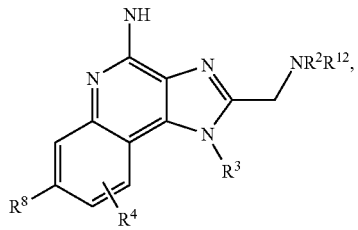
(III)

wherein $R^2$, $R^3$, and $R^4$ are as defined as above for Formula (I), and $R^8$, and $R^{12}$ are as defined as above for Formula (II);
and (2) contacting the compound of Formula (III), or a tautomer, a stereoisomer, or a salt thereof, with Reagent 2 selected from a Brønsted acid, a Lewis acid, a Brønsted base, and a Lewis base, in Solvent 2 that is a protic, aprotic or polar solvent or solvent mixture, for a time and at a temperature sufficient for hydrolysis and/or de-protection and to produce the compound of Formula (I), or a tautomer, a stereoisomer, or a salt thereof.

In another aspect, the invention provides a method of making a compound of Formula (I) as defined in the 1st aspect, or a tautomer, a stereoisomer or a salt thereof;

comprising (1) contacting a compound of Formula (II) as defined in the 1st aspect, or a tautomer, a stereoisomer, or a salt thereof, with a mixture of Reagent 1 selected from a Brønsted acid, a Lewis acid, and a transition metal catalyst or a combination thereof, with or without Base 1 selected from a Brønsted base and a Lewis base, in Solvent 1 that is a protic, aprotic or polar organic solvent or organic solvent mixture;

for a time and at a temperature sufficient for cyclization and to produce a compound of Formula (III) as defined in the 1st aspect, or a tautomer, a stereoisomer, or a salt thereof;

and (2) contacting the compound of Formula (III), or a tautomer, a stereoisomer, or a salt thereof, with Reagent 2 selected from a Brønsted acid, a Lewis acid, a Brønsted base, and a Lewis base, in Solvent 2 that is a protic, aprotic or polar solvent or solvent mixture, for a time and at a temperature sufficient for hydrolysis and/or de-protection and to produce the compound of Formula (I), or a tautomer, a stereoisomer, or a salt thereof.

In a 2nd aspect, within the scope of the 1st aspect, the invention provides a method of making a compound of Formula (I), or a tautomer, a stereoisomer or a salt thereof:

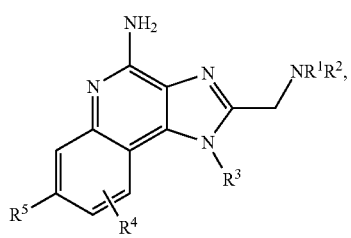
(I)

wherein:

$R^3$ is independently H, $C_{1-6}$ haloalkyl, or $C_{1-8}$ alkyl optionally substituted with $R^6$, wherein $R^6$ is OH, $C_{1-4}$ alkoxy, $C_{1-4}$ haloalkoxy, $CO_2R^a$, or $-CONR^cR^d$;

$R^4$ is independently H, halogen, cyano, OH, $C_{1-4}$ alkyl, $C_{1-4}$ alkoxy, $C_{1-4}$ haloalkyl, or $C_{1-4}$ haloalkoxy;

$R^5$ is independently 5-membered heteroaryl wherein the heteroaryl includes 1 to 4 ring carbon atoms and 1 to 4 ring heteroatoms are each independently selected from: N, $N(R^e)$, O, and S, and is substituted with from 0 to 3 $R^g$;

$R^a$ is, at each occurrence, independently:
(i) $C_{1-6}$ alkyl optionally substituted with from 1 to 2 $R^h$;
(ii) $CF_3$;
(iii) $C_{3-6}$ cycloalkyl optionally substituted with from 1 to 2 $R^f$;
(vi) heterocyclyl including from 5 to 7 ring atoms, wherein from 1 to 3 ring atoms are each independently selected from $N(R^e)$, O, and S, wherein the heterocyclyl is optionally substituted with from 1 to 4 independently selected $R^f$;
(v) phenyl optionally substituted with from 1 to 4 independently selected $R^g$; or
(vi) heteroaryl including from 5 to 6 ring atoms, wherein from 1 to 4 ring atoms are each independently selected from N, $N(R^e)$, O, and S, wherein the heteroaryl is optionally substituted with from 1 to 3 independently selected $R^g$;

comprising (1) contacting a compound of Formula (II), or a tautomer, a stereoisomer, or a salt thereof:

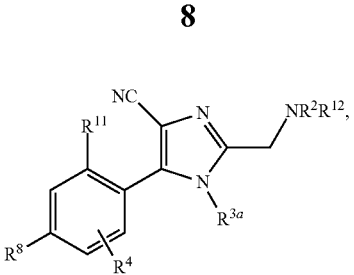
(II)

wherein: $R^2$ and $R^4$ are as defined as above for Formula (I);

$R^{3a}$ is independently $R^3$, $C(O)R^a$, $-C(O)OR^a$,

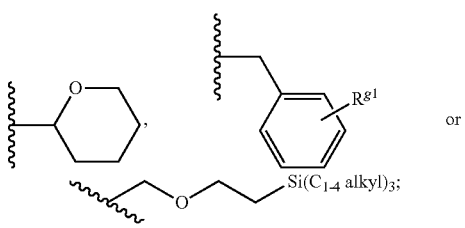
or $R^8$ is independently 5-membered heteroaryl wherein the heteroaryl includes 1 to 4 ring carbon atoms and 1 to 4 ring heteroatoms are each independently selected from: N, $N(R^{e1})$, O, and S, and is substituted with from 0 to 3 $R^g$;

$R^{11}$ is independently $NH_2$ or $NO_2$;

$R^{12}$ is independently H, triphenylmethyl, $C(O)R^a$, $-C(O)OR^a$, $-S(O)_{1-2}(R^b)$, or

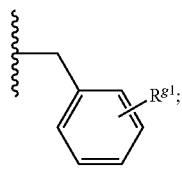

and $R^{e1}$ is independently H, $C(O)R^a$, $-C(O)OR^a$,

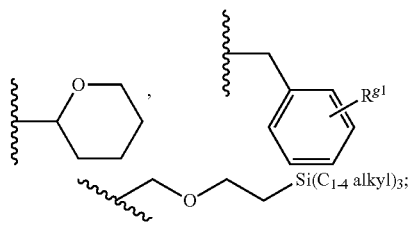

with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido (dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with or without an additive selected from pyrrole, N-methylpyrrole, (carboxymethyl)trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;

for a time from 1 to 96 hours and at a temperature ranging from −20° C. to 120° C. sufficient for cyclization and to produce a compound of Formula (III), or a tautomer, a stereoisomer, or a salt thereof:

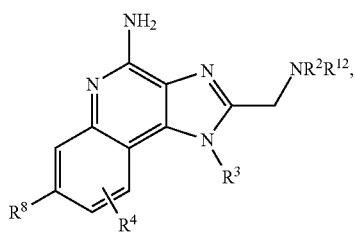

and (2) contacting the compound of Formula (III), or a tautomer, a stereoisomer, or a salt thereof, with Reagent 2 selected from HCl, HBr, $H_2SO_4$, $H_3PO_4$, $HBF_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA, EtOH or a combination thereof, with or without water, for a time from 1 to 48 hours and at a temperature ranging from −20° C. to 120° C. sufficient for hydrolysis and/or de-protection and to produce the compound of Formula (I), or a tautomer, a stereoisomer, or a salt thereof.

In another aspect, the invention provides a method of making a compound of Formula (I) as defined in the 2nd aspect, or a tautomer, a stereoisomer or a salt thereof;

comprising (1) contacting a compound of Formula (II) as defined in the 2nd aspect, or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, in Solvent 1 selected from MeOH, MeTHF, BuOH, EtOH, THF, DMF, NMP, DMF, dioxane, toluene, DME, and DMAc or a combination thereof;

for a time from 1 to 96 hours and at a temperature ranging from −20° C. to 120° C. sufficient for cyclization and to produce a compound of Formula (III) as defined in the 2nd aspect, or a tautomer, a stereoisomer, or a salt thereof;

and (2) contacting the compound of Formula (III), or a tautomer, a stereoisomer, or a salt thereof, with Reagent 2 selected from HCl, HBr, $H_2SO_4$, $H_3PO_4$, $HBF_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA, or a combination thereof, with or without water, for a time from 1 to 48 hours and at a temperature ranging from −20° C. to 120° C. sufficient for hydrolysis and/or de-protection and to produce the compound of Formula (I), or a tautomer, a stereoisomer, or a salt thereof.

In a 3rd aspect, within the scope of the 1st or 2nd aspect, the invention provides a method of making a compound of Formula (I), or a tautomer, a stereoisomer or a salt thereof:

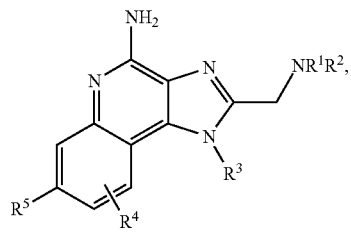

wherein:

$R^1$ is independently $C_{1-6}$ alkyl, $C(O)R^a$, —$C(O)OR^a$, —$S(O)_2(R^b)$, or —$C(O)NR^cR^d$;

$R^2$ is independently H or $C_{1-3}$ alkyl;

$R^3$ is independently H, $C_{1-4}$ haloalkyl, $C_{1-6}$ alkyl optionally substituted with $R^6$, wherein $R^6$ is $CO_2R^a$ or —$CONR^cR^d$;

$R^4$ is independently H, halogen, $C_{1-4}$ alkyl or $C_{1-4}$ alkoxy;

$R^5$ is independently 5-membered heteroaryl wherein the heteroaryl includes 2 to 4 ring carbon atoms and 1 to 3 ring heteroatoms are each independently selected from: N, $N(R^e)$, O, and S, and is substituted with from 0 to 3 $R^g$;

$R^a$ is independently $CF_3$, $C_{1-4}$ alkyl optionally substituted with OH, $C_{3-6}$ cycloalkyl, phenyl, or heteroaryl including from 5 to 6 ring atoms, wherein from 1 to 4 ring atoms are each independently selected from N, $N(R^e)$, O, and S; and $R^b$ is $C_{1-4}$ alkyl;

comprising (1) contacting a compound of Formula (II), or a tautomer, a stereoisomer, or a salt thereof:

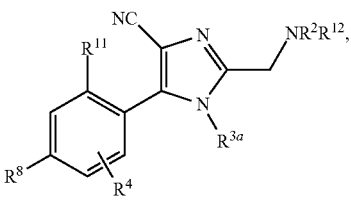

wherein:

$R^{3a}$ is independently $R^3$, $C(O)R^a$, —$C(O)OR^a$,

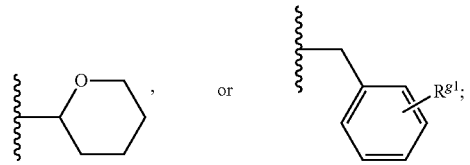

$R^8$ is independently 5-membered heteroaryl wherein the heteroaryl includes 2 to 4 ring carbon atoms and 1 to 3 ring heteroatoms each independently selected from: N, $N(R^{e1})$, O, and S, and is substituted with from 0 to 3 $R^g$;

$R^{12}$ is independently H, $C(O)R^a$, $-C(O)OR^a$, or

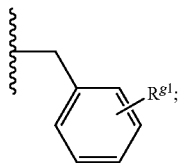

$R^{e1}$ is independently H, $C(O)R^a$, $-C(O)OR^a$,

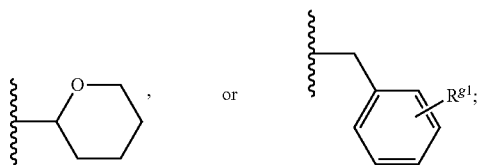

and $R^{g1}$ is independently H, halo, $C_{1-4}$ alkyl, $C_{1-4}$ haloalkyl, $C_{1-4}$ alkoxy, or $C_{1-4}$ haloalkoxy;

with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido (dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with or without an additive selected from pyrrole, N-methylpyrrole, (carboxymethyl)trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;

for a time from 1 to 96 hours and at a temperature ranging from 20° C. and 90° C. sufficient for cyclization and to produce a compound of Formula (III), or a tautomer, a stereoisomer, or a salt thereof:

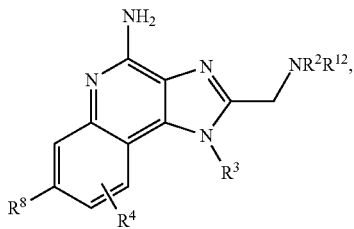
(III)

and (2) contacting the compound of Formula (III), or a tautomer, a stereoisomer, or a salt thereof, with Reagent 2 selected from HCl, HBr, $H_2SO_4$, $H_3PO_4$, $HBF_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA, EtOH or a combination thereof, with or without water, for a time from 1 to 48 hours and at a temperature ranging from 20° C. to 80° C. sufficient for hydrolysis and/or de-protection and to produce the compound of Formula (I), or a tautomer, a stereoisomer, or a salt thereof.

In 4th aspect, the invention provides a method of making a compound of Formula (I) as defined in the 3rd aspect, or a tautomer, a stereoisomer or a salt thereof;

comprising (1) contacting a compound of Formula (II) as defined in the 3rd aspect, or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with an additive selected from pyrrole, N-methylpyrrole, (carboxymethyl)trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;

for a time from 1 to 96 hours and at a temperature ranging from 20° C. and 80° C. sufficient for cyclization and to produce a compound of Formula (III), or a tautomer, a stereoisomer, or a salt thereof;

and (2) contacting the compound of Formula (III) as defined in the 3rd aspect, or a tautomer, a stereoisomer, or a salt thereof, with Reagent 2 selected from HCl, HBr, $H_2SO_4$, $H_3PO_4$, $HBF_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA or a combination thereof, with or without water, for a time from 1 to 48 hours and at a temperature ranging from 20° C. to 80° C. sufficient for hydrolysis and/or de-protection and to produce the compound of Formula (I), or a tautomer, a stereoisomer, or a salt thereof.

In another aspect, the invention provides a method of making a compound of Formula (I) as defined in the 3rd aspect, or a tautomer, a stereoisomer or a salt thereof;

comprising (1) contacting a compound of Formula (II) as defined in the 3rd aspect, or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, in Solvent 1 selected from MeOH, MeTHF, BuOH, EtOH, THF, DMF, NMP, DMF, dioxane, toluene, DME, and DMAc or a combination thereof;

for a time from 1 to 96 hours and at a temperature ranging from 20° C. and 80° C. sufficient for cyclization and to produce a compound of Formula (III), or a tautomer, a stereoisomer, or a salt thereof;

and (2) contacting the compound of Formula (III) as defined in the 3rd aspect, or a tautomer, a stereoisomer, or a salt thereof, with Reagent 2 selected from HCl, HBr, H$_2$SO$_4$, H$_3$PO$_4$, HBF$_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA or a combination thereof, with or without water, for a time from 1 to 48 hours and at a temperature ranging from 20° C. to 80° C. sufficient for hydrolysis and/or de-protection and to produce the compound of Formula (I), or a tautomer, a stereoisomer, or a salt thereof.

In a 5th aspect, within the scope of any of the 1st to 3rd aspects, the invention provides a method of making a compound of Formula (I), or a tautomer, a stereoisomer or a salt thereof:

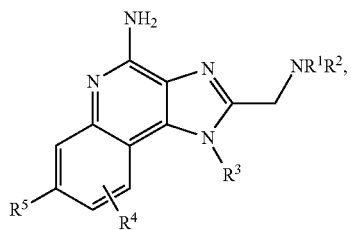

wherein:

R$^1$ is independently C$_{1-6}$ alkyl, C(O)R$^a$, —C(O)OR$^a$, —S(O)$_2$(CH$_3$), or —C(O)N(CH$_3$)$_2$;

R$^2$ is independently H, CH$_3$ or CH$_2$CH$_3$;

R$^3$ is independently H, CH$_3$, or —(CH$_2$)$_3$C(=O)OCH$_3$;

R$^4$ is independently H, F, Cl, C$_{1-2}$ alkyl or C$_{1-2}$ alkoxy;

R$^5$ is independently pyrazolyl, thiazolyl or thienyl; and

R$^a$ is independently C$_{1-4}$ alkyl, cyclopropyl, or thiazolyl;

comprising (1) contacting a compound of Formula (II), or a tautomer, a stereoisomer, or a salt thereof:

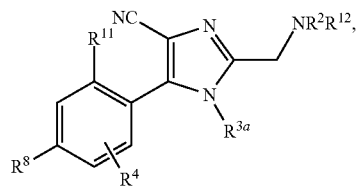

wherein:

R$^{3a}$ is independently R$^3$,

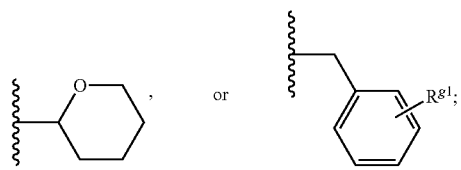

R$^8$ is independently N—(R$^{e1}$)-pyrazolyl, N—(R$^{e1}$)-thiazolyl or thienyl;

R$^{12}$ is independently H, C(O)R$^a$, —C(O)OR$^a$, or

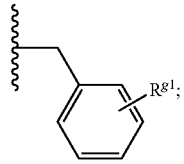

and

R$^{e1}$ is independently H, C(O)R$^a$, —C(O)OR$^a$,

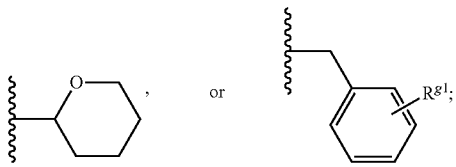

with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido (dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with or without an additive selected from pyrrole, N-methylpyrrole, (carboxymethyl)trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;

for a time from 1 to 48 hours and at a temperature ranging from 30° C. and 80° C. sufficient for cyclization and to produce a compound of Formula (III), or a tautomer, a stereoisomer, or a salt thereof:

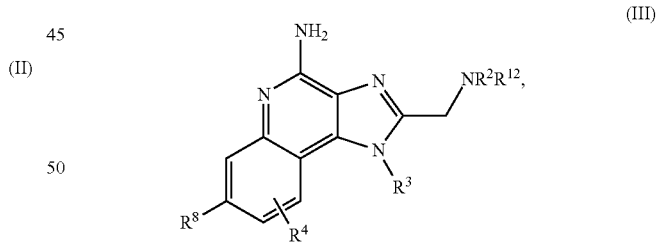

and (2) contacting the compound of Formula (III), or a tautomer, a stereoisomer, or a salt thereof, with Reagent 2 selected from HCl, HBr, H$_2$SO$_4$, H$_3$PO$_4$, HBF$_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA, EtOH or a combination thereof, with or without water, for a time from 1 to 48 hours and at a temperature ranging from 40° C. to 80° C. sufficient for hydrolysis and/or de-protection and to produce the compound of Formula (I), or a tautomer, a stereoisomer, or a salt thereof.

In 6th aspect, the invention provides a method of making a compound of Formula (I) as defined in the 5th aspect, or a tautomer, a stereoisomer or a salt thereof;

comprising (1) contacting a compound of Formula (II) as defined in the 5th aspect, or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with an additive selected from pyrrole, N-methylpyrrole, (carboxymethyl)trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;

for a time from 8 to 48 hours and at a temperature ranging from 40° C. and 80° C. sufficient for cyclization and to produce a compound of Formula (III), or a tautomer, a stereoisomer, or a salt thereof;

and (2) contacting the compound of Formula (III), or a tautomer, a stereoisomer, or a salt thereof, with Reagent 2 selected from HCl, HBr, $H_2SO_4$, $H_3PO_4$, $HBF_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA or a combination thereof, with or without water, for a time from 1 to 48 hours and at a temperature ranging from 40° C. to 80° C. sufficient for hydrolysis and/or de-protection and to produce the compound of Formula (I), or a tautomer, a stereoisomer, or a salt thereof.

In another aspect, the invention provides a method of making a compound of Formula (I) as defined in the 5th aspect, or a tautomer, a stereoisomer or a salt thereof;

comprising (1) contacting a compound of Formula (II) as defined in the 5th aspect, or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, in Solvent 1 selected from MeOH, MeTHF, BuOH, EtOH, THF, DMF, NMP, DMF, dioxane, toluene, DME, and DMAc or a combination thereof;

for a time from 8 to 48 hours and at a temperature ranging from 40° C. and 80° C. sufficient for cyclization and to produce a compound of Formula (III), or a tautomer, a stereoisomer, or a salt thereof;

and (2) contacting the compound of Formula (III), or a tautomer, a stereoisomer, or a salt thereof, with Reagent 2 selected from HCl, HBr, $H_2SO_4$, $H_3PO_4$, $HBF_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA or a combination thereof, with or without water, for a time from 1 to 48 hours and at a temperature ranging from 40° C. to 80° C. sufficient for hydrolysis and/or de-protection and to produce the compound of Formula (I), or a tautomer, a stereoisomer, or a salt thereof.

In a 7th aspect, within the scope of any of the 1st to 3rd aspects, the invention provides a method of making a compound of Formula (I), or a tautomer, a stereoisomer or a salt thereof:

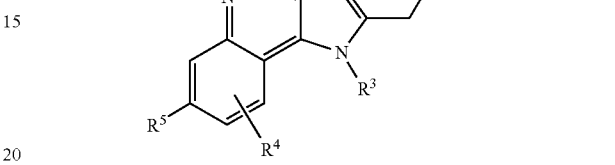

wherein:
$R^1$ is independently $C_{1-6}$ alkyl or $C(O)C_{1-4}$ alkyl;
$R^2$ is independently H, $CH_3$ or $CH_2CH_3$;
$R^3$ is independently H, $CH_3$, or —$(CH_2)_3C(=O)OCH_3$;
$R^4$ is independently H, F, Cl, $C_{1-2}$ alkyl or $C_{1-2}$ alkoxy;
and
$R^5$ is pyrazolyl;
comprising (1) contacting a compound of Formula (II), or a tautomer, a stereoisomer, or a salt thereof:

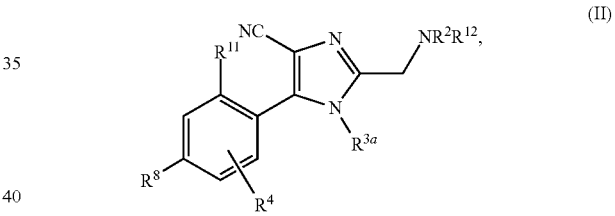

wherein:
$R^{3a}$ is independently $R^3$,

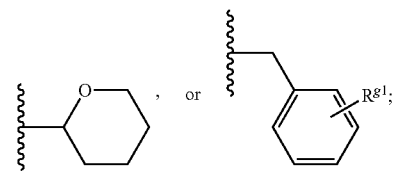

$R^8$ is N—$(R^{e1})$-pyrazolyl;
$R^{12}$ is independently H, $C(O)C_{1-4}$ alkyl, —$C(O)OC_{1-4}$ alkyl, or

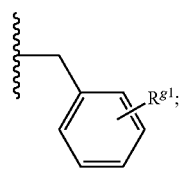

and $R^{e1}$ is independently H, C(O)$C_{1-4}$ alkyl, —C(O)O $C_{1-4}$ alkyl,

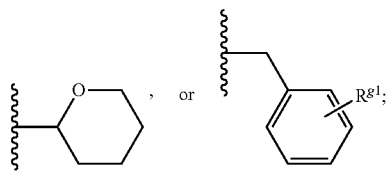

and $R^{g1}$ is independently H, halo or $C_{1-4}$ alkyl;

with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido (dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with or without an additive selected from pyrrole, N-methylpyrrole, (carboxymethyl)trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;

for a time from 1 to 48 hours and at a temperature ranging from 30° C. and 80° C. sufficient for cyclization and to produce a compound of Formula (III), or a tautomer, a stereoisomer, or a salt thereof:

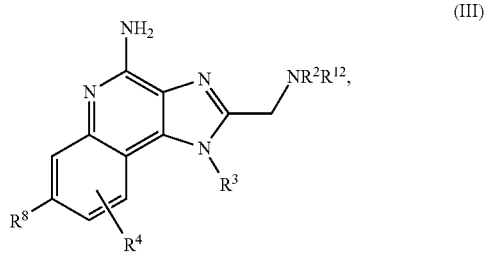

(III)

and (2) contacting the compound of Formula (III), or a tautomer, a stereoisomer, or a salt thereof, with Reagent 2 selected from HCl, HBr, $H_2SO_4$, $H_3PO_4$, $HBF_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA, EtOH or a combination thereof, with or without water, for a time from 1 to 48 hours and at a temperature ranging from 40° C. to 80° C. sufficient for hydrolysis and de-protection and to produce the compound of Formula (I), or a tautomer, a stereoisomer, or a salt thereof.

In an 8th aspect, within the scope of the 7th aspect, the invention provides a method of making a compound of Formula (I), or a tautomer, a stereoisomer or a salt thereof;

comprising (1) contacting a compound of Formula (II), or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with an additive selected from pyrrole, N-methylpyrrole, (carboxymethyl)trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;

for a time from 8 to 48 hours and at a temperature ranging from 40° C. and 80° C. sufficient for cyclization and to produce a compound of Formula (III), or a tautomer, a stereoisomer, or a salt thereof;

and (2) contacting the compound of Formula (III), or a tautomer, a stereoisomer, or a salt thereof, with Reagent 2 selected from HCl, HBr, $H_2SO_4$, $H_3PO_4$, $HBF_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA or a combination thereof, with or without water, for a time from 1 to 48 hours and at a temperature ranging from 40° C. to 80° C. sufficient for hydrolysis and de-protection and to produce the compound of Formula (I), or a tautomer, a stereoisomer, or a salt thereof.

In another aspect, within the scope of the 7th aspect, the invention provides a method of making a compound of Formula (I), or a tautomer, a stereoisomer or a salt thereof;

comprising (1) contacting a compound of Formula (II), or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, in Solvent 1 selected from MeOH, MeTHF, BuOH, EtOH, THF, DMF, NMP, DMF, dioxane, toluene, DME, and DMAc or a combination thereof;

for a time from 8 to 48 hours and at a temperature ranging from 40° C. and 80° C. sufficient for cyclization and to produce a compound of Formula (III), or a tautomer, a stereoisomer, or a salt thereof;

and (2) contacting the compound of Formula (III), or a tautomer, a stereoisomer, or a salt thereof, with Reagent 2 selected from HCl, HBr, $H_2SO_4$, $H_3PO_4$, $HBF_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA or a combination thereof, with or without water, for a time from 1 to 48 hours and at a temperature ranging from 40° C. to 80° C. sufficient for hydrolysis and de-protection and to produce the compound of Formula (I), or a tautomer, a stereoisomer, or a salt thereof.

In another aspect, within the scope of any of the 1st to 3rd aspects, the invention provides a method of making a compound of Formula (I), or a tautomer, a stereoisomer or a salt thereof, wherein:

$R^1$ is independently $C_{1-4}$ alkyl or $C(O)C_{1-4}$ alkyl;
$R^2$ is independently H, $CH_3$ or $CH_2CH_3$;
$R^3$ is independently H, $CH_3$, or —$(CH_2)_3C(\!=\!O)OCH_3$;
$R^4$ is independently H, F, Cl, $C_{1-2}$ alkyl or $C_{1-2}$ alkoxy; and
$R^5$ is pyrazolyl;
comprising (1) contacting a compound of Formula (II), or a tautomer, a stereoisomer, or a salt thereof, wherein:
$R^{3a}$ is independently $R^3$,

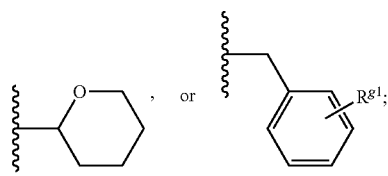

$R^8$ is N—$(R^{e1})$-pyrazolyl;
$R^{12}$ is independently —$C(O)OC_{1-4}$ alkyl, or

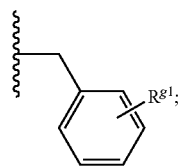

and
$R^{e1}$ is independently —$C(O)O$ $C_{1-4}$ alkyl,

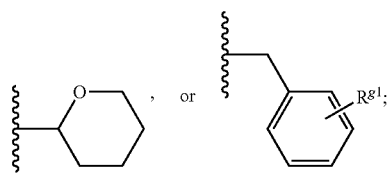

and
$R^{g1}$ is independently H, halo or $C_{1-4}$ alkyl;
with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, in Solvent 1 selected from MeOH, MeTHF, BuOH, EtOH, THF, DMF, NMP, DMF, dioxane, toluene, DME, and DMAc or a combination thereof;
for a time from 8 to 48 hours and at a temperature ranging from 40° C. and 80° C. sufficient for cyclization and to produce a compound of Formula (III), or a tautomer, a stereoisomer, or a salt thereof;
and (2) contacting the compound of Formula (III), or a tautomer, a stereoisomer, or a salt thereof, with Reagent 2 selected from HCl, HBr, $H_2SO_4$, $H_3PO_4$, $HBF_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA, EtOH or a combination thereof, with or without water, for a time from 1 to 48 hours and at a temperature ranging from 40° C. to 80° C. sufficient for hydrolysis and de-protection and to produce the compound of Formula (I), or a tautomer, a stereoisomer, or a salt thereof.

In another aspect, within the scope of the above immediate aspect, the invention provides a method of making a compound of Formula (I), or a tautomer, a stereoisomer or a salt thereof;
comprising (1) contacting a compound of Formula (II), or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, in Solvent 1 selected from MeOH, MeTHF, BuOH, EtOH, THF, DMF, NMP, DMF, dioxane, toluene, DME, and DMAc or a combination thereof;
for a time from 8 to 48 hours and at a temperature ranging from 40° C. and 80° C. sufficient for cyclization and to produce a compound of Formula (III), or a tautomer, a stereoisomer, or a salt thereof;
and (2) contacting the compound of Formula (III), or a tautomer, a stereoisomer, or a salt thereof, with Reagent 2 selected from HCl, HBr, $H_2SO_4$, $H_3PO_4$, $HBF_4$, 1,5-naphthalenedisulfonic acid, benzenesulfonic acid, methanesulfonic acid, p-toluenesulfonic acid, camphorsulfonic acid, and ethanesulfonic acid or a combination thereof, in Solvent 2 selected from MTBE, MeOH, MIBK, iPrOAc, toluene, 2-Me-THF, MeCN, CPME, IPA or a combination thereof, with or without water, for a time from 1 to 48 hours and at a temperature ranging from 40° C. to 80° C. sufficient for hydrolysis and de-protection and to produce the compound of Formula (I), or a tautomer, a stereoisomer, or a salt thereof.

In another aspect, the invention provides a compound of Formula (III), or a tautomer, a stereoisomer, or a salt thereof:

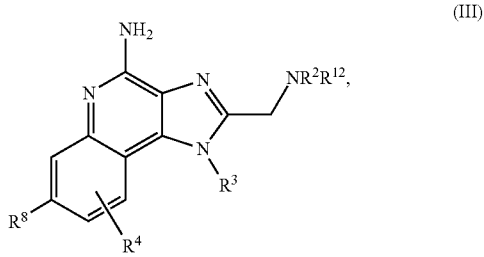

wherein $R^2$, $R^3$, $R^4$, $R^8$, $R^{12}$, and other variables are as defined as in any of the 1st to 3rd, 5th and 7th aspects.

In another aspect, the invention provides a compound of Formula (III), or a tautomer, a stereoisomer, or a salt thereof, wherein: $R^2$, $R^3$, $R^4$, $R^8$, $R^{12}$, and other variables are as defined as in any of the 1st to 3rd, 5th and 7th aspects;
$R^8$ is independently N—$(R^{e1})$-pyrazolyl, N—$(R^{e1})$-thiazolyl; and
$R^{e1}$ is independently H, $C(O)C_{1-4}$ alkyl, —$C(O)OC_{1-4}$ alkyl,

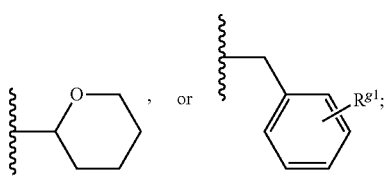

and $R^{g1}$ is independently H, halo or $C_{1-4}$ alkyl.

In a 9th aspect, the invention provides a compound of Formula (III), or a tautomer, a stereoisomer, or a salt thereof, wherein:

$R^2$ is independently H or $C_{1-6}$ alkyl;

$R^3$ is independently H, $C_{1-6}$ haloalkyl, or $C_{1-8}$ alkyl optionally substituted with $R^6$, wherein $R^6$ is OH, $C_{1-4}$ alkoxy, $C_{1-4}$ haloalkoxy, $CO_2R^a$, or —$CONR^cR^d$;

$R^4$ is independently H, halogen, cyano, OH, $C_{1-4}$ alkyl, $C_{1-4}$ alkoxy, $C_{1-4}$ haloalkyl, or $C_{1-4}$ haloalkoxy;

$R^8$ is independently N—$(R^{e1})$-pyrazolyl, N—$(R^{e1})$-thiazolyl;

$R^{12}$ is independently H, triphenylmethyl, $C(O)R^a$, —$C(O)OR^a$, —$S(O)_{1-2}(R^b)$, or

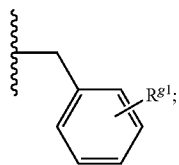

$R^a$ is, at each occurrence, independently:

(i) $C_{1-6}$ alkyl optionally substituted with from 1 to 2 $R^h$;

(ii) $C_{1-6}$ haloalkyl;

(iii) —$(C_{0-3}$ alkylene)-$C_{3-6}$ cycloalkyl, wherein the cycloalkyl is optionally substituted with from 1 to 2 $R^f$;

(iv) —$(C_{0-3}$ alkylene)-heterocyclyl including from 3 to 8 ring atoms, wherein from 1 to 3 ring atoms are each independently selected from $N(R^e)$, O, and S, wherein the heterocyclyl is optionally substituted with from 1 to 4 independently selected $R^f$;

(v) —$(C_{0-3}$ alkylene)-phenyl optionally substituted with from 1 to 4 independently selected $R^g$; or (vi) —$(C_{0-3}$ alkylene)-heteroaryl including from 5 to 6 ring atoms, wherein from 1 to 4 ring atoms are each independently selected from N, $N(R^e)$, O, and S, wherein the heteroaryl is optionally substituted with from 1 to 3 independently selected $R^g$;

$R^b$ is $C_{1-6}$ alkyl;

each occurrence of $R^c$ and $R^d$ is independently H or $C_{1-4}$ alkyl;

each occurrence of $R^e$ is independently H or $C_{1-4}$ alkyl;

each occurrence of $R^f$ is independently $C_{1-6}$ alkyl, $C_{1-4}$ haloalkyl, OH, F, Cl, $C_{1-4}$ alkoxy, $C_{1-4}$ haloalkoxy, cyano, or phenyl optionally substituted with from 1 to 4 $R^g$;

each occurrence of $R^g$ is independently halogen, cyano, $C_{1-6}$ alkyl, $C_{1-4}$ haloalkyl, $C_{1-4}$ alkoxy, or $C_{1-4}$ haloalkoxy;

each occurrence of $R^h$ is independently OH, F, Cl, $C_{1-4}$ alkoxy, $C_{1-4}$ haloalkoxy, or cyano;

$R^{e1}$ is independently $C(O)C_{1-4}$ alkyl, —$C(O)O\ C_{1-4}$ alkyl,

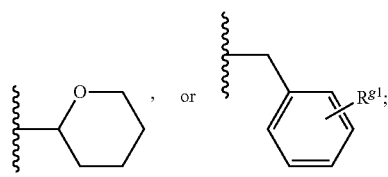

and $R^{g1}$ is independently H, halo or $C_{1-4}$ alkyl.

In another aspect, the invention provides a compound of Formula (III), or a tautomer, a stereoisomer, or a salt thereof, wherein $R^2$, $R^3$, $R^4$, $R^8$, $R^{12}$, and other variables are as defined as in any of the 1st to 3rd, 5th and 7th aspects;

$R^8$ is N—$(R^{e1})$-pyrazolyl; and $R^{e1}$ is independently H, Bn, Boc, or

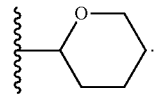

In a 10th aspect, within the scope of the 9th aspect, the invention provides a compound of Formula (III), or a tautomer, a stereoisomer, or a salt thereof, wherein:

$R^2$ is independently H or $C_{1-3}$ alkyl;

$R^3$ is independently H, $C_{1-4}$ haloalkyl, $C_{1-6}$ alkyl optionally substituted with $R^6$, wherein $R^6$ is $CO_2R^a$ or —$CONR^cR^d$;

$R^4$ is independently H, halogen, $C_{1-4}$ alkyl or $C_{1-4}$ alkoxy;

$R^8$ is N—$(R^{e1})$-pyrazolyl;

$R^{12}$ is independently H, $C(O)C_{1-4}$ alkyl, —$C(O)OC_{1-4}$ alkyl, or

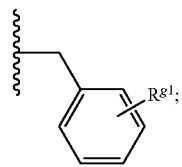

and $R^{e1}$ is independently Bn, Boc, or

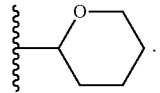

In another aspect, the invention provides a compound of Formula (III), or a tautomer, a stereoisomer, or a salt thereof, wherein $R^2$, $R^3$, $R^4$, $R^8$, $R^{12}$, and other variables are as defined as in any of the 1st to 3rd, 5th and 7th aspects;

$R^8$ is N—$(R^{e1})$-pyrazolyl; and $R^{e1}$ is independently Boc, or

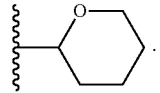

In a 11th aspect, the invention provides a compound of Formula (II), or a tautomer, a stereoisomer or a salt thereof:

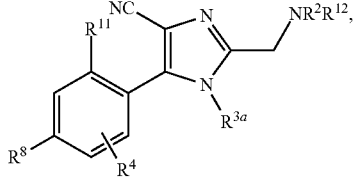
(II)

wherein $R^2$, $R^{3a}$, $R^4$, $R^8$, $R^{11}$, $R^{12}$ and other variables are as defined as in any of the 1st to 3rd, 5th and 7th aspects.

In a 12th aspect, the invention provides a compound of Formula (II), or a tautomer, a stereoisomer, or a salt thereof, wherein: $R^2$, $R^{3a}$, $R^4$, $R^8$, $R^{11}$, $R^{12}$ and other variables are as defined as in any of the 1st to 3rd, 5th and 7th aspects;

$R^8$ is independently N—$(R^{e1})$-pyrazolyl, N—$(R^{e1})$-thiazolyl; and $R^{e1}$ is independently H, C(O)$C_{1-4}$ alkyl, —C(O)O $C_{1-4}$ alkyl,

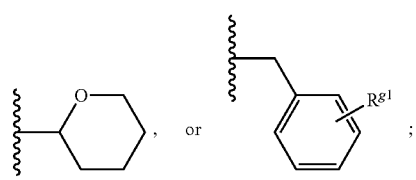

and $R^{g1}$ is independently H, halo or $C_{1-4}$ alkyl.

In a 13th aspect, the invention provides a compound of Formula (II), or a tautomer, a stereoisomer, or a salt thereof, wherein $R^2$, $R^{3a}$, $R^4$, $R^8$, $R^{11}$, $R^{12}$ and other variables are as defined as in any of the 1st to 3rd, 5th and 7th aspects;

$R^8$ is N—$(R^{e1})$-pyrazolyl; and $R^{e1}$ is independently H, Bn, Boc, or

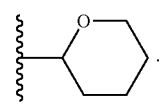.

In another aspect, the invention provides a compound of Formula (II), or a tautomer, a stereoisomer, or a salt thereof, wherein $R^2$, $R^{3a}$, $R^4$, $R^8$, $R^{11}$, $R^{12}$ and other variables are as defined as in any of the 1st to 3rd, 5th and 7th aspects;

$R^8$ is N—$(R^{e1})$-pyrazolyl; and $R^{e1}$ is independently Boc, or

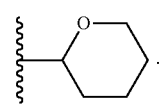.

In a 14th aspect, the invention provides a method of making a compound of Formula (III), or a tautomer, a stereoisomer or a salt thereof:

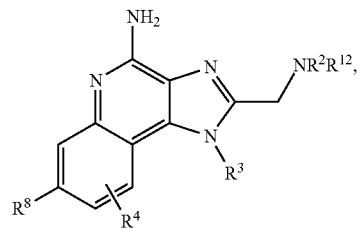
(III)

wherein $R^2$, $R^3$, $R^4$, $R^8$, $R^{12}$ and other variables are as defined as in any of the 1st to 3rd, $5^{th}$, 7th, 9th and 10th aspects;

comprising (1) contacting a compound of Formula (II), or a tautomer, a stereoisomer, or a salt thereof:

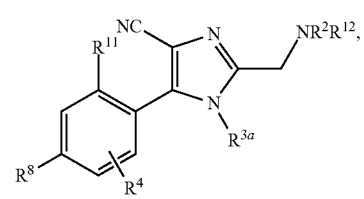
(II)

wherein $R^2$, $R^{3a}$, $R^4$, $R^8$, $R^{11}$ and $R^{12}$ and other variables are as defined as in any of the 1st to 3rd, 5th and 7th, 11th to 13th aspects;

with a mixture of Reagent 1 selected from a Brønsted acid, a Lewis acid, and a transition metal catalyst or a combination thereof, with or without Base 1 selected from a Brønsted base and a Lewis base, with or without an additive, in Solvent 1 that is a protic, aprotic or polar organic solvent or organic solvent mixture;

for a time and at a temperature sufficient for cyclization and to produce a compound of Formula (III), or a tautomer, a stereoisomer, or a salt thereof.

In another aspect, within the scope of the 14th aspect, the invention provides a method of making a compound of Formula (III), or a tautomer, a stereoisomer or a salt thereof;

comprising (1) contacting a compound of Formula (II), or a tautomer, a stereoisomer, or a salt thereof, with a mixture of Reagent 1 selected from a Brønsted acid, a Lewis acid, and a transition metal catalyst or a combination thereof, with or without Base 1 selected from a Brønsted base and a Lewis base, in Solvent 1 that is a protic, aprotic or polar organic solvent or organic solvent mixture;

for a time and at a temperature sufficient for cyclization and to produce a compound of Formula (III), or a tautomer, a stereoisomer, or a salt thereof.

In a 15th aspect, within the scope of the 14th aspect, the invention provides a method of making a compound of Formula (III), or a tautomer, a stereoisomer or a salt thereof:

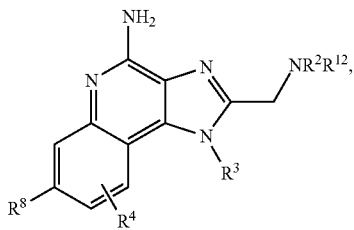

(III)

wherein:
comprising (1) contacting a compound of Formula (II), or a tautomer, a stereoisomer, or a salt thereof:

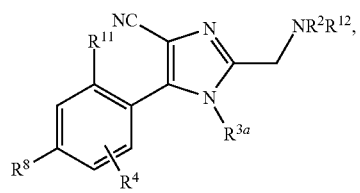

(II)

with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with or without an additive selected from pyrrole, N-methylpyrrole, (carboxymethyl)trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;
for a time from 1 to 96 hours and at a temperature ranging from −20° C. to 120° C. sufficient for cyclization and to produce a compound of Formula (III), or a tautomer, a stereoisomer, or a salt thereof.

In a 16th aspect, within the scope of the 14th aspect, the invention provides a method of making a compound of Formula (III), or a tautomer, a stereoisomer or a salt thereof;
comprising (1) contacting a compound of Formula (II), or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with an additive selected from pyrrole, N-methylpyrrole, (carboxymethyl)trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;
for a time from 1 to 96 hours and at a temperature ranging from −20° C. to 120° C. sufficient for cyclization and to produce a compound of Formula (III), or a tautomer, a stereoisomer, or a salt thereof.

In another aspect, within the scope of the 14th aspect, the invention provides a method of making a compound of Formula (III), or a tautomer, a stereoisomer or a salt thereof;
comprising (1) contacting a compound of Formula (II), or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, in Solvent 1 selected from MeOH, MeTHF, BuOH, EtOH, THF, DMF, NMP, DMF, dioxane, toluene, DME, and DMAc or a combination thereof;
for a time from 1 to 96 hours and at a temperature ranging from −20° C. to 120° C. sufficient for cyclization and to produce a compound of Formula (III), or a tautomer, a stereoisomer, or a salt thereof.

In a 17th aspect, within the scope of the 14th or 15th aspect, the invention provides a method of making a compound of Formula (III), or a tautomer, a stereoisomer or a salt thereof;
comprising (1) contacting a compound of Formula (II), or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with or without an additive selected from pyrrole, N-methylpyrrol e, (carboxymethyl)trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;
for a time from 1 to 96 hours and at a temperature ranging from 20° C. and 80° C. sufficient for cyclization and to produce a compound of Formula (III), or a tautomer, a stereoisomer, or a salt thereof.

In an 18th aspect, within the scope of the 14th or 16th aspect, the invention provides a method of making a compound of Formula (III), or a tautomer, a stereoisomer or a salt thereof;
comprising (1) contacting a compound of Formula (II), or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with an additive selected from pyrrole, N-methylpyrrole, (carboxymethyl) trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;

for a time from 1 to 96 hours and at a temperature ranging from 20° C. and 80° C. sufficient for cyclization and to produce a compound of Formula (III), or a tautomer, a stereoisomer, or a salt thereof.

In another aspect, within the scope of the 14th or 15th aspect, the invention provides a method of making a compound of Formula (III), or a tautomer, a stereoisomer or a salt thereof;

comprising (1) contacting a compound of Formula (II), or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, in Solvent 1 selected from MeOH, MeTHF, BuOH, EtOH, THF, DMF, NMP, DMF, dioxane, toluene, DME, and DMAc or a combination thereof;

for a time from 1 to 96 hours and at a temperature ranging from 20° C. and 80° C. sufficient for cyclization and to produce a compound of Formula (III), or a tautomer, a stereoisomer, or a salt thereof.

In a 19th aspect, within the scope of any of the 14th, 15th and 17th aspects, the invention provides a method of making a compound of Formula (III), or a tautomer, a stereoisomer or a salt thereof;

comprising (1) contacting a compound of Formula (II), or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with or without an additive selected from pyrrole, N-methylpyrrol e, (carboxymethyl)trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;

for a time from 1 to 48 hours and at a temperature ranging from 30° C. and 80° C. sufficient for cyclization and to produce a compound of Formula (III), or a tautomer, a stereoisomer, or a salt thereof.

In another aspect, within the scope of any of the 14th, 15th and 17th aspects, the invention provides a method of making a compound of Formula (III), or a tautomer, a stereoisomer or a salt thereof;

comprising (1) contacting a compound of Formula (II), or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, with an additive selected from pyrrole, N-methylpyrrole, (carboxymethyl) trimethylammonium chloride hydrazide, 2,4-dimethylpyrrole, 2,5-dimethylpyrrole, 4-methoxy-2-methylindole, 2-methylfuran, 1,2-dimethylindole, 2-methylthiophene, and N-methylindole, in Solvent 1 selected from MeOH, MeTHF, BuOH, EtOH, THF, DMF, NMP, DMF, dioxane, toluene, DME, and DMAc or a combination thereof;

for a time from 8 to 48 hours and at a temperature ranging from 40° C. and 80° C. sufficient for cyclization and to produce a compound of Formula (III), or a tautomer, a stereoisomer, or a salt thereof.

In another aspect, within the scope of any of the 14th, 15th and 17th aspects, the invention provides a method of making a compound of Formula (III), or a tautomer, a stereoisomer or a salt thereof;

comprising (1) contacting a compound of Formula (II), or a tautomer, a stereoisomer, or a salt thereof, with a mixture of Reagent 1 selected from dichloroacetic acid, acetic acid, p-toluenesulfonic acid, HCl, citric acid, diphenylphosphinic acid, oxalic acid, methyl phosphonic acid, phenylphosphonic acid, salicylic acid and hydrido(dimethylphosphinous acid-kP)[hydrogen bis(dimethylphosphinito-kP)]platinum (II) or a combination thereof, with or without Base 1 selected from NaOAc, KOAc, NaOPiv, KOPiv, NaOMe, KOMe and N,N-diisopropylethylamine, in Solvent 1 selected from MeOH, MeTHF, BuOH, EtOH, THF, DMF, NMP, DMF, dioxane, toluene, DME, and DMAc or a combination thereof;

for a time from 8 to 48 hours and at a temperature ranging from 40° C. and 80° C. sufficient for cyclization and to produce a compound of Formula (III), or a tautomer, a stereoisomer, or a salt thereof.

In a 20th aspect, the invention provides a method of making a compound of Formula (II), or a tautomer, a stereoisomer or a salt thereof:

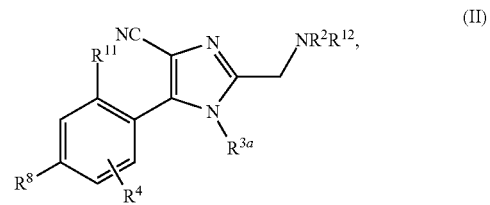

wherein $R^2$, $R^{3a}$, $R^4$, $R^8$, $R^{11}$ and $R^{12}$ and other variables are as defined as in any of the 1st to 3rd, 5th and 7th, 11th to 13th aspects;

comprising (1) contacting a compound of Formula (IV), or a tautomer, a stereoisomer, or a salt thereof:

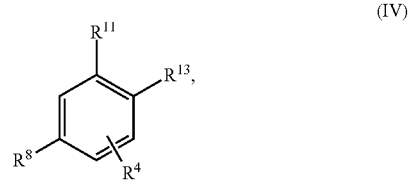

wherein $R^4$, $R^8$, and $R^{11}$ and other variables are as defined as in any of the 1st to 3rd, 5th and 7th, 11th to 13th aspects;

$R^{13}$ is independently H, halogen, —OS(O)$_2$R$^{b1}$, —B(OR$^{b2}$)$_2$, or —BF$_3$K;

$R^{b1}$ is independently C$_{1-4}$ alkyl, C$_{1-4}$ haloalkyl, or phenyl substituted with from 0 to 3 R$^{g2}$;

$R^{b2}$ is independently H or C$_{1-4}$ alkyl;

alternatively, two R$^{b2}$s together with the oxygen atoms to which they are attached, forms heterocyclyl including the boron atom and additional 2 to 5 ring carbon atoms, wherein the heterocyclyl is substituted with from 0 to 4 R$^{b2}$;

$R^{b2}$ is independently C$_{1-4}$ alkyl or —C(O)OC$_{1-4}$ alkyl;

alternatively, two R$^{b2}$s together with the oxygen atoms to which they are attached, forms

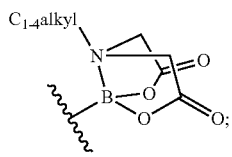

$R^{b2}$ is independently C$_{1-4}$ alkyl or —C(O)OC$_{1-4}$ alkyl; and $R^{g2}$ is independently halo, C$_{1-4}$ alkyl, C$_{1-4}$ haloalkyl, C$_{1-4}$ alkoxy, or C$_{1-4}$ haloalkoxy;

with a compound of Formula (V), or a tautomer, a stereoisomer, or a salt thereof:

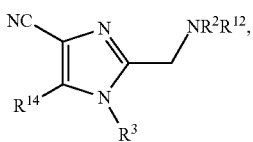

wherein R$^2$, R$^3$, R$^{12}$ and other variables are as defined as in any of any of the 1st to 3rd, 5th and 7th, 11th to 13th aspects; and $R^{14}$ is independently H, halogen, or —OS(O)$_2$R$^{b1}$; and $R^{b1}$ is as defined as above for Formula (IV);

and with a mixture of (a) a transition metal catalyst; with or without (b) a phosphine ligand; and (c) Base 2 selected from a Brønsted base and a Lewis base; in Solvent 3 that is a protic, aprotic or polar organic solvent media;

for a time and at a temperature sufficient for coupling and to produce a compound of Formula (II), or a tautomer, a stereoisomer, or a salt thereof.

In a 21st aspect, within the scope of the 20th aspect, the invention provides a method of making a compound of Formula (II), or a tautomer, a stereoisomer or a salt thereof:

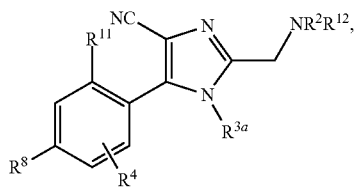

wherein R$^2$, R$^{3a}$, R$^4$, R$^8$, R$^{11}$ and R$^{12}$ and other variables are as defined as in any of the 1st to 3rd, 5th and 7th, 11th to 13th aspects;

comprising (1) contacting a compound of Formula (IV), or a tautomer, a stereoisomer, or a salt thereof:

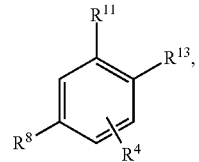

wherein:

$R^{13}$ is independently H, halogen, —OS(O)$_2$R$^{b1}$, —B(OH)$_2$, —B(OC$_{1-4}$ alkyl)$_2$, —BF$_3$K,

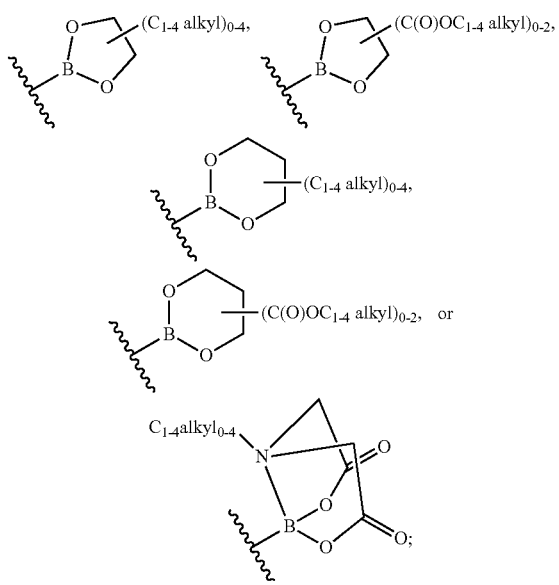

$R^{b1}$ is independently C$_{1-4}$ alkyl, C$_{1-4}$ haloalkyl, or phenyl substituted with from 0 to 3 R$^{g2}$; and $R^{g2}$ is independently halo, C$_{1-4}$ alkyl, or C$_{1-4}$ haloalkyl;

with a compound of Formula (V), or a tautomer, a stereoisomer, or a salt thereof:

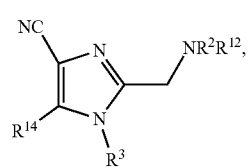

wherein R$^{14}$ is independently H, halogen, or —OS(O)$_2$R$^{b1}$; and R$^{b1}$ is as defined as above for Formula (IV);

and with a mixture of (a) a transition metal catalyst; with or without (b) a phosphine ligand; and (c) Base 2 selected from a Brønsted base and a Lewis base; in Solvent 3 that is a protic, aprotic or polar organic solvent media;

for a time and at a temperature sufficient for coupling and to produce a compound of Formula (II), or a tautomer, a stereoisomer, or a salt thereof.

In a 22nd aspect, within the scope of the 20th or 21st aspect, the invention provides a method of making a compound of Formula (II), or a tautomer, a stereoisomer or a salt thereof;

comprising (1) contacting a compound of Formula (IV), or a tautomer, a stereoisomer, or a salt thereof, wherein R$^{13}$ is independently H, halogen, —OMs, —OTs, —OTf, —B(OH)₂, —BPin, —B(npg) or —BF₃K;

with a compound of Formula (V), or a tautomer, a stereoisomer, or a salt thereof; wherein $R^{14}$ is independently F, Cl, Br, —OMs, —OTs, or —OTf;

and with a mixture of (a) a transition metal catalyst selected from PdCl₂(PPh₃)₂, Pd(AtaPhos)₂Cl₂, (DPEPhos)PdCl₂, (DPPF)PdCl₂, (PCy₂tBu)₂PdCl₂, Pd(OAc)₂, Pd₂(dba)₃, Pd(dba)₂ (MeCN)₂PdCl₂, [(crotyl)PdCl]₂, [(cinnamyl)PdCl]₂ and [(allyl)PdCl]₂; with or without (b) a phosphine ligand selected from PPh₃, DPEPhos, DPPF, PCy₂tBu, PCy₂tBuHBF₄, CyXantphos, PtBu₂Me, PtBu₂MeHBF₄, XPhos and AtaPhos; and (c) Base 2 selected from K₃PO₄, KOH, K₂CO₃, NaOH, NaOMe, KOMe, NaOtBu, and KOtBu; in Solvent 3 selected from MeTHF, THF, MeOH, EtOH, dioxane, toluene, DMAc, DME and NMP or a combination thereof;

for a time from 1 to 96 hours and at a temperature ranging from 20° C. to 80° C. sufficient for coupling and to produce a compound of Formula (II), or a tautomer, a stereoisomer, or a salt thereof.

In another aspect, within the scope of the 20th or 21st aspect, the invention provides a method of making a compound of Formula (II), or a tautomer, a stereoisomer or a salt thereof;

comprising (1) contacting a compound of Formula (IV), or a tautomer, a stereoisomer, or a salt thereof, with a compound of Formula (V), or a tautomer, a stereoisomer, or a salt thereof;

and with a mixture of (a) a transition metal catalyst selected from PdCl₂(PPh₃)₂, (DPEPhos)PdCl₂, (DPPF)PdCl₂, (PCy₂tBu)₂PdCl₂, Pd(OAc)₂, Pd₂(dba)₃, Pd(dba)₂ (MeCN)₂PdCl₂ and [(allyl)PdCl]₂; with or without (b) a phosphine ligand selected from CyXantphos, PtBu₂Me, XPhos and AtaPhos; and (c) Base 2 selected from K₃PO₄, KOH, K₂CO₃, NaOH, NaOMe and KOMe; in Solvent 3 selected from MeTHF, THF, MeOH, EtOH, dioxane, toluene, DMAc, DME and NMP or a combination thereof;

for a time from 1 to 96 hours and at a temperature ranging from 20° C. to 80° C. sufficient for coupling and to produce a compound of Formula (II), or a tautomer, a stereoisomer, or a salt thereof.

In a 23rd aspect, within the scope of any of the 20th to 22nd aspects, the invention provides a method of making a compound of Formula (II), or a tautomer, a stereoisomer or a salt thereof;

comprising (1) contacting a compound of Formula (IV), or a tautomer, a stereoisomer, or a salt thereof, with a compound of Formula (V), or a tautomer, a stereoisomer, or a salt thereof, and with a mixture of (a) a transition metal catalyst selected from PdCl₂(PPh₃)₂, Pd(AtaPhos)₂Cl₂, (DPEPhos)PdCl₂, (DPPF)PdCl₂, (PCy₂tBu)₂PdCl₂, Pd(OAc)₂, Pd₂(dba)₃, Pd(dba)₂ (MeCN)₂PdCl₂, [(crotyl)PdCl]₂, [(cinnamyl)PdCl]₂ and [(allyl)PdCl]₂; with or without (b) a phosphine ligand selected from PPh₃, DPEPhos, DPPF, PCy₂tBu, PCy₂tBuHBF₄, CyXantphos, PtBu₂Me, PtBu₂MeHBF₄, XPhos and AtaPhos; and (c) Base 2 selected from aqueous K₃PO₄, aqueous KOH, aqueous K₂CO₃, aqueous NaOH, anhydrous NaOMe anhydrous KOMe, anhydrous NaOtBu, and anhydrous KOtBu; in Solvent 3 selected from MeTHF, THF, MeOH, EtOH, dioxane, toluene, DMAc, DME and NMP or a combination thereof;

for a time from 2 to 48 hours and at a temperature ranging from 20° C. to 80° C. sufficient for coupling and to produce a compound of Formula (II), or a tautomer, a stereoisomer, or a salt thereof.

In another aspect, within the scope of any of the 20th to 22nd aspects, the invention provides a method of making a compound of Formula (II), or a tautomer, a stereoisomer or a salt thereof;

comprising (1) contacting a compound of Formula (IV), or a tautomer, a stereoisomer, or a salt thereof, with a compound of Formula (V), or a tautomer, a stereoisomer, or a salt thereof; and with a mixture of (a) a transition metal catalyst selected from PdCl₂(PPh₃)₂, (DPEPhos)PdCl₂, (DPPF)PdCl₂, (PCy₂tBu)₂PdCl₂, Pd(OAc)₂, Pd₂(dba)₃, Pd(dba)₂ (MeCN)₂PdCl₂ and [(allyl)PdCl]₂; with or without (b) a phosphine ligand selected from CyXantphos, PtBu₂Me, XPhos and AtaPhos; and (c) Base 2 selected from aqueous K₃PO₄, aqueous KOH, aqueous K₂CO₃, aqueous NaOH, anhydrous NaOMe and anhydrous KOMe; in Solvent 3 selected from MeTHF, THF, MeOH, EtOH, dioxane, toluene, DMAc, DME and NMP or a combination thereof;

for a time from 4 to 96 hours and at a temperature ranging from 20° C. to 80° C. sufficient for coupling and to produce a compound of Formula (II), or a tautomer, a stereoisomer, or a salt thereof.

In a 24th aspect, within the scope of any of the 20th to 23rd aspects, the invention provides a method of making a compound of Formula (II), or a tautomer, a stereoisomer or a salt thereof:

comprising (1) contacting a compound of Formula (IV), or a tautomer, a stereoisomer, or a salt thereof;

with a compound of Formula (V), or a tautomer, a stereoisomer, or a salt thereof;

for a time from 4 to 20 hours and at a temperature ranging from 40° C. to 80° C. sufficient for coupling and to produce a compound of Formula (II), or a tautomer, a stereoisomer, or a salt thereof.

In a 25th aspect, the invention provides a compound of Formula (IV), or a tautomer, a stereoisomer, or a salt thereof:

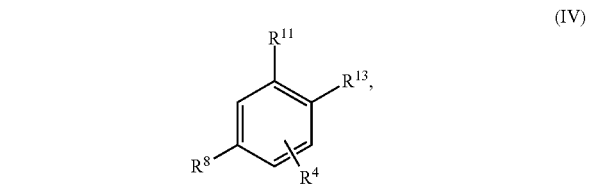

wherein $R^4$, $R^8$, $R^{11}$ and other variables are as defined as in any of the 1st to 3rd, 5th, 7th, 9th and 10th aspects and $R^{13}$ is as defined as in any of the 20th to 23rd aspects.

In a 26th aspect, within the scope of the 25th aspect, invention provides a compound of Formula (IV), or a tautomer, a stereoisomer, or a salt thereof, wherein:

$R^8$ is independently N—($R^{e1}$)-pyrazolyl, N—($R^{e1}$)-thiazolyl;

$R^{13}$ is halogen, —B(OH)₂, —BPin or —BF₃K;

$R^{e1}$ is independently H, C(O)C₁₋₄ alkyl, —C(O)OC₁₋₄ alkyl,

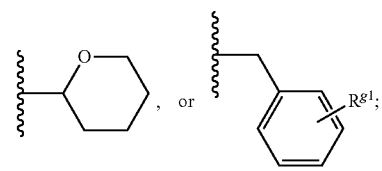

and $R^{g1}$ is independently H, halo or C₁₋₄ alkyl.

In another aspect, within the scope of the 25th or 26th aspect, invention provides a compound of Formula (IV), or a tautomer, a stereoisomer, or a salt thereof, wherein:
R$^8$ is N—(R$^{e1}$)-pyrazolyl; and
R$^{e1}$ is independently H, Bn, Boc, or

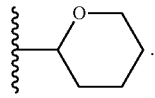.

In a 27th aspect, within the scope of the 25th or 26th aspect, invention provides a compound of Formula (IV), or a tautomer, a stereoisomer, or a salt thereof, wherein:
R$^8$ is N—(R$^{e1}$)-pyrazolyl; and
R$^{e1}$ is independently Bn, Boc, or

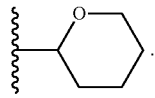.

In a 28th aspect, the invention provides a method of making a compound of Formula (IV), or a tautomer, a stereoisomer, or a salt thereof; wherein R$^4$, R$^{11}$, and other variable are as defined as in any of the 1st to 3rd, 5th, 7th, 9th and 10th aspects;
R$^8$ is independently N—(R$^{e1}$)-pyrazolyl;
R$^{13}$ is independently H, halogen, —OS(O)$_2$R$^{b1}$, —B(OH)$_2$, —BPin, —B(npg) or —BF$_3$K;
R$^{b1}$ is independently C$_{1-4}$ alkyl, C$_{1-4}$ haloalkyl, or phenyl substituted with from 0to 3 R$^{g2}$;
R$^{e1}$ is independently H, C(O)C$_{1-4}$ alkyl, —C(O)OC$_{1-4}$ alkyl,

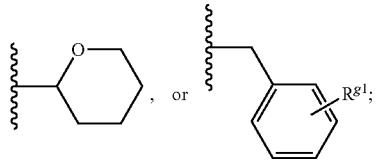

R$^{g1}$ is independently H, halo or C$_{1-4}$ alkyl; and
R$^{g2}$ is independently halo, C$_{1-4}$ alkyl, C$_{1-4}$ haloalkyl, C$_{1-4}$ alkoxy, or C$_{1-4}$ haloalkoxy;
comprising (1) contacting a compound of Formula (VI) or a tautomer, a stereoisomer, or a salt thereof:

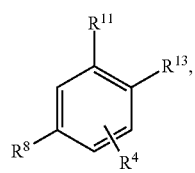

(IV)

wherein R$^4$, R$^{11}$, and other variables are as defined as in any of the 1st to 3rd, 5th, 7th, 9th and 10th aspects and R$^{13}$ is as defined as above for Formula (IV); and
R$^{16}$ is independently halogen;
with a compound of Formula (VII) or a tautomer, a stereoisomer, or a salt thereof:

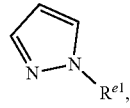

(VII)

wherein: R$^{e1}$ is independently H, C(O)C$_{1-4}$ alkyl, —C(O)OC$_{1-4}$ alkyl,

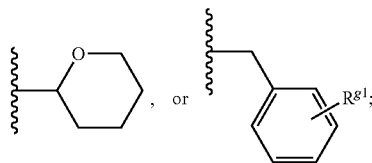

R$^{g1}$ is independently H, halo or C$_{1-4}$ alkyl;
and with a mixture of (a) a transition metal catalyst; with or without (b) a phosphine ligand; (c) Base 3 selected from a Brønsted base and a Lewis base; and (d) a Zn salt; in Solvent 4 that is a protic, aprotic, polar, non-polar organic solvent or organic solvent mixture;
for a time and at a temperature sufficient for coupling to produce a compound of Formula (IV), or a tautomer, a stereoisomer, or a salt thereof.

In a 29th aspect, within the scope of the 28th aspect, the invention provides a method of making a compound of Formula (IV), or a tautomer, a stereoisomer, or a salt thereof; wherein:
R$^8$ is independently N—(R$^{e1}$)-pyrazolyl;
R$^{13}$ is halogen, —B(OH)$_2$, —BPin or —B(npg); and
R$^{e1}$ is independently Bn or

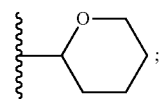;

comprising (1) contacting a compound of Formula (VI) or a tautomer, a stereoisomer, or a salt thereof; wherein R$^{16}$ is independently Cl or Br;
with a compound of Formula (VII) or a tautomer, a stereoisomer, or a salt thereof,
wherein: R$^{e1}$ is independently Bn or

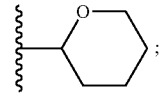;

and with a mixture of (a) a transition metal catalyst selected from Pd(Xantphos)Cl$_2$, Pd(DPEPhos)Cl$_2$, Pd(OAc)$_2$, and [(allyl)PdCl]$_2$; with or without (b) a phosphine ligand selected from Xantphos, DPEPhos, XPhos, PtBu$_3$HBF$_4$, AtaPhos, RuPhos, Cy-JohnPhos, Cy-DavePhos, DPP-DtBPF, PPh$_3$, P(fur)$_3$, PPh$_2$(o-anis), P(p-CF$_3$-Ph)$_3$, P(o-Tol)$_3$, PCy$_3$ HBF$_4$, PPh$_2$Pyr, PtBu$_2$Me HBF$_4$, AcaPhos, CX-ABn, S-Phos, JackiePhos, tB-Xantphos, DPPE, DCPP, DPPB, DCPB HBF$_4$, DPPPent, BISBI, DPPF, DCyPF, BiPHEP, and Cy-BIPHEP; (c) Base 3 selected from n-hexyllithium, n-octyllithium and n-butyllithium; and (d) a Zn salt selected from ZnCl$_2$, ZnBr$_2$, Zn(OPiv)$_2$, and Zn(OTf)$_2$; in Solvent 4 selected from Toluene, isopropanol, MTBE, CPME, THF, 2-Me-THF, MeOH, EtOH, n-BuOH, t-amyl alcohol, acetone, MEK, MIBK, MeCN, DMSO, EtOAc, IPAc, anisole, DMF, DCM, DCE, NMP, heptane, hexane, cyclohexane, and water, or a combination thereof;

for a time from 1 to 48 hours and at a temperature ranging from −78° C. to 80° C. sufficient for coupling to produce a compound of Formula (IV), or a tautomer, a stereoisomer, or a salt thereof.

In another aspect, within the scope of the 28th aspect, the invention provides a method of making a compound of Formula (IV) as defined in the 25th aspect, or a tautomer, a stereoisomer, or a salt thereof;

comprising (1) contacting a compound of Formula (VI) as defined in the 25th aspect, or a tautomer, a stereoisomer, or a salt thereof, with a compound of Formula (VII) as defined in the 25th aspect, or a tautomer, a stereoisomer, or a salt thereof;

and with a mixture of (a) a transition metal catalyst selected from Pd(Xantphos)Cl$_2$, Pd(DPEPhos)Cl$_2$, Pd (OAc)$_2$, and [(allyl)PdCl]$_2$; with or without (b) a phosphine ligand selected from Xantphos, DPEPhos, XPhos, PtBu$_3$HBF$_4$, AtaPhos, RuPhos, Cy-JohnPhos, Cy-DavePhos, DPP-DtBPF, PPh$_3$, P(fur)$_3$, PPh$_2$(o-anis), P(p-CF$_3$-Ph)$_3$, P(o-Tol)$_3$, PCy$_3$ HBF$_4$, PPh$_2$Pyr, PtBu$_2$Me HBF$_4$, AcaPhos, CX-ABn, S-Phos, JackiePhos, tB-Xantphos, DPPE, DCPP, DPPB, DCPB HBF$_4$, DPPPent, BISBI, DPPF, DCyPF, BiPHEP, and Cy-BIPHEP; (c) Base 3 selected from n-hexyllithium, n-octyllithium and n-butyllithium; and (d) a Zn salt selected from ZnCl$_2$ and ZnBr$_2$; in Solvent 4 selected from Toluene, isopropanol, MTBE, CPME, THF, 2-Me-THF, MeOH, EtOH, n-BuOH, t-amyl alcohol, acetone, MEK, MIBK, MeCN, DMSO, EtOAc, IPAc, anisole, DMF, DCM, DCE, NMP, heptane, hexane, cyclohexane, and water, or a combination thereof;

for a time from 1 to 48 hours and at a temperature ranging from −78° C. to 80° C. sufficient for coupling to produce a compound of Formula (IV), or a tautomer, a stereoisomer, or a salt thereof.

In a 30th aspect, the invention provides a method of making a compound of Formula (IVa), or a tautomer, a stereoisomer, or a salt thereof:

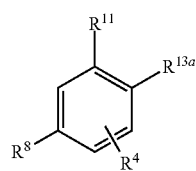
(IVa)

comprising (1) contacting a compound of Formula (VIb) or a tautomer, a stereoisomer, or a salt thereof:

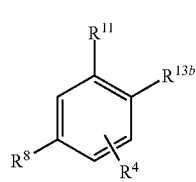
(VIb)

wherein R$^4$, R$^{11}$ and other variables are as defined as in any of the 1st to 3rd, 5th, 7th, 9th and 10th aspects;

R$^8$ is independently N—(R$^{e1}$)-pyrazolyl;
R$^{13a}$ is independently —B(OH)$_2$, —BPin, —B(npg) or —BF$_3$K;
R$^{13b}$ is independently halogen;
R$^{e1}$ is independently H, C(O)C$_{1-4}$ alkyl, —C(O)OC$_{1-4}$ alkyl,

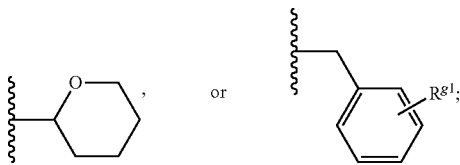

and
R$^{g1}$ is independently H, halo or C$_{1-4}$ alkyl;
and with a mixture of (a) a transition metal catalyst; with or without (b) a phosphine ligand; (c) Base 4 selected from a Brønsted base and a Lewis base; and (d) a borylation reagent; in Solvent 5 that is a protic, aprotic, polar, non-polar organic solvent or organic solvent mixture;

for a time and at a temperature sufficient for coupling to produce a compound of Formula (IVa), or a tautomer, a stereoisomer, or a salt thereof.

In a 31st aspect, within the scope of the 30th aspect, the invention provides a method of making a compound of Formula (IVa), or a tautomer, a stereoisomer, or a salt thereof;

comprising (1) contacting a compound of Formula (VIb) or a tautomer, a stereoisomer, or a salt thereof, and with a mixture of (a) a transition metal catalyst selected from [(allyl)PdCl]$_2$, [(cinnamyl)PdCl]$_2$, [(crotyl)PdCl]$_2$, PdCl$_2$(MeCN)$_2$, (XPhos) palladium(II) phenethylamine chloride, XPhos aminobiphenyl palladium chloride, XPhos aminobiphenyl palladium methanesulfonate, NiCl$_2$-6H$_2$O, Ni(NO$_3$)$_2$-6H$_2$O, and Ni(cod)$_2$; with or without (b) a phosphine ligand selected from XPhos, XPhosHBF$_4$, P(DMM-Ph)$_3$, CX-POMeCy, CX-A, DPEphos, Cy-JohnPhos, CPhos, CX-POMeCy, or CX-PCy; (c) Base 4 selected from KOPiv, NaOPiv, NaOAc, KOAc, or DIPEA; and (d) a borylation reagent selected from B$_2$(OH)$_4$, B$_2$(Pin)$_2$ or B$_2$(npg)$_2$; in Solvent 5 selected from MeOH, EtOH, MeTHF, and THF or a combination thereof;

for a time from 1 to 72 hours and at a temperature ranging from −10° C. to 50° C. for coupling to produce a compound of Formula (IVa), or a tautomer, a stereoisomer, or a salt thereof.

In another aspect, within the scope of the 30th aspect, the invention provides a method of making a compound of Formula (IVa), or a tautomer, a stereoisomer, or a salt thereof;

comprising (1) contacting a compound of Formula (VIb) or a tautomer, a stereoisomer, or a salt thereof, and with a mixture of (a) a transition metal catalyst selected from [(allyl)PdCl]$_2$, PdCl$_2$(MeCN)$_2$, NiCl$_2$-6H$_2$O, Ni(NO$_3$)$_2$-6H$_2$O, and Ni(cod)$_2$; with or without (b) a phosphine ligand selected from XPhos, P(DMM-Ph)$_3$, CX-POMeCy, CX-A, DPEphos, Cy-JohnPhos, CPhos, CX-POMeCy, or CX-PCy; (c) Base 4 selected from NaOPiv, KOAc, or DIPEA; and (d) a borylation reagent selected from B$_2$(OH)$_4$, B$_2$(Pin)$_2$ or B$_2$(npg)$_2$; in Solvent 5 selected from MeOH, EtOH, MeTHF, and THF or a combination thereof;

for a time from 1 to 48 hours and at a temperature ranging from 10° C. to 40° C. for coupling to produce a compound of Formula (IVa), or a tautomer, a stereoisomer, or a salt thereof.

In a 32nd aspect, the invention provides a compound of Formula (VIII), or a tautomer, a stereoisomer, or a salt thereof:

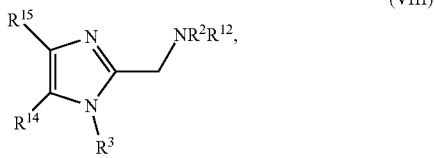

(VIII)

wherein $R^2$, $R^3$, $R^{12}$, and other variables are as defined as in any of the 1st to 3rd, 5th, 7th, 9th and 10th aspects;

$R^{14}$ is independently H, halogen, or —OS(O)$_2R^{b1}$;

$R^{15}$ is independently H, halogen, CN, CF$_3$, —C(O)NH$_2$, —C(NH)NH$_2$, —CH=NOH, —C(O)OR$^a$, or —C(O)SR$^a$;

$R^{b1}$ is independently C$_{1-4}$ alkyl, C$_{1-4}$ haloalkyl, or phenyl substituted with from 0 to 3 R$^{g2}$; and $R^{g2}$ is independently halo, C$_{1-4}$ alkyl, C$_{1-4}$ haloalkyl, C$_{1-4}$ alkoxy, or C$_{1-4}$ haloalkoxy.

In a 33rd aspect, within the scope of the 32nd aspect, the invention provides a compound of Formula (VIII), or a tautomer, a stereoisomer, or a salt thereof, wherein:

$R^{14}$ is independently H, Cl, Br, I, —OMs, —OTs, or —OTf; and $R^{15}$ is independently H, Cl, Br, I, CN, CF$_3$, or —C(O)NH$_2$.

In a 34th aspect, within the scope of the 32nd or 33rd aspect, the invention provides a compound of Formula (VIII), or a tautomer, a stereoisomer, or a salt thereof, wherein:

$R^{14}$ is independently H, Cl, Br, I, —OMs, —OTs, or —OTf; and $R^{15}$ is independently CN or CF$_3$.

In a 35th aspect, the invention provides a method of making a compound of Formula (V), or a tautomer, a stereoisomer, or a salt thereof:

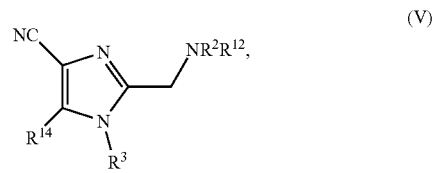

(V)

wherein $R^2$, $R^3$, $R^{12}$ and other variables are as defined as in any of the 1st to 3rd, 5th, 7th, 9th and 10th aspects;

$R^{14}$ is halogen;

comprising (1) contacting a compound of Formula (Va) or a tautomer, a stereoisomer, or a salt thereof:

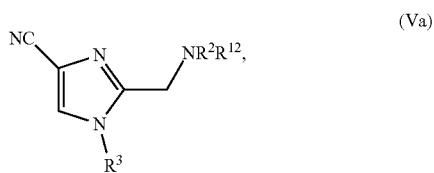

(Va)

wherein $R^2$, $R^3$, $R^{12}$ and other variables are as defined as in any of the 1st to 3rd, 5th, 7th, 9th and 10th aspects;

with a mixture of (a) an electrophilic halogenation reagent; with or without (b) a Brønsted base; and with or without (c) a Brønsted acid; in Solvent 6 a protic, aprotic, polar organic solvent, and water or a combination thereof;

for a time and at a temperature sufficient to produce a compound of Formula (V), or a tautomer, a stereoisomer, or a salt thereof.

In a 36th aspect, within the scope of the 35th aspect, the invention provides a method of making a compound of Formula (V), or a tautomer, a stereoisomer, or a salt thereof;

comprising (1) contacting a compound of Formula (Va) or a tautomer, a stereoisomer, or a salt thereof, with a mixture of (a) an electrophilic halogenation reagent selected from NCS, NBS, NIS, pyridinium hydrobromide perbromide, and I$_2$/PhI(OAc)$_2$ mixture; with or without (b) a Brønsted base selected from NaOAc, LiHMDS, DBU and pyridine; and with or without (c) AcOH; in Solvent 6 selected from MeOH, EtOH, IPA, MeCN, MTBE, DCM, EtOAc, water or a combination thereof;

for a time from 1 to 48 hours and at a temperature ranging from 0° C. to 80° C. sufficient to produce a compound of Formula (V), or a tautomer, a stereoisomer, or a salt thereof.

In a 37th aspect, within the scope of the 35th or 36th aspect, the invention provides a method of making a compound of Formula (V), or a tautomer, a stereoisomer, or a salt thereof;

comprising (1) contacting a compound of Formula (Va) or a tautomer, a stereoisomer, or a salt thereof;

with a mixture of (a) an electrophilic halogenation reagent selected from NCS, NBS, NIS, pyridinium hydrobromide perbromide, and I$_2$/PhI(OAc)$_2$ mixture; with (b) a Brønsted base selected from NaOAc, LiHMDS, DBU and pyridine; and followed by (c) AcOH; in Solvent 6 selected from MeOH, EtOH, IPA, MeCN, MTBE, DCM, EtOAc, water or a combination thereof;

for a time from 1 to 48 hours and at a temperature ranging from 0° C. to 80° C. sufficient to produce a compound of Formula (V), or a tautomer, a stereoisomer, or a salt thereof.

In a 38th aspect, the invention provides a method of making a compound of Formula (Va), or a tautomer, a stereoisomer, or a salt thereof:

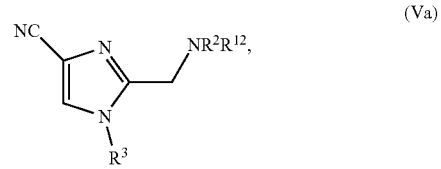

(Va)

wherein $R^2$, $R^3$, $R^{12}$ and other variables are as defined as in any of the 1st to 3rd, 5th, 7th, 9th and 10th aspects;

comprising (1) contacting a compound of Formula (XI) or a tautomer, a stereoisomer, or a salt thereof:

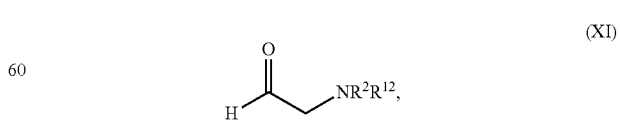

(XI)

wherein $R^2$, $R^{12}$ and other variables are as defined as in any of the 1st to 3rd, 5th, 7th, 9th and 10th aspects;

with a mixture of (a) a starting material selected from 3,3-dibromo-1,1,1-trifluoropropan-2-one, 3,3-dibromo-1,1, 1-trifluoropropan-2-one hydrate, 3,3-dichloro-1,1,1-trifluoropropan-2-one, 3,3-dichloro-1,1,1-trifluoropropan-2-one hydrate, trifluoropyruvaldehyde and 3,3,3-trifluoro-2,2-dihydroxy-propanal; (b) aqueous ammonium hydroxide, ammonium chloride, ammonium bromide, ammonium fluoride, ammonium iodide, ammonium acetate, ammonium carbonate, ammonium dihydrogenphosphate, ammonium phosphate dibasic, ammonium formate, ammonium hydrogensulfate, and ammonium sulfate; with or without (c) AcOH or NH$_4$OAc; and with or without (d) Base 5 selected from K$_3$PO$_4$, Na$_3$PO$_4$, LiOH, NaOH, KOH, and CsOH; in Solvent 7 selected from IPA, MeOH, EtOH, THF, MTBE, CPME, nBuOAc and water or a combination thereof;

for a time and at a temperature sufficient to produce a compound of Formula (Va), or a tautomer, a stereoisomer, or a salt thereof.

In another aspect, the invention provides a method of making a compound of Formula (Va) as defined in the 38th aspect, or a tautomer, a stereoisomer, or a salt thereof;

comprising (1) contacting a compound of Formula (XI) as defined in the 34th aspect, or a tautomer, a stereoisomer, or a salt thereof, with a mixture of (a) a starting material selected from 3,3-dibromo-1,1,1-trifluoropropan-2-one, 3,3-dibromo-1,1,1-trifluoropropan-2-one hydrate, 3,3-dichloro-1,1,1-trifluoropropan-2-one, 3,3-dichloro-1,1,1-trifluoropropan-2-one hydrate, trifluoropyruvaldehyde and 3,3,3-trifluoro-2,2-dihydroxy-propanal; (b) aqueous ammonium hydroxide; with or without (c) AcOH or NH$_4$OAc; and with or without (d) Base 5 selected from K$_3$PO$_4$, Na$_3$PO$_4$, LiOH, NaOH, KOH, and CsOH; in Solvent 7 selected from IPA, MeOH, EtOH, THF, MTBE, CPME, nBuOAc and water or a combination thereof;

for a time and at a temperature sufficient to produce a compound of Formula (Va), or a tautomer, a stereoisomer, or a salt thereof.

In a 39th aspect, within the scope of the 38th aspect, the invention provides a method of making a compound of Formula (Va), or a tautomer, a stereoisomer, or a salt thereof;

comprising (1) contacting a compound of Formula (XI) or a tautomer, a stereoisomer, or a salt thereof, with a mixture of (a) a starting material selected from 3,3-dibromo-1,1,1-trifluoropropan-2-one, 3,3-dibromo-1,1,1-trifluoropropan-2-one hydrate, 3,3-dichloro-1,1,1-trifluoropropan-2-one, 3,3-dichloro-1,1,1-trifluoropropan-2-one hydrate, trifluoropyruvaldehyde and 3,3,3-trifluoro-2,2-dihydroxy-propanal; (b) aqueous ammonium hydroxide, ammonium chloride, ammonium bromide, ammonium fluoride, ammonium iodide, ammonium acetate, ammonium carbonate, ammonium dihydrogenphosphate, ammonium phosphate dibasic, ammonium formate, ammonium hydrogensulfate, and ammonium sulfate; with (c) AcOH or NH$_4$OAc; and followed by (d) Base 5 selected from K$_3$PO$_4$, Na$_3$PO$_4$, LiOH, NaOH, KOH, and CsOH; in Solvent 7 selected from IPA, MeOH, EtOH, THF, MTBE, CPME, nBuOAc and water or a combination thereof;

for a time and at a temperature sufficient to produce a compound of Formula (Va), or a tautomer, a stereoisomer, or a salt thereof.

In another aspect, within the scope of the 39th aspect, the invention provides a method of making a compound of Formula (Va), or a tautomer, a stereoisomer, or a salt thereof;

comprising (1) contacting a compound of Formula (XI) or a tautomer, a stereoisomer, or a salt thereof, with a mixture of (a) a starting material selected from 3,3-dibromo-1,1,1-trifluoropropan-2-one, 3,3-dibromo-1,1,1-trifluoropropan-2-one hydrate, 3,3-dichloro-1,1,1-trifluoropropan-2-one, 3,3-dichloro-1,1,1-trifluoropropan-2-one hydrate, trifluoropyruvaldehyde and 3,3,3-trifluoro-2,2-dihydroxy-propanal; (b) aqueous ammonium hydroxide; with (c) AcOH or NH$_4$OAc; and followed by (d) Base 5 selected from K$_3$PO$_4$, Na$_3$PO$_4$, LiOH, NaOH, KOH, and CsOH; in Solvent 7 selected from IPA, MeOH, EtOH, THF, MTBE, CPME, nBuOAc and water or a combination thereof;

for a time and at a temperature sufficient to produce a compound of Formula (Va), or a tautomer, a stereoisomer, or a salt thereof.

In a 40th aspect, the invention provides a method of making a compound of Formula (V), or a tautomer, a stereoisomer, or a salt thereof:

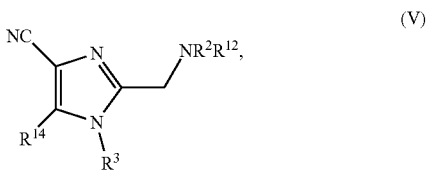

wherein $R^2$, $R^3$, $R^{12}$ and other variables are as defined as in any of the 1st to 3rd, 5th, 7th, 9th and 10th aspects;

$R^{14}$ is halogen;

comprising (1) contacting a compound of Formula (XI) or a tautomer, a stereoisomer, or a salt thereof:

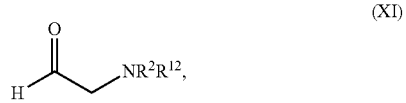

wherein $R^2$, $R^{12}$ and other variables are as defined as in any of the 1st to 3rd, 5th, 7th, 9th and 10th aspects;

with a mixture of (a) glyoxal or glyoxal hydrate; (b) aqueous ammonium hydroxide, ammonium chloride, ammonium bromide, ammonium fluoride, ammonium iodide, ammonium acetate, ammonium carbonate, ammonium dihydrogenphosphate, ammonium phosphate dibasic, ammonium formate, ammonium hydrogensulfate, and ammonium sulfate; with or without (c) AcOH or NH$_4$OAc; in Solvent 8 selected from MeOH, EtOH, IPA, n-propanol, n-butanol, MTBE, CPME, nBuOAc, and water or a combination thereof;

for a time and at a temperature sufficient to produce a compound of Formula (Vb), or a tautomer, a stereoisomer, or a salt thereof:

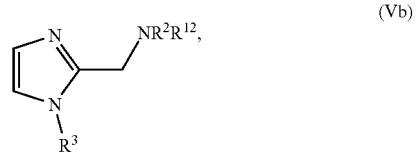

wherein $R^2$, $R^3$, $R^{12}$ and other variables are as defined as in any of the 1st to 3rd, 5th, 7th, 9th and 10th aspects;

and (2) contacting the compound of (Vb), or a tautomer, a stereoisomer, or a salt thereof;

with a mixture of (a) NIS or I2; with or without (b) NaOAc, NaHCO$_3$, or KHCO$_3$; in Solvent 8 selected from MeOH, EtOH, IPA, n-propanol, n-butanol, water or a combination thereof;

for a time and at a temperature sufficient to produce a compound of Formula (Vc), or a tautomer, a stereoisomer, or a salt thereof:

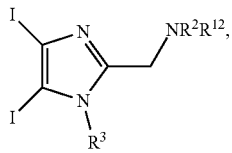

(Vc)

wherein $R^2$, $R^3$, and $R^{12}$ and other variables are as defined as in any of the 1st to 3rd, 5th, 7th, 9th and 10th aspects;

and (3) contacting the compound of (Vc), or a tautomer, a stereoisomer, or a salt thereof;

with a mixture of (a) an electrophilic cyanation reagent; (b) a Grignard reagent; in Solvent 10 that is an aprotic organic solvent or its organic solvent mixture;

for a time and at a temperature sufficient to produce the compound of Formula (V), or a tautomer, a stereoisomer, or a salt thereof.

In another aspect, the invention provides a method of making a compound of Formula (V) as defined in the 40th aspect, or a tautomer, a stereoisomer, or a salt thereof;

comprising (1) contacting a compound of Formula (XI) as defined in the 37th aspect, or a tautomer, a stereoisomer, or a salt thereof, with a mixture of (a) glyoxal or glyoxal hydrate; (b) aqueous ammonium hydroxide; with or without (c) AcOH or $NH_4OAc$; in Solvent 8 selected from MeOH, EtOH, IPA, n-propanol, n-butanol, MTBE, CPME, nBuOAc, and water or a combination thereof;

for a time and at a temperature sufficient to produce a compound of Formula (Vb) as defined in the 37th aspect, or a tautomer, a stereoisomer, or a salt thereof;

and (2) contacting the compound of (Vb), or a tautomer, a stereoisomer, or a salt thereof;

with a mixture of (a) NIS or $I_2$; with or without (b) NaOAc, $NaHCO_3$, or $KHCO_3$; in Solvent 8 selected from MeOH, EtOH, IPA, n-propanol, n-butanol, water or a combination thereof;

for a time and at a temperature sufficient to produce a compound of Formula (Vc) as defined in the 37th aspect, or a tautomer, a stereoisomer, or a salt thereof;

and (3) contacting the compound of (Vc), or a tautomer, a stereoisomer, or a salt thereof;

with a mixture of (a) an electrophilic cyanation reagent; (b) a Grignard reagent; in Solvent 10 that is an aprotic organic solvent or its organic solvent mixture;

for a time and at a temperature sufficient to produce the compound of Formula (V), or a tautomer, a stereoisomer, or a salt thereof.

In a 41st aspect, within the scope of the 40th aspect, the invention provides a method of making a compound of Formula (V), or a tautomer, a stereoisomer, or a salt thereof;

comprising (1) contacting a compound of Formula (XI) or a tautomer, a stereoisomer, or a salt thereof, with a mixture of (a) glyoxal or glyoxal hydrate; (b) aqueous ammonium hydroxide, ammonium chloride, ammonium bromide, ammonium fluoride, ammonium iodide, ammonium acetate, ammonium carbonate, ammonium dihydrogenphosphate, ammonium phosphate dibasic, ammonium formate, ammonium hydrogensulfate, and ammonium sulfate; with or without (c) AcOH or $NH_4OAc$; in Solvent 7 selected from MeOH, EtOH, IPA, n-propanol, n-butanol, MTBE, CPME, nBuOAc, and water or a combination thereof;

for a time from 1 h to 96 hours and at a temperature ranging from 0° C. to 80° C. to produce a compound of Formula (Vb), or a tautomer, a stereoisomer, or a salt thereof;

and (2) contacting the compound of (Vb), or a tautomer, a stereoisomer, or a salt thereof;

with a mixture of (a) NIS or $I_2$; with or without (b) NaOAc, $NaHCO_3$, or $KHCO_3$; in Solvent 8 selected from MeOH, EtOH, IPA, n-propanol, n-butanol, water or a combination thereof;

for a time from 5 min to 48 hours and at a temperature ranging from 0° C. to 80° C. sufficient to produce a compound of Formula (Vc), or a tautomer, a stereoisomer, or a salt thereof;

and (3) contacting the compound of (Vc), or a tautomer, a stereoisomer, or a salt thereof;

with a mixture of (a) an electrophilic cyanation reagent selected from 1H-imidazole-1-carbonitrile, 1H-Benzotriazole-1-carbonitrile, and phenyl cyanate; (b) a Grignard reagent selected from isopropylmagnesium chloride lithium chloride complex, sec-butylmagnesium chloride lithium chloride complex, isopropylmagnesium bromide, isopropylmagnesium chloride, ethylmagnesium bromide, and methylmagnesium bromide; in Solvent 10 selected from THF, 2-Me-THF, MTBE, CPME, and IPAc or a combination thereof;

for a time from 5 min to 48 hours and at a temperature ranging from −20° C. to 80° C. sufficient to produce the compound of Formula (V), or a tautomer, a stereoisomer, or a salt thereof.

In another aspect, within the scope of the 41st aspect, the invention provides a method of making a compound of Formula (V), or a tautomer, a stereoisomer, or a salt thereof;

comprising (1) contacting a compound of Formula (XI) or a tautomer, a stereoisomer, or a salt thereof, with a mixture of (a) glyoxal or glyoxal hydrate; (b) aqueous ammonium hydroxide; with or without (c) AcOH or $NH_4OAc$; in Solvent 7 selected from MeOH, EtOH, IPA, n-propanol, n-butanol, MTBE, CPME, nBuOAc, and water or a combination thereof;

for a time from 5 h to 48 hours and at a temperature ranging from 0° C. to 80° C. to produce a compound of Formula (Vb), or a tautomer, a stereoisomer, or a salt thereof;

and (2) contacting the compound of (Vb), or a tautomer, a stereoisomer, or a salt thereof;

with a mixture of (a) NIS or $I_2$; with or without (b) NaOAc, $NaHCO_3$, or $KHCO_3$; in Solvent 8 selected from MeOH, EtOH, IPA, n-propanol, n-butanol, water or a combination thereof;

for a time from 5 min to 48 hours and at a temperature ranging from 0° C. to 80° C. sufficient to produce a compound of Formula (Vc), or a tautomer, a stereoisomer, or a salt thereof;

and (3) contacting the compound of (Vc), or a tautomer, a stereoisomer, or a salt thereof;

with a mixture of (a) an electrophilic cyanation reagent selected from 1H-1H-Benzotriazole-1-carbonitrile, and phenyl cyanate; (b) a Grignard reagent selected from isopropylmagnesium chloride lithium chloride complex, sec-butylmagnesium chloride lithium chloride complex, isopropylmagnesium bromide, isopropylmagnesium chloride, ethylmagnesium bromide, and methylmagnesium bromide; in Solvent 10 selected from THF, 2-Me-THF, MTBE, CPME, and IPAc or a combination thereof;

for a time from 5 min to 48 hours and at a temperature ranging from −20° C. to 80° C. sufficient to produce the compound of Formula (V), or a tautomer, a stereoisomer, or a salt thereof.

In a 42nd aspect, the invention provides a method of making a compound of Formula (Va), or a tautomer, a stereoisomer, or a salt thereof:

$$\text{(Va)}$$

[Structure showing: NC-substituted imidazole with NR²R¹² and R³ groups]

wherein $R^2$, $R^3$, $R^{12}$ and other variables are as defined as in any of the 1st to 3rd, $5^{th}$, 7th, 9th and 10th aspects;

comprising (1) contacting a compound of Formula (XI) or a tautomer, a stereoisomer, or a salt thereof:

$$\text{(XI)}$$

[Structure showing: aldehyde with NR²R¹² group]

wherein $R^2$, $R^{12}$ and other variables are as defined as in any of the 1st to 3rd, $5^{th}$, 7th, 9th and 10th aspects;

with a mixture of (a) a starting material selected from 3,3-dibromo-1,1,1-trifluoropropan-2-one, 3,3-dibromo-1,1,1-trifluoropropan-2-one hydrate, 3,3-dichloro-1,1,1-trifluoropropan-2-one, 3,3-dichloro-1,1,1-trifluoropropan-2-one hydrate, trifluoropyruvaldehyde and 3,3,3-trifluoro-2,2-dihydroxy-propanal; (b) aqueous ammonium hydroxide, ammonium chloride, ammonium bromide, ammonium fluoride, ammonium iodide, ammonium acetate, ammonium carbonate, ammonium dihydrogenphosphate, ammonium phosphate dibasic, ammonium formate, ammonium hydrogensulfate, and ammonium sulfate; with or without (c) AcOH or NH₄OAc; and with or without (d) Base 5 selected from K₃PO₄, Na₃PO₄, LiOH, NaOH, KOH, and CsOH; in Solvent 7 selected from IPA, MeOH, EtOH, THF, MTBE, CPME, nBuOAc and water or a combination thereof;

for a time and at a temperature sufficient to produce a compound of Formula (Vd), or a tautomer, a stereoisomer, or a salt thereof;

$$\text{(Vd)}$$

[Structure showing: F₃C-substituted imidazole with NR²R¹² and R³ groups]

wherein $R^2$, $R^3$, $R^{12}$ and other variables are as defined as in any of the 1st to 3rd, 5th, 7th, 9th and 10th aspects;

and (2) contacting a compound of Formula (Vd) or a tautomer, a stereoisomer, or a salt thereof, with a mixture of (a) aqueous ammonium hydroxide, ammonium chloride, ammonium bromide, ammonium fluoride, ammonium iodide, ammonium acetate, ammonium carbonate, ammonium dihydrogenphosphate, ammonium phosphate dibasic, ammonium formate, ammonium hydrogensulfate, and ammonium sulfate; with or without (b) Base 6 selected from K₃PO₄, Na₃PO₄, LiOH, NaOH, KOH, and CsOH; in Solvent 8 selected from IPA, MeOH, EtOH, THF, MTBE, CPME, nBuOAc and water or a combination thereof;

for a time and at a temperature sufficient to produce a compound of Formula (Va), or a tautomer, a stereoisomer, or a salt thereof.

In a 43rd aspect, the invention provides a method of preparing Compound 1, or a tautomer, or a salt thereof:

Compound 1

[Structure of Compound 1]

comprising 1) contacting a compound of Compound 2, or a tautomer, or a salt thereof, wherein:

Compound 2

[Structure of Compound 2]

with a mixture of an acylation reagent, with Base 7 selected from organic and inorganic bases, in Solvent 9 that is a protic, aprotic or polar organic solvent, water or the solvent mixture;

for a time and at a temperature sufficient for acylation and to produce Compound 1 and its over-acetylated derivatives;

followed by treating the reaction mixture with or without Base 8 selected from organic and inorganic bases in Solvent 9;

for a time at a temperature sufficient to convert its over-acetylated derivatives to Compound 1; and 2) the reaction mixture is treated with acetic acid to adjust pH to 7.0-12.5 to crystallize in sufficient yield and control crystal form produce Compound 1, or a tautomer, a stereoisomer, or a salt thereof.

In a 44th aspect, comprising 1) and 2) in the 43rd aspect, further 3) drying Compound 1 at humidity, temperature, and pressure controlled conditions sufficient to remove residual solvent, water and maintain crystalline Form A without over dehydration.

In a 45th aspect, within the scope of the 43rd aspect; comprising 1) contacting a compound of Compound 2, or a tautomer, or a salt thereof, with a mixture of an acylation reagent selected from acetic anhydride, acetyl chloride, 1-acetylimidazole, 2,2,2-trifluoroethyl acetate, 1-(trifluoromethyl)vinyl acetate, pentafluoro-2-propenyl acetate, and 1,1,1-trichloroacetone, with Base 7 selected from selected from N-Me-pyrrolidine, diisopropylethylamine, tert-butyl-tetramethylguanidine, 1,8-Diazabicyclo(5.4.0)undec-7-ene, 1,5-Diazabicyclo[4.3.0]non-5-ene, N-Me-piperidine, dimethylisopropylamine, dimethylpiperazine, 2-Me-pyridine, N-Me-imidazole, 2,6-lutidine, triethylamine, 4-Me-morpholine, tetramethylguanidine, dimethylethylamine, tetramethylethylenediamine, aqueous NaOH, aqueous KOH, and aqueous LiOH, aqueous $Bu_4NOH$, aqueous $Et_4NOH$, aqueous $Na_2CO_3$, aqueous $K_2CO_3$, quinuclidine, tris(hydroxymethyl)aminomethane, and aqueous $K_2HPO_4$, in Solvent 9 selected from water, NMP, DMAc, DMF, THF, IPA, $CH_3CN$, MeOH, EtOH, or the solvent mixture;

for a time 5 min to 8 h and at a temperature of 0 to 50° C. sufficient for acylation and to produce Compound 1 and its over-acetylated derivatives;

followed by treating the reaction mixture with or without Base 8 selected from ethylenediamine, N,N-dimethylethylenediamine, NA'-dimethylethylenediamine, ethanolamine, n-butylamine, 1,3-diamino propane, isopropylamine, 2-hydroxymethylpiperidine, benzylmethylamine, 3-dimethylamino-1-propylamine, N-Methyl piperidine, cyclohexylamine, diethanolamine, diethylamine, hexamethyleneimine, morpholine, N-ethyl ethanolamine, piperazine, thiamorpholine, tert-butyl-tetramethylguanidine, 1-(3-aminopropyl)hexahydro-2H-azepin-2-one, aqueous NaOH, aqueous KOH, aqueous LiOH, aqueous $NH_4OH$, aqueous $Bu_4NOH$, and aqueous $Et_4NOH$, in Solvent 9;

for a time of 30 min to 48 h at a temperature of 10 to 70° C. sufficient to convert its over-acetylated derivatives to Compound 1; and 2) the reaction mixture is treated with acetic acid to adjust pH to 7.0-12.5 to crystallize in sufficient yield and control crystal form produce Compound 1, or a tautomer, a stereoisomer, or a salt thereof.

In a 46th aspect, comprising 1) and 2) in the 43rd aspect, further 3) drying Compound 1 at a humidity of 5% RH to 100% RH, temperature of 10 to 60° C., and pressure of 100 mbar to atmosphere pressure, sufficient to remove residual solvent, water and maintain crystalline Form A without over dehydration.

In a 47th aspect, the invention provides a compound having the following formula:

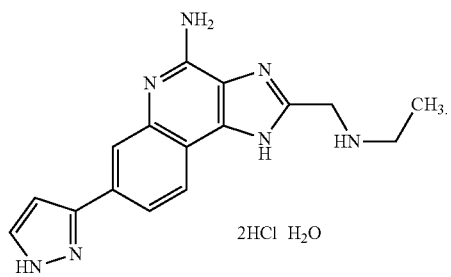 [SMILES: CCNCc1nc2c(N)nc3cc(-c4cc[nH]n4)ccc3c2[nH]1 ; O]

2HCl H₂O

In a 48th aspect, the invention provides a compound having the following formula:

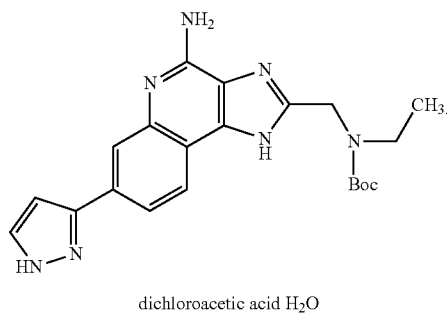 [SMILES: CCN(Cc1nc2c(N)nc3cc(-c4cc[nH]n4)ccc3c2[nH]1)C(=O)OC(C)(C)C ; "dichloroacetic acid H2O"]

dichloroacetic acid H₂O

In another aspect, the invention provides a method of making a compound of Formula (I), or a tautomer, a stereoisomer, or a salt thereof, wherein all variables are as defined as in any of the 1st to 3rd, 5th and 7th aspects;
comprising step (1) of any of the 20th to 24th aspects;
then step (1) and (2) of any of the 1st to 8th aspects.

In another aspect, the invention provides a method of making a compound of Formula (I), or a tautomer, a stereoisomer, or a salt thereof, wherein all variables are as defined as in any of the 1st to 5th aspects;
comprising step (1) of any of the 28th to 29th;
step (1) of any of the 20th to 24th aspects;
then step (1) and (2) of any of the 1st to 8th aspects.

In another aspect, the invention provides a method of preparing Compound 1, or a tautomer, or a salt thereof:

Compound 1

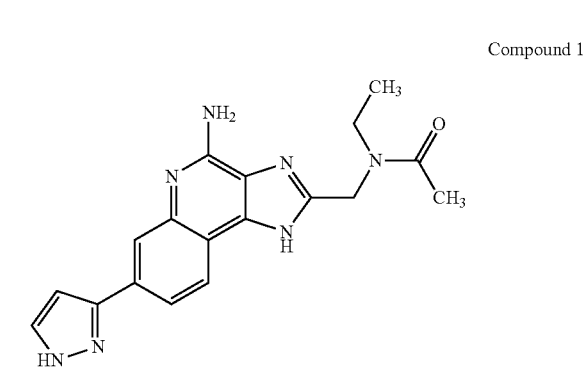 [SMILES: CCN(Cc1nc2c(N)nc3cc(-c4cc[nH]n4)ccc3c2[nH]1)C(C)=O]

comprising contacting a compound of Compound 2, or a tautomer, or a salt thereof, wherein:

Compound 2

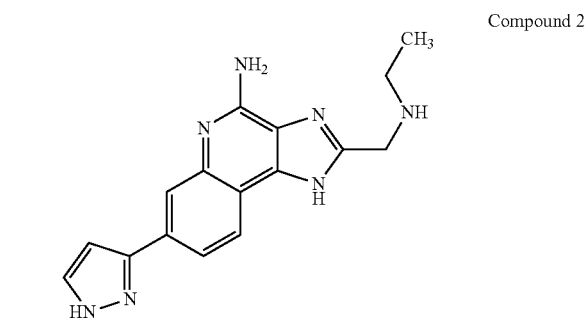 [SMILES: CCNCc1nc2c(N)nc3cc(-c4cc[nH]n4)ccc3c2[nH]1]

with acetic anhydride and DBU in water to promote acylation;

and acetic acid to adjust pH to 8.5-12.5 to crystallize Compound 1 in sufficient yield and control crystal form to produce Compound 1, or a tautomer, a stereoisomer, or a salt thereof.

The names used herein to characterize a specific form, e.g., "Form A" etc., are merely identifiers that are to be interpreted in accordance with the characterization information presented herein and are not to be limited so as to exclude any other substance possessing similar or identical physical and chemical characteristics.

All numbers expressing quantities of ingredients, weight percentages, temperatures, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

All measurements are subject to experimental error and are within the spirit of the invention.

N-[[4-amino-7-(1H-pyrazol-3-yl)-1H-imidazo[4,5-c]quinolin-2-yl]methyl]-N-ethylacetamide, also referred to herein as Compound 1, has the below structure:

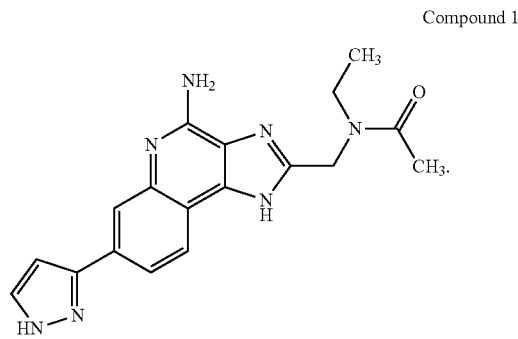 [SMILES: CCN(Cc1nc2c(N)nc3cc(-c4cc[nH]n4)ccc3c2[nH]1)C(C)=O]

Compound 1

Compound 1 is a modulator of NLRP3 and is being investigated as a treatment for cancer and other diseases. Compound 1 has been previously described in U.S. patent application Ser. No. 15/898,258 filed Feb. 16, 2018.

The disclosure is directed to solid forms of Compound 1, for example, Form A of Compound 1 (monohydrate), and Form B of Compound 1 (dehydrated), as well as the production of such solid forms, pharmaceutical compositions comprising such solid forms, and methods of treating diseases mediated by NLRP3 using such solid forms. Designations of the disclosed solid forms should not be construed as limiting with respect to any other substance possessing similar or identical physical and chemical characteristics, but rather, it should be understood that these designations are identifiers that should be interpreted according to the characterization information disclosed herein.

TABLE 1

Solid Forms of Compound 1

| Compound 1 | Form |
| --- | --- |
| Monohydrate | A |
| Dehydrated | B |

Form A of Compound 1

In one embodiment, the disclosure is directed a solid form of Compound 1 monohydrate. For example, the solid form of Compound 1 monohydrate comprises about 1 molecule of water per molecule of Compound 1.

In a preferred aspects, the solid form of Compound 1 hydrate is a crystalline form of Compound 1 monohydrate, referred to herein as Form A. The Form A of Compound 1 has a desirable stability profile.

Table 2 sets forth the single crystal X-ray data for the Form A of Compound 1.

TABLE 2

Single Crystal X-Ray Data for the Form A

| Temperature | room temperature |
| --- | --- |
| Crystal system, space group (sg) | $P2_1/c$ |
| Unit cell dimensions | a = 5.18 ± 0.05Å alpha = 90° |
| | b = 12.42 ± 0.05Å beta = 91.5 ± 0.5° |
| | c = 27.71 ± 0.05Å gamma = 90° |
| Volume (V) | 1781 ± 10Å$^3$ |
| Calculated density ($D_{calc}$) | 1.370 g/cm$^3$ |
| Molecules per unit cell (Z) | 4 |

In one embodiment, the Form A of Compound 1 is characterized by an X-ray diffraction pattern substantially as depicted in FIG. 1.

Diffraction peak positions for the Form A, at room temperature, based on a high quality pattern collected with a diffractometer (CuKα) with a spinning capillary with 2θ calibrated with a NIST, or other suitable standard, are shown in Table 3.

TABLE 3

Characteristic diffraction peak positions for the Form A

| degrees 2θ ± 0.2 |
| --- |
| 7.8 |
| 9.6 |
| 12.8 |
| 14.6 |
| 17.5 |
| 27.7 |
| 28.3 |

The Form A of Compound 1 can be characterized by an X-ray diffraction pattern having one peak, or at least one peak, selected from 7.8, 9.6, 12.8, 14.6, 17.5, 27.7, and 28.3 (the values listed in Table 1) degrees 2θ±0.2 degrees 2θ. The Form A can also be characterized by an X-ray diffraction pattern having two peaks selected from the values listed in Table 3. The Form A can also be characterized by an X-ray diffraction pattern having three peaks selected from the values listed in Table 3. The Form A can also be characterized by an X-ray diffraction pattern having four peaks selected from the values listed in Table 3. The Form A can also be characterized by an X-ray diffraction pattern having five peaks selected from the values listed in Table 3. The Form A can also be characterized by an X-ray diffraction pattern having six peaks selected from the values listed in Table 3. Compound 1 free base monohydrate Form A can also be characterized by an X-ray diffraction pattern having peaks at 7.8, 9.6, 12.8, 14.6, 17.5, 27.7, and 28.3 degrees 2θ±0.2 degrees 2θ.

Figure 3:
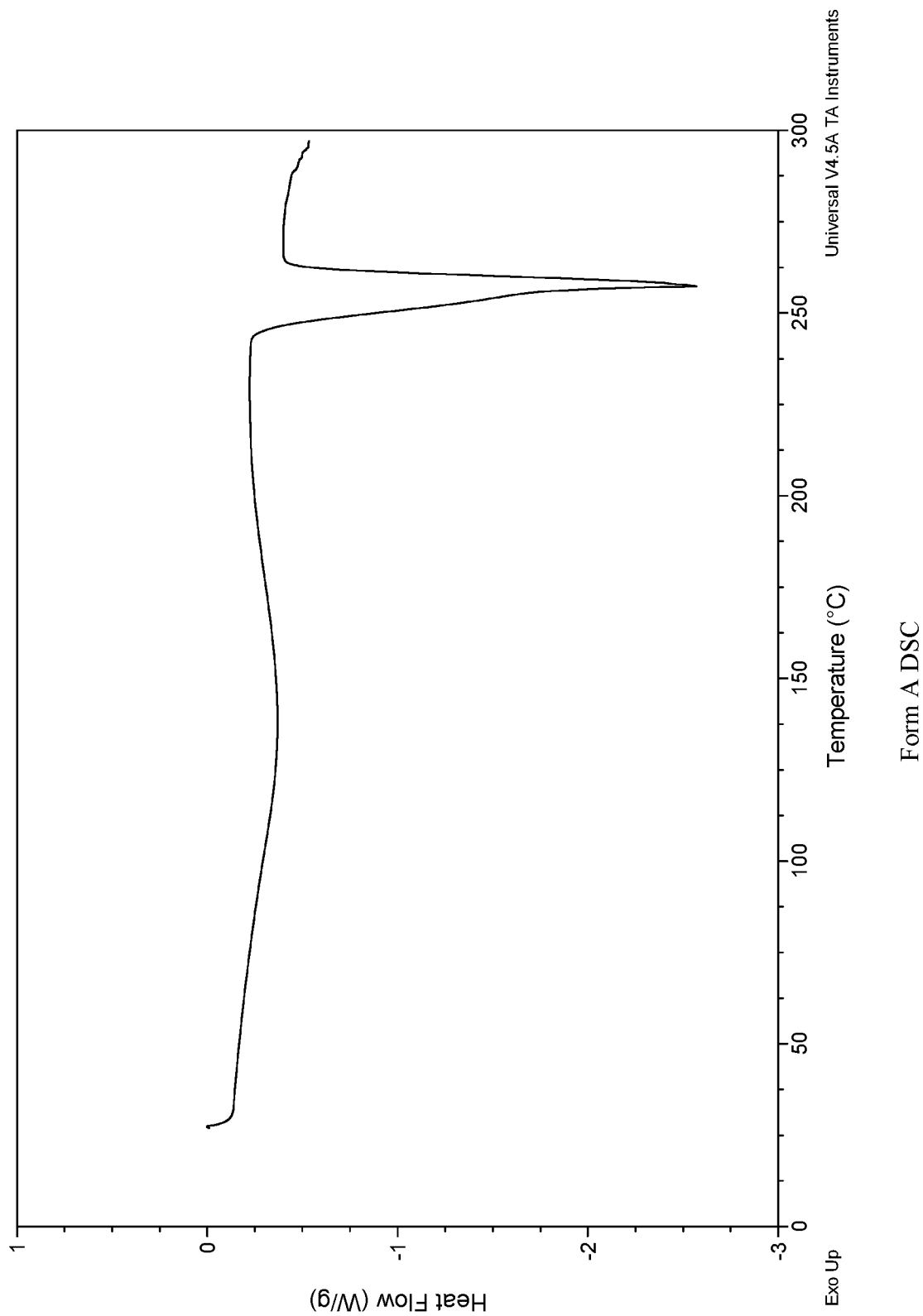
FIG. 3 depicts a differential scanning calorimetry (DSC) thermogram of Form A of Compound 1.

In one embodiment, the Form A of Compound 1 is characterized by a DSC thermogram substantially in accordance with that shown in FIG. 3.

In one embodiment, the Form A of Compound 1 is characterized by a TGA thermogram having weight loss of about 5 wt. %, based on the weight of the sample of the Form A, upon being heated to a temperature up to 225° C.

Figure 4:
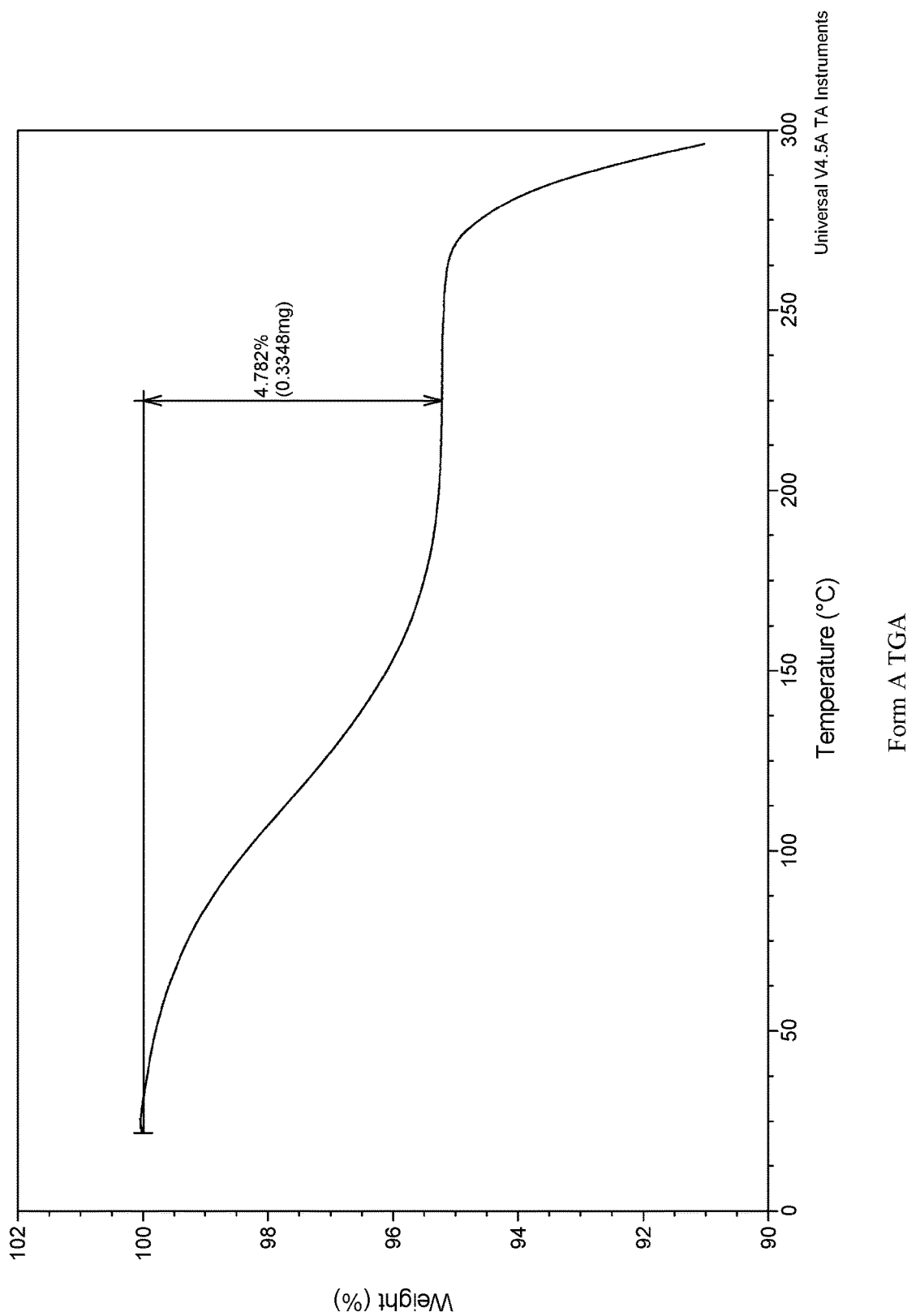
FIG. 4 depicts a thermogravimetric analysis (TGA) thermogram of Form A of Compound 1.
Figure 5:
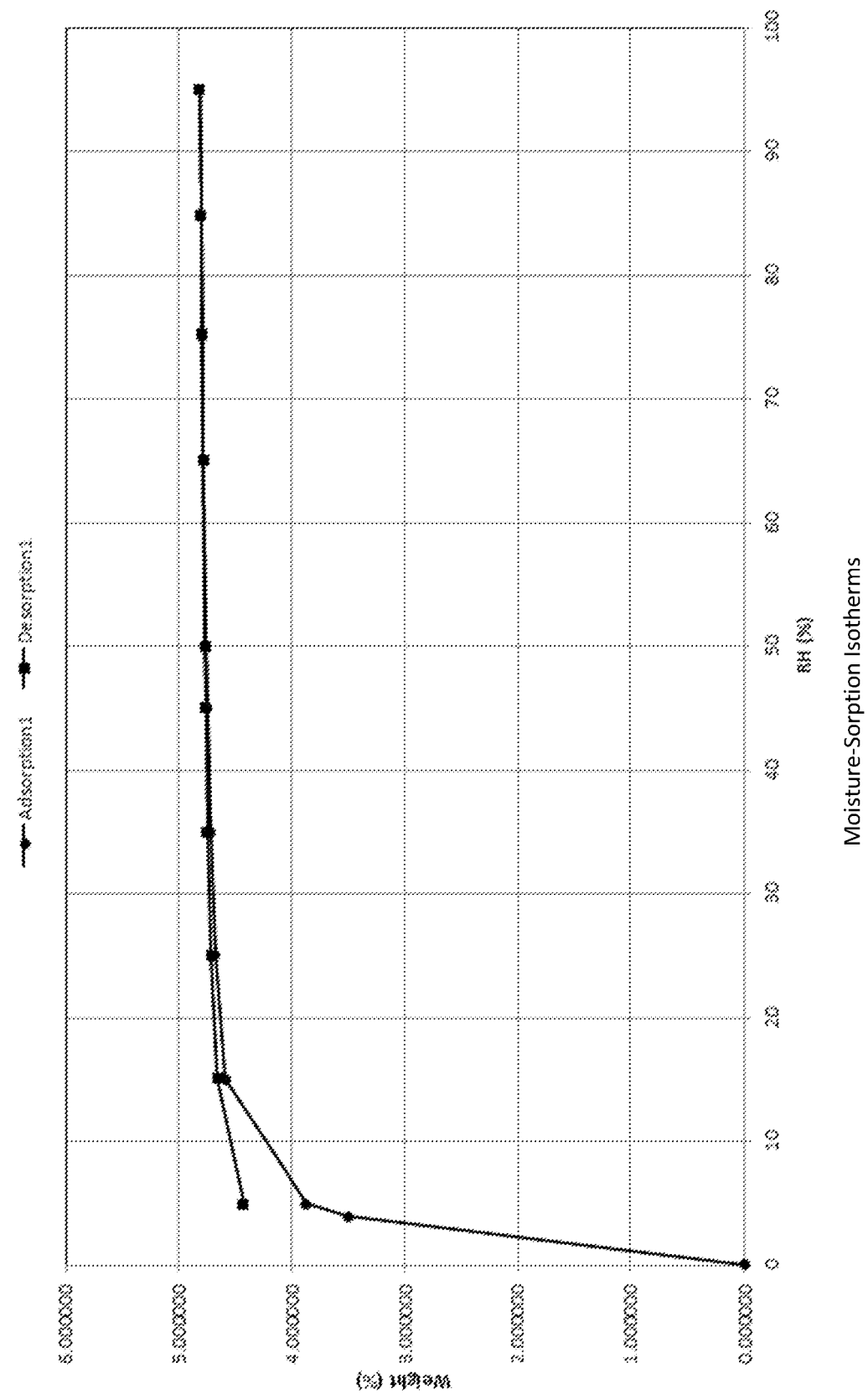
FIG. 5 depicts moisture-sorption isotherms of solid forms of Compound 1.

In one embodiment, the Form A exhibits a TGA thermogram substantially the same as shown in FIG. 4.

DSC data of the Form A of Compound 1 displays a broad endotherm was observed in the range ca. room temperature to 225° C. which corresponds to dehydration of the Form A of Compound 1, as observed in the TGA.

The Form A can be in substantially pure form, that is, having a purity of about 90% or greater, based on the weight of the compound, as determined by HPLC (High Performance Liquid Chromatography). For example, the Form A can have a purity of about 90, 91, 92, 93, 94, 95, 96, 97, 98, 99, or 100%. The remaining material can comprise other solid forms of Compound 1 and/or reaction impurities and/or processing impurities arising from its preparation.

Mixtures of the Form A of Compound 1 with other solid forms of Compound 1 are also within the scope of the disclosure. In these embodiments, such mixtures can comprise less than 90%, based on the weight of the mixture, of the Form A of Compound 1. For example, mixtures can comprise 85, 80, 75, 70, 65, 60, 55, 50, 45, 40, 35, 30, 25, 20, 15, 10, or about 5%, by weight of the mixture, of the Form A.

Form B of Compound 1

In one embodiment, the disclosure is directed to a crystalline dehydrated state of Compound 1, referred to herein as Form B.

Table 4 sets forth the single crystal X-ray data for the Form B of Compound 1.

TABLE 4

| Single Crystal X-Ray Data for the Form B | |
|---|---|
| Temperature | room temperature |
| Crystal system, space group (sg) | P2$_1$/c |
| Unit cell dimensions | a = 4.80 ± 0.05Å alpha = 90° |
| | b = 13.00 ± 0.05Å beta = 90.7 ± 0.5° |
| | c = 27.99 ± 0.05Å gamma = 90° |
| Volume (V) | 1747 ± 10Å$^3$ |
| Calculated density (D$_{calc}$) | 1.328 g/cm$^3$ |
| Molecules per unit cell (Z) | 4 |

Figure 2:
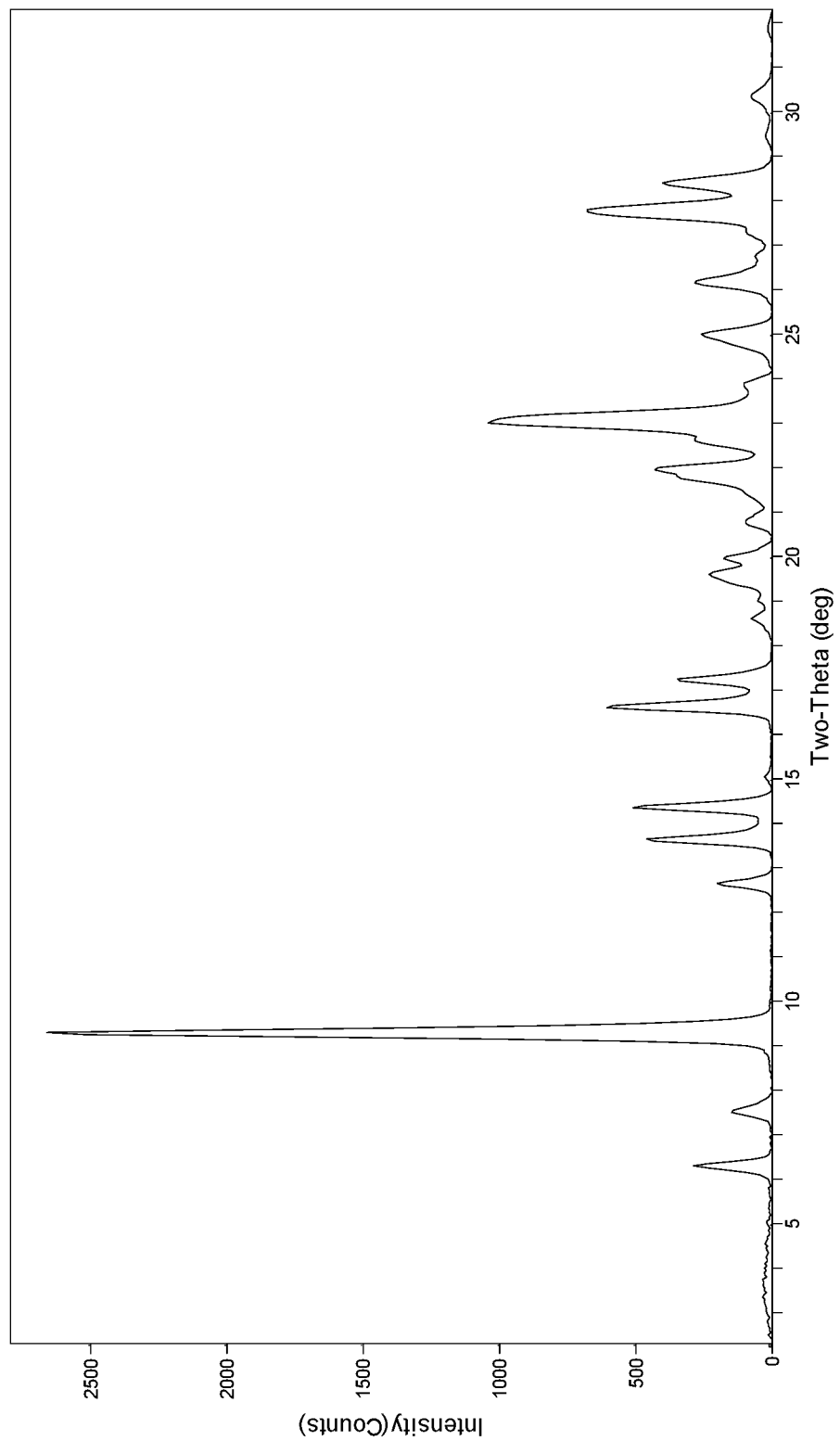
FIG. 2 depicts a powder X-ray diffraction pattern (CuKα at room temperature) of Form B of Compound 1.

The Form B can also be characterized by an X-ray diffraction pattern substantially as depicted in FIG. 2.

Diffraction peak positions for the Form B, at room temperature, based on a high quality pattern collected with a diffractometer (CuKα) with a spinning capillary with 2θ calibrated with a NIST, or other suitable standard, are shown in Table 5.

TABLE 5

| Characteristic diffraction peak positions for the Form B |
|---|
| degrees 2θ ± 0.2 |
| 7.5 |
| 9.3 |
| 12.7 |
| 14.4 |
| 17.2 |
| 27.8 |
| 28.5 |

The Form B of Compound 1 can be characterized by an X-ray diffraction pattern having one peak, or at least one peak, selected from 7.5, 9.3, 12.7, 14.4, 17.2, 27.8, and 28.5 (the values listed in Table 4) degrees 2θ±0.2 degrees 2θ. The Form B can also be characterized by an X-ray diffraction pattern having two peaks selected from the values listed in Table 5. The Form B can also be characterized by an X-ray diffraction pattern having three peaks selected from the values listed in Table 5. The Form B can also be characterized by an X-ray diffraction pattern having four peaks selected from the values listed in Table 5. The Form B can also be characterized by an X-ray diffraction pattern having five peaks selected from the values listed in Table 5. The Form B can also be characterized by an X-ray diffraction pattern having six peaks selected from the values listed in Table 5. The Form B of Compound 1 can also be characterized by an X-ray diffraction pattern having peaks at 7.5, 9.3, 12.7, 14.4, 17.2, 27.8, and 28.5 degrees 2θ±0.2 degrees 2θ.

The Form B can be in substantially pure form, that is, having a purity of about 90% or greater, based on the weight of the compound, as determined by HPLC. For example, the Form B can have a purity of about 90, 91, 92, 93, 94, 95, 96, 97, 98, 99, or 100%. The remaining material can comprise other solid forms of Compound 1 and/or reaction impurities and/or processing impurities arising from its preparation.

Mixtures of the Form B of Compound 1 with other solid forms of Compound 1 are also within the scope of the disclosure. In these embodiments, such mixtures can comprise less than 90%, based on the weight of the mixture, of the Form B of Compound 1. For example, mixtures can comprise 85, 80, 75, 70, 65, 60, 55, 50, 45, 40, 35, 30, 25, 20, 15, 10, or about 5%, by weight of the mixture, of the Form B.

Samples of the crystalline forms described herein (e.g., Form A and Form B) may be provided with substantially pure phase homogeneity, indicating the presence of a dominant amount of a single crystalline form and optionally minor amounts of one or more other crystalline forms. The presence of more than one crystalline form in a sample may be determined by techniques such as powder X-ray diffraction (PXRD) or solid-state nuclear magnetic resonance spectroscopy (ssNMR). For example, the presence of extra peaks in the comparison of an experimentally measured PXRD pattern with a simulated PXRD pattern may indicate more than one crystalline form in the sample. The simulated PXRD may be calculated from single crystal X-ray data, see Smith, D. K., A FORTRAN Program for Calculating X-Ray Powder Diffraction Patterns, Lawrence Radiation Laboratory, Livermore, Calif., UCRL-7196 (April 1963). Preferably, the crystalline form has substantially pure phase homogeneity as indicated by 10% or less, preferably 5% or less, and more preferably 2% or less of the total peak area in the experimentally measured PXRD pattern arising from the extra peaks that are absent from the simulated PXRD pattern. Most preferred is a crystalline form having substantially pure phase homogeneity with 1% or less of the total peak area in the experimentally measured PXRD pattern arising from the extra peaks that are absent from the simulated PXRD pattern.

The various solid forms described herein may be distinguishable from one another through the use of various analytical techniques known to one of ordinary skill in the art. Such techniques include, but are not limited to, powder X-ray diffraction (PXRD), differential scanning calorimetry (DSC), and/or thermogravimetric analysis (TGA).

One of ordinary skill in the art will appreciate that an X-ray diffraction pattern may be obtained with a measurement error that is dependent upon the measurement conditions employed. In particular, it is generally known that intensities in an X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about ±0.2 degrees 2θ, and such degree of measurement error should be taken into account as pertaining to the aforementioned diffraction angles. Consequently, it is to be understood that the crystal forms of the instant invention are not limited to the crystalline forms that provide X-ray diffraction patterns completely identical to the X-ray diffraction patterns depicted in the accompanying figures disclosed herein. Any crystalline forms that provide X-ray diffraction patterns substantially identical to those disclosed in the accompanying figures fall within the scope of the present invention. The ability to ascertain substantial identities of X-ray diffraction patterns is within the purview of one of ordinary skill in the art.

The solid forms of Compound 1 described herein may be formulated into pharmaceutical compositions and/or employed in therapeutic and/or prophylactic methods. These methods include, but are not limited to, the administration of solid forms of Compound 1, alone or in combination with one or more other pharmaceutically active agents, including agents that may be useful in the treatment of the disorders described herein.

Pharmaceutical Compositions and Administration

The disclosure also provides pharmaceutically acceptable compositions which comprise a therapeutically effective amount of one or more of the solid forms described herein, formulated together with one or more pharmaceutically acceptable excipients (carriers or additives) and/or diluents, and optionally, one or more additional therapeutic agents. In certain embodiments, a pharmaceutical composition comprising one or more of the solid forms of the invention, and one or more pharmaceutically acceptable excipients.

In some embodiments, the solid forms of the invention can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, $22^{nd}$ Edition (Pharmaceutical Press, London, U K. 2012).

Routes of Administration and Composition Components

In some embodiments, the solid forms of the invention described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral). In certain embodiments, a preferred route of administration is systemic.

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 10:788-795 (2006).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the solid forms of the invention described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEGs, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the solid forms of the invention described herein are administered at a dosage of from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 1 mg/kg; from about 0.1 mg/kg to about 0.5 mg/kg).

Regimens

The foregoing dosages can be administered on a daily basis (e.g., as a single dose or as two or more divided doses) or non-daily basis (e.g., every other day, every two days, every three days, once weekly, twice weekly, once every two weeks, once a month).

In some embodiments, the period of administration of the composition described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

Indications

In any of the methods described herein, the subject can have a cancer. In some examples of any of the methods described herein, the mammal has been identified as having a cancer, or has been diagnosed as having a cancer.

Non-limiting examples of cancer include: acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In certain embodiments, non-limiting examples of cancer include: breast cancer, colon cancer, rectal cancer, colorectal cancer, pancreatic cancer, and prostate cancer.

Methods for diagnosing a subject as having a cancer or identifying a mammal as having a cancer are well known in the art. For example, a medical professional (e.g., a physician, a physician's assistant, or a technician) can diagnose cancer in a mammal by observing one or more symptoms of cancer in a mammal. Non-limiting examples of symptoms of cancer include: fatigue, lump or area of thickening felt under the skin, weight change, jaundice, darkening or redness of the skin, sores that won't heal, changes to existing moles, changes in bowel or bladder habits, persistent cough or trouble breathing, difficulty swallowing, hoarseness, persistent indigestion or discomfort after eating, persistent, unexplained muscle or joint pain, persistent, unexplained fevers or night sweats, and unexplained bleeding or bruising. Methods of diagnosing a subject as having a cancer or identifying a subject as having a cancer can further include performing one or more diagnostic tests (e.g., performing one or more diagnostic tests on a biopsy or a blood sample).

In some examples of any of the methods described herein, a subject can be a subject having a cancer, a subject diagnosed as having a cancer, or a subject identified as having a cancer that has been unresponsive to a previously administered treatment for cancer. Diagnostic tests for diagnosing a subject as having a cancer or identifying a mammal as having a cancer are known in the art.

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

In some embodiments, the present invention provides a method of treating cancer, wherein the cancer can be any cancer that does not elicit an optimal innate immune system response.

Innate immune system refers to a part of the immune system consisting of cells that react to threats for the organism like infections or cancer in an antigen-non-specific way and stimulate the adaptive, antigen-specific immune system. In general, complete removal of the threat and long-lasting protection (=immunity) requires activity of the adaptive, antigen-specific immune system that in turn depends on stimulation by the innate immune system.

In some embodiments, the present invention provides a method of treating case, the cancer is selected based on resistance to T-cell checkpoint inhibition, either independent of cancer type and based on failure to respond to previous T-cell checkpoint inhibitor therapy or based on cancer type that is generally resistant to T-cell checkpoint inhibitor therapy such as hormone receptor positive breast cancer, microsatellite stable colon or rectal cancer, pancreatic cancer and prostate cancer.

In certain other embodiments, the present invention provides a method of treating cancer comprising an NLPR3 agonist of the present invention to treat non-inflamed tumors with low CD8+ T-cell infiltration to enhance tumor immunogenicity and promote inflammatory responses. For example, the combination may be used to treat a solid tumor based on results of a biopsy that demonstrated low CD8+ T-cell infiltration or low expression of genes produced by CD8+ T-cells.

Resistance to T-cell checkpoint inhibition refers to cancer progression on therapy or lack of response within 6 months of therapy according to consensus response criteria for the respective cancer, such as RECIST1.1 for most solid tumors.

T-cell infiltration refers to percent of T-cells of all nucleated cells by immunohistochemistry of tumor biopsy specimens.

CD8+ T-cell infiltration refers to percent of CD8+ cells of all nucleated cells by immunohistochemistry of tumor biopsy specimens.

In addition to immunohistochemistry for quantifying CD8+ T-cells in biopsy specimens, expression of genes produced by CD8+ T-cells like interferon-γ can be measured by quantifying mRNA using for example next generation sequencing and inform about CD8+ T-cell infiltration. Thresholds for low and high CD8+ T-cell infiltration by immunohistochemistry of mRNA quantifying techniques are being developed by various groups and take the spectrum of CD8+ T-cell infiltration across cancers as well as for specific cancers into account.

In any of the methods described herein, the subject can have an infectious disease. In some examples of any of the methods described herein, the subject has been identified as having an infectious disease, or has been diagnosed as having an infectious disease. For example, an infectious disease can be caused by a bacterium, virus, fungus, parasite, or a mycobacterium.

Non-limiting examples of infectious disease include: Acinobacter infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, *Burkholderi* infection, Buruli ulcer, Calicivirus infection, camptobacteriosis, candidiasis, cat-scratch disease, cellulitis, Chagas disease, chancroid, chickenpox, chikungunya, chlamydia, *Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, Desmodesmus infection, deintamoebiasis, diphtheria, diphyllobothriasis, dracunculiasis, ebola hemorrhagic fever, echinococcosis, ehrlichiosis, enterobiasis, *Enterococcus* infection, Enterovirus infection, epidemic typhus, erythema infection, exanthema subitum, fasciolopsiasis, fasciolosis, fatal familial insomnia, filariasis, food poisoning by *Clostridium* myonecrosis, free-living amebic infection, *Fusobacterium* infection, gas gangrene, geotrichosis, Gerstmann-Sträussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human ewingii ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, *Kingella kingae* infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, staphylococcal infection, strongyloidiasis, subacute sclerosing panencephalitis, syphilis, taeniasis, tetanus, tinea barabe, tinea capitis, tinea corporis, tinea cruris, tinea manum, tinea nigra, tinea pedis, tinea unguium, tinea versicolor, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

Methods for diagnosing a subject as having an infectious disease, or identifying a subject as having an infectious disease are well known in the art. For example, a medical professional (e.g., a physician, a physician's assistant, or a technician) can diagnose infectious disease in a subject by observing one or more symptoms of infectious disease in a subject. Non-limiting examples of symptoms of infectious disease include: fever, diarrhea, fatigue, and muscle aches. Methods of diagnosing a mammal as having an infectious disease or identifying a subject as having an infectious disease can further include performing one or more diagnostic tests (e.g., performing one or more diagnostic tests on a biopsy or a blood sample). Diagnostic tests for diagnosing a subject as having an infectious disease or identifying a subject as having an infectious disease are known in the art.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies comprise surgery, radiotherapy, chemotherapy, toxin therapy, immunotherapy, cryotherapy or gene therapy, or a combination thereof.

In some embodiments, the one or more additional cancer therapies is chemotherapy, which can include administering one or more additional chemotherapeutic agents.

In certain embodiments, the additional cancer therapy comprises (chemotherapeutic agent) an immunomodulatory moiety, e.g., an immune checkpoint inhibitor. In certain of these embodiments, the immune checkpoint inhibitor targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine-TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12. See, e.g., Postow, M. *J. Clin. Oncol.* 33, 1 (2015).

In certain embodiments, the immune checkpoint inhibitor targets an immune checkpoint receptor selected from CTLA-4, PD-1, PD-L1, PD-1-PD-L1, and PD-1-PD-L2.

In certain embodiments, the immune checkpoint inhibitor is selected from: nivolumab (also known as "OPDIVO"; formerly designated 5C4, BMS-936558, MDX-1106, or ONO-4538), pembrolizumab (also known as "KEYTRUDA", lambrolizumab, and MK-3475. See WO 2008/156712), PDR001 (Novartis; see WO 2015/112900), MEDI-0680 (AstraZeneca; AMP-514; see WO 2012/145493), cemiplimab (REGN-2810) (Regeneron; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (SHR-1210; Jiangsu Hengrui Medicine; see WO 2015/085847; Si-Yang Liu et al., *J. Hematol. Oncol.* 10:136 (2017)), TSR-042 (ANB011; Tesaro Biopharmaceutical; see WO2014/179664), GLS-010

(WBP3055; Wuxi/Harbin Gloria Pharmaceuticals; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGD013 (Macrogenics); IBI308 (Innovent; see WO 2017/024465, WO 2017/025016, WO 2017/132825, WO2017/133540); BMS-936559 (formerly 12A4 or MDX-1105; see, e.g., U.S. Pat. No. 7,943,743 and WO 2013/173223), MPDL3280A (also known as RG7446, atezolizumab, and TECENTRIQ; U.S. Pat. No. 8,217,149; see, also, Herbst et al. (2013) J Clin Oncol 31(suppl):3000), durvalumab (IMFINZI; MEDI-4736; AstraZeneca; see WO 2011/066389), avelumab (Pfizer; MSB-0010718C; BAVENCIO; see WO 2013/079174), STI-1014 (Sorrento; see WO2013/181634), CX-072 (Cytomx; see WO2016/149201), KN035 (3D Med/Alphamab; see Zhang et al., *Cell Discov.* 7:3 (March 2017), LY3300054 (Eli Lilly Co.; see, e.g, WO 2017/034916), CK-301 (Checkpoint Therapeutics; see Gorelik et al., AACR: Abstract 4606 (April 2016)); urelumab, PF-05082566, MEDI6469, TRX518, varlilumab, CP-870893, BMS-986016, MGA271, lirilumab, IPH2201, emactuzumab, INCB024360, galunisertib, ulocuplumab, BKT140, Bavituximab, CC-90002, bevacizumab, MNRP1685A, ipilimumab (YERVOY; U.S. Pat. No. 6,984,720), MK-1308 (Merck), AGEN-1884 (Agenus Inc.; WO 2016/196237), and tremelimumab (formerly ticilimumab, CP-675,206; AstraZeneca; see, e.g., WO 2000/037504 and Ribas, *Update Cancer Ther.* 2(3): 133-39 (2007)).

In certain embodiments, the immune checkpoint inhibitor is selected from: nivolumab, pembrolizumab, JS001, BGB-A317, INCSHR1210, TSR-042, GLS-010, STI-1110, MGD013, IBI308, BMS-936559, atezolizumab, durvalumab, avelumab, STI-1014, CX-072, KN035, LY3300054, CK-301, urelumab, PF-05082566, MEDI6469, TRX518, varlilumab, BMS-986016, ipilimumab, AGEN-1884, and tremelimumab.

In certain of these embodiments, the immune checkpoint inhibitor is selected from: Urelumab, PF-05082566, MEDI6469, TRX518, Varlilumab, CP-870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS-986016, MGA271, Lirilumab, IPH2201, Emactuzumab, INCB024360, Galunisertib, Ulocuplumab, BKT140, Bavituximab, CC-90002, bevacizumab, and MNRP1685A.

In certain embodiments, the additional cancer therapy comprises one or more agents selected from nivolumab, pembrolizumab, PDR001, MEDI-0680, cemiplimab, JS001, BGB-A317, INCSHR1210, TSR-042, GLS-010, AM-0001, STI-1110, AGEN2034, MGD013, IBI308, BMS-936559, atezolizumab, durvalumab, avelumab, STI-1014, CX-072, LY3300054, CK-301, urelumab, PF-05082566, MEDI6469, TRX518, varlilumab, CP-870893, BMS-986016, MGA271, lirilumab, IPH2201, emactuzumab, INCB024360, galunisertib, ulocuplumab, BKT140, Bavituximab, CC-90002, bevacizumab, 1VINRP1685A, ipilimumab, MK-1308, AGEN-1884, and tremelimumab.

In certain embodiments, the immune checkpoint inhibitor is selected from: nivolumab, ipilimumab, pembrolizumab, atezolizumab, durvalumab and avelumab.

In certain embodiments, the immune checkpoint inhibitor is selected from: nivolumab and ipilimumab.

In certain embodiments, the additional anti-cancer agent (chemotherapeutic agent) is a STING agonist. For example, the STING agonist can include cyclic di-nucleotides, such as cAMP, cGMP, and cGAMP as well as modified cyclic di-nucleotides that include one or more of the following modification features (2'-O/3'-O linkage, phosphorothioate linkage, adenine and/or guanine analogue, 2'-OH modification (e.g., —OCH$_3$ or replacement, e.g., —F or N$_3$). See, e.g., WO 2014/189805.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semisynthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an anti-metabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a vinca alkaloid, a podophyllotoxin and/or a taxane. Vinca alkaloids, in general, bind to specific sites on tubulin, inhibiting the assembly of tubulin into microtubules, generally during the M phase of the cell cycle. In an embodiment, a vinca alkaloid is derived, without limitation, from the Madagascar periwinkle, *Catharanthus roseus* (formerly known as *Vinca rosea*). In an embodiment, a vinca alkaloid includes, without limitation, Vincristine, Vinblastine, Vinorelbine and/or Vindesine. In an embodiment, a taxane includes, but is not limited to, Taxol, Paclitaxel and/or Docetaxel. In a further embodiment a plant alkaloid or terpenoid is a synthetic, semisynthetic or derivative. In a further embodiment, a podophyllotoxin is, without limitation, an etoposide and/or teniposide. In an embodiment, a taxane is, without limitation, docetaxel and/or ortataxel. In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an anthracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613.

In yet another embodiment, the methods can further include administering one or both of: (i) one or more anti-fungal agents (e.g., selected from the group of bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and balsam of peru) and (ii) one or more antibiotics (e.g., selected from the group of amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, amoxicillin, calvulanate, ampicillin, subbactam, piperacillin, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanilimide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, daloprostin, thiamphenicol, tigecycyline, tinidazole, trimethoprim, and teixobactin).

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the NLRP3 protein can serve as a biomarker for certain types of cancer.

In some embodiments, the solid form(s) of the invention, methods, and compositions described herein can be administered to certain treatment-resistant patient populations (e.g., patients resistant to checkpoint inhibitors).

In some embodiments, the solid form(s) of the invention may be used in therapy. In certain embodiments, the present invention provides a combined preparation of the solid forms of the invention, and additional therapeutic agent(s) for simultaneous, separate or sequential use in therapy.

In some embodiments, the solid form(s) of the invention, or a pharmaceutical composition containing the same, may be used as a medicament. In certain embodiments, the solid form(s) of the invention may be used for the manufacture of a medicament for the treatment of cancer. In certain embodiments, the solid form(s) of the invention may be used for the manufacture of a medicament for modulating NLRP3 activity. In certain embodiments, the modulating comprises agonizing NLRP3.

Definitions

Some aspects of the disclosure are directed to crystalline forms. Crystalline forms produce an X-ray diffraction pattern with sharp maxima.

As used herein, "polymorphs" refer to crystalline forms having the same chemical structure but different spatial arrangements of the molecules and/or ions forming the crystals.

As used herein, "amorphous" refers to a solid form of a molecule and/or ion that is not crystalline. An amorphous solid does not display a definitive X-ray diffraction pattern with sharp maxima.

As used herein "solvate" refers to a crystalline form of a molecule, atom, and/or ions that further comprises molecules of a solvent or solvents incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Solvates may occur as dimers or oligomers comprising more than one molecule or Compound 1 within the crystalline lattice structure.

As used herein, "hydrate" refers to a crystalline form of a molecule that further comprises water incorporated into the crystalline structure. The water molecules in the hydrate may be present in a regular arrangement and/or a non-ordered arrangement. The hydrate may comprise either a stoichiometric or nonstoichiometric amount of the water molecules. The water molecules in the hydrate may be present in a regular arrangement and/or a non-ordered arrangement. The hydrate may comprise either a stoichiometric or nonstoichiometric amount of the water molecules. For example, a hydrate with a nonstoichiometric amount of water molecules may result from partial loss of water from the hydrate.

As used herein, "substantially pure," when used in reference to a crystalline form, means a compound having a purity greater than 90 weight %, including greater than 90, 91, 92, 93, 94, 95, 96, 97, 98, and 99 weight %, and also including equal to about 100 weight % of Compound 1, based on the weight of the compound. The remaining material comprises other form(s) of the compound, and/or reaction impurities and/or processing impurities arising from its preparation. For example, a crystalline form of Compound 1 may be deemed substantially pure in that it has a purity greater than 90 weight %, as measured by means that are at this time known and generally accepted in the art, where the remaining less than 10 weight % of material comprises amorphous and/or other form(s) of Compound 1 and/or reaction impurities and/or processing impurities.

As used herein, a PXRD pattern "comprising" a number of peaks selected from a specified group of peaks, is intended to include PXRD patterns having additional peaks that are not included in the specified group of peaks.

The presence of reaction impurities and/or processing impurities may be determined by analytical techniques known in the art, such as, for example, chromatography, nuclear magnetic resonance spectroscopy, mass spectrometry, and/or infrared spectroscopy.

As used herein, the unit cell parameter "molecules/unit cell" refers to the number of molecules of Compound 1 in the unit cell.

An "agonist" of NLRP3 includes compounds that, at the protein level, directly bind or modify NLRP3 such that an activity of NLRP3 is increased, e.g., by activation, stabilization, altered distribution, or otherwise.

Certain compounds described herein that agonize NLRP3 to a lesser extent than a NLRP3 full agonist can function in assays as antagonists as well as agonists. These compounds antagonize activation of NLRP3 by a NLRP3 full agonist because they prevent the full effect of NLRP3 interaction. However, the compounds also, on their own, activate some NLRP3 activity, typically less than a corresponding amount of the NLRP3 full agonist. Such compounds may be referred to as "partial agonists of NLRP3".

In some embodiments, the compounds described herein are agonists (e.g. full agonists) of NLRP3. In other embodiments, the compounds described herein are partial agonists of NLRP3.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

In one aspect, methods for modulating (e.g., agonizing, partially agonizing, antagonizing) NLRP3 activity are featured that include contacting NLRP3 with a chemical entity described herein (e.g., a compound described generically or specifically herein or a pharmaceutically acceptable salt thereof or compositions containing the same). In preferred embodiments, methods for modulating NLRP3 activity are agonizing and partially agonizing. In certain embodiments, methods for modulating NLRP3 activity are agonizing. In certain embodiments, methods for modulating NLRP3 activity are partially agonizing. Methods include in vitro methods, e.g., contacting a sample that includes one or more cells comprising NLRP3 (e.g., THP-1 cells) with the chemical entity. Methods can also include in vivo methods; e.g., administering the chemical entity to a subject (e.g., a human) having a disease in which an increase in NLRP3 signaling may correct a deficiency in innate immune activity that contributes to the pathology and/or symptoms and/or progression of the disease (e.g., cancer; e.g., a refractory cancer).

In some embodiments, compounds of the invention are useful for treating a condition, disease or disorder in which a decrease in NLRP3 activity (e.g., a condition, disease or disorder associated with repressed or impaired NLRP3 signaling) contributes to the pathology and/or symptoms and/or progression of the condition, disease or disorder (e.g., cancer) in a subject (e.g., a human).

A cancer is said to be refractory when it does not respond to (or is resistant to) cancer treatment. Refractory cancer is also known as resistant cancer.

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same). In some embodiments, the cancer may be a refractory cancer In a further aspect, methods of treatment of a disease in which an increase in NLRP3 signaling may correct a deficiency in innate immune activity that contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering to a subject having a disease in which an increase in NLRP3 signaling may correct a deficiency in innate immune activity that contributes to the pathology and/or symptoms and/or progression of the disease an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which an increase in NLRP3 signaling may correct a deficiency in innate immune activity that contributes to the pathology and/or symptoms and/or progression of the disease, thereby treating the disease.

Embodiments can include one or more of the following features.

The subject can have cancer; e.g., the subject has undergone and/or is undergoing and/or will undergo one or more cancer therapies.

The chemical entity can be administered intratumorally.

The chemical entity can be administered systemically (including but not limited to orally, subcutaneously, intramuscular, intravenously).

The methods can further include identifying the subject.

Other embodiments include those described in the Detailed Description and/or in the claims.

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP3 molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a drug or pharmaceutical agent being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 22nd Edition, Pharmaceutical Press, London, U K (2012); *Handbook of Pharmaceutical Excipients,* 6th ed.; Rowe et al., Eds.; The Pharmaceutical Press and the American Pharmaceutical Association: (2009); *Handbook of Pharmaceutical Additives,* 3rd ed.; Ash and Ash Eds.; Gower Publishing Company: (2007); *Pharmaceutical Preformulation and Formulation,* 2nd ed.; Gibson Ed.; CRC Press LLC: Boca Raton, Fla., (2009).

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt is not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "haloalkoxy" refers to an —O-haloalkyl radical (e.g., —OCF$_3$).

The term "alkylene" refers to a branched or unbranched divalent alkyl (e.g., —CH$_2$—).

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkylene" as used herein refers to divalent cycloalkyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Examples of heteroaryl groups also include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. The term "heterocycloalkylene" refers to divalent heterocyclyl.

The term "Brønsted acid" refers to a proton (H$^+$) donor.

The term "Lewis acid" refers to a chemical species that can accept an electron pair from an electron donor compound.

The term "Brønsted base" refers to a proton (H$^+$) acceptor.

The term "Lewis base" refers to a chemical species that can donate an electron pair to an electron acceptor compound.

The term "transition metal catalyst" refers to a coordination complex that has any of various metallic elements such as palladium and nickel that have valence electrons in two shells instead of only one and, when added to a chemical reaction, increases the rate of reaction.

A protic solvent refers to a solvent that has a hydrogen atom bound to an oxygen (as in a hydroxyl group) or a nitrogen (as in an amine group).

An aprotic solvent refers to a solvent that is not a hydrogen bond donor.

A polar solvent refers to a solvent with large dipole moments or partial charges; they contain bonds between atoms with very different electronegativities, such as oxygen and hydrogen.

Solvent mixture refers to a combination of two or more solvents.

The term "additive" refers to a substance added to the reaction mixture to improve the reaction performance, e.g. improving reaction yield and minimizing impurities formation.

The term "phosphine ligand" refers to phosphines, compound of the formula PRR'R" (R, R', R"=H, alkyl, aryl, etc.) that are used as ligands in metal complexes.

The term "electrophilic halogenation reagent" refers to an electrophilic substance that enable the replacement of a hydrogen atom by a halogen atom in a molecule.

The term "acylation reagent" refers to a substance adding an acyl group to a molecule.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

EXAMPLES

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

The starting materials used in the synthetic sequence of the invention are known, made by known methods, or are commercially available. The skilled artisan will also recognize that conditions and reagents described herein that can be interchanged with alternative art-recognized equivalents. For example, in one reactions, hydrochloric acid can be interchanged with other acids, such as hydrobromic acid, sulfuric acid, etc.

The skilled artisan will recognize a variety of analytical methods that can be used to characterize the compounds described herein, including, for example, $^1$H nuclear magnetic resonance spectroscopy (NMR), heteronuclear NMR, mass spectrometry (MS), liquid chromatography (LC), and infrared (IR) spectroscopy. The foregoing list is a subset of characterization methods available to a skilled artisan and is not intended to be limiting.

To further illustrate the foregoing, the following non-limiting, exemplary synthetic schemes are included. Variations of these examples within the scope of the claims are within the purview of one skilled in the art and are considered to fall within the scope of the invention as described, and claimed herein. The reader will recognize that the skilled artisan, provided with the present disclosure, and skill in the art is able to prepare and use the invention without exhaustive examples.

The following abbreviations have the indicated meanings:

Ac$_2$O=acetic anhydride
AcOH=acetic acid
[(Allyl)PdCl]$_2$=allylpalladium chloride dimer
aq=aqueous
AtaPhos=(4-(N,N-dimethylamino)phenyl)di-tert-butyl phosphine
BISBI=2,2'-bis(diphenylphosphinomethyl)-1,1'-biphenyl
BiPHEP=2,2'-bis(diphenylphosphino)-1,1'-biphenyl
B$_2$(OH)$_4$=tetrahydroxydiboron
B(npg)=neopentyl glycolatoboron
B$_2$(npg)$_2$=bis(neopentyl glycolato)diboron
BPin=pinacolatoboron
B$_2$(Pin)$_2$=bis(pinacolato)diboron
BuOH=n-butanol
caPhos=dicyclohexyl(4-(N,N-dimethylamino)phenyl) phosphine
CDCl$_3$=deuterated chloroform
CH$_3$CN=acetonitrile
[(cinnamyl)PdCl]$_2$=Palladium(1-phenylallyl)chloride dimer
CPhos=2-dicyclohexylphosphino-2',6'-bis(N,N-dimethylamino)biphenyl
CPME=cyclopentyl methyl ether
[(crotyl)PdCl]$_2$=(2-butenyl)chloropalladium dimer
CX-A=butyldi-1-adamantylphosphine
CX-ABn=benzyldi-1-adamantylphosphine
CX-PCy=N-phenyl-2-(dicyclohexylphosphino)pyrrole
CX-POMeCy=1-(2-methoxyphenyl)-2-(dicyclohexylphosphino)pyrrole
Cy-BIPHEP=2,2'-bis(dicyclohexylphosphino)biphenyl
Cy-DavePhos=dicyclohexylphosphinodimethylaminobiphenyl
Cy-JohnPhos=2-(dicyclohexylphosphino)biphenyl
CyXantphos=1,1'-(9,9-dimethyl-9H-xanthene-4,5-diyl) bis[1,1-dicyclohexyl-phosphine]
d=doublet
DBU=1,8-diazabicyclo[5.4.0]undec-7-ene
DCE=1,2-dichloroethane
DCM=dichloromethane
DCPB HBF$_4$=1,4-bis(dicyclohexylphosphonium)butane bis(tetrafluoroborate)
DCPP=dicyclohexyl[3-(dicyclohexylphosphino)propyl] phosphine
DCyPF=1,1'-bis(dicyclohexylphosphino)ferrocene
DIPEA=N,N-diisopropylethylamine
DMAc=dimethylacetamide
DME=1,2-dimethoxyethane DMF=dimethylformamide
DMSO=dimethylsulfoxide
DMSO-$d_6$=deuterated dimethylsulfoxide
DPEPhos=bis(diphenylphosphinophenyl)ether
(DPEPhos)PdCl$_2$=dichlorobis(diphenylphosphinophenyl)ether palladium (II)
DPPB=1,4-bis(diphenylphosphino)butane
DPP-DtBPF=1-diphenylphosphino-1'-(di-tert-butylphosphino)ferrocene
DPPE=1,2-bis(diphenylphosphino)ethane
DPPF=1,1'-bis(diphenylphosphino)ferrocene
(DPPF)PdCl$_2$=[1,1'-bis(diphenylphosphino)ferrocene]dichloropalladium(II)
DPPPent=bisdiphenylphosphinopentane
equiv=equivalent(s)
ESI=electrospray ionization
EtOAc=ethyl acetate
EtOH=ethanol
g=gram(s)
h=hour(s)
HCl=hydrogen chloride (usually as a solution)
HBr=hydrogen bromide (usually as a solution)
HBF$_4$=fluoroboric acid
HexLi=hexyllithium
H$_2$O=water
H$_3$PO$_4$=phosphoric acid
H$_2$SO$_4$=sulfuric acid
I$_2$=iodine
IPA=isopropyl alcohol
IPAc=isopropyl acetate
iPrMgCl=isopropylmagnesium chloride
iPrOAc=isopropyl acetate
KOAc=potassium acetate
kg=kilogram(s)
KOMe=potassium methoxide
KOPiv=potassium pivalate
KOtBu=potassium tert-butoxide
K$_3$PO$_4$=tripotassium phosphate
L=liter(s)
LC/MS=liquid chromatography mass spectrometer
LiCl=lithium chloride
LiHMDS=lithium bis(trimethylsilyl)amide
LRMS=low resolution mass spectrometry
JackiePhos=2-di[3,5-bis(trifluoromethyl)phenylphosphino]-3,6-dimethoxy-2'-4'-6'-tri-i-propyl-1,1'-biphenyl
m=multiplet
M=molar
mg=milligram(s)
MeCN=acetonitrile
(MeCN)$_2$PdCl$_2$=bis(acetonitrile)dichloropalladium(II)
MEK=methyl ethyl ketone
MeOH=methanol
MeTHF=2-methyltetrahydrofuran
2-Me-THF=2-methyltetrahydrofuran
MHz=megahertz
MIBK=methyl isobutyl ketone
min=minute(s)
mL=milliliter(s)
mmol=millimole(s)
MTBE=methyl tert-butyl ether
Na$_2$CO$_3$=sodium carbonate
NaHSO$_3$=sodium bisulfate
NaOAc=sodium acetate
NaOH=sodium hydroxide
NaOMe=sodium methoxide
NaOPiv=sodium pivalate
NaOtBu=sodium tert-butoxide
NBS=N-bromosuccinimide
NCS=N-chlorosuccinimide
NH$_4$OH or NH$_3$H$_2$O=ammonium hydroxide
NH$_4$OAc=ammonium acetate
NiCl$_2$·6H$_2$O=nickel(II) chloride hexahydrate
Ni(cod)$_2$=bis(1,5-cyclooctadiene)nickel (0)
Ni(NO$_3$)$_2$·6H$_2$O=nickel(II) nitrate hexahydrate
NIS=N-iodosuccinimide
NMP=N-methyl-2-pyrrolidone
OMs=methanesulfonate, mesylate or —OS(O)$_2$CH$_3$
OTf=trifluoromethanesulfonate, tosylate, or —OS(O)$_2$CF$_3$
OTs=tosylate, p-toluenesulfonate, or —OS(O)$_2$(p-CH$_3$-Ph)
PCy$_3$ HBF$_4$=tricyclohexylphosphonium tetrafluoroborate
PCy$_2$tBu=tert-butyldicyclohexylphosphine
PCy$_2$tBuHBF$_4$=tert-butyldicyclohexylphosphine tetrafluoroboric acid salt
(PCy$_2$tBu)$_2$PdCl$_2$=bis(tert-butyldicyclohexylphosphine) palladium (II) dichloride
Pd(AtaPhos)$_2$Cl$_2$=Bis(di-tert-butyl(4-dimethylaminophenyl)phosphine) dichloropalladium(II)
PdCl$_2$(MeCN)$_2$=dichlorobis(acetonitrile)palladium(II)
PdCl$_2$(PPh$_3$)$_2$=bis(triphenylphosphine)palladium (II) dichloride
Pd(dba)$_2$=bis(dibenzylideneacetone)palladium(0)
Pd$_2$(dba)$_3$=tris(dibenzylideneacetone)dipalladium(0)
Pd(DPEPhos)Cl$_2$=dichloro[bis(diphenylphosphinophenyl)ether]palladium(II)
P(DMM-Ph)$_3$=tris(4-methoxy-3,5-dimethylphenyl)phosphine
Pd(Xantphos)Cl$_2$=dichloro[9,9-dimethyl-4,5-bis(diphenylphosphino)-xanthene]palladium(II)
P(fur)$_3$=tri-2-furylphosphine
PhI(OAc)$_2$=(diacetoxyiodo)benzene
Ph-O—CN=phenyl cyanate
Pd(OAc)$_2$=palladium(II) acetate
P(o-Tol)$_3$=tri-o-tolylphosphine
P(p-CF$_3$-Ph)$_3$=tris(4-trifluoromethylphenyl)phosphine
PPh$_3$=triphenylphosphine
PPh$_2$(o-anis)=diphenyl(2-methoxyphenyl)phosphine
PPh$_2$Pyr=2-diphenylphosphinopyridine
ppm=parts per million
PtBu$_3$ HBF$_4$=tri-t-butylphosphonium Tetrafluoroborate
PtBu$_2$Me=di-tert-butylmethylphosphine
PtBu$_2$Me HBF$_4$=di-t-butyl(methyl)phosphonium Tetrafluoroborate
RH=relative humidity
RuPhos=2-dicyclohexylphosphino-2',6'-di-i-propoxy-1,1'-biphenyl
s=singlet
S-Phos=2-dicyclohexylphosphino-2',6'-dimethoxy-1,1'-biphenyl
t=triplet
tB-Xantphos=9,9-dimethyl-4,5-bis(di-t-butylphosphino)xanthene
THF=tetrahydrofuran
TFA=trifluoroacetic acid
° C.=degrees Celsius
UPLC/MS=ultra Performance liquid chromatography mass spectrometer
vol=volumes
wt=weight
Xantphos=[5-(diphenylphosphino)-9,9-dimethyl-9H-xanthen-4-yl](diphenyl)-phosphine XPhos=2-dicyclohexylphosphino-2',4',6'-triisopropylbiphenyl XPhosHBF$_4$=2-dicyclohexylphosphino-2',4',6'-triisopropylbiphenyl tetrafluoroboric acid salt ZnBr$_2$=zinc bromide ZnCl$_2$=zinc chloride Zn(OPiv)$_2$=Zinc pivalate Zn(OTf)$_2$=Zinc trifluoromethanesulfonate A number of embodiments of the invention have been described. Nevertheless, it will be understood that various modifications may be made without departing from the spirit and scope of the invention. Accordingly, other embodiments are within the scope of the following claims.

Experimental Methods

Single Crystal X-Ray Measurements

Single crystal X-ray data for each of Form A and Form B of Compound 1 were collected using a Bruker X8-Proteum diffractometer equipped with a APEX II CCD detector and a MICROSTAR microfocus rotating anode X-ray generator of monochromatic Cu Kα radiation. Unless otherwise stated, the single crystal data collection was at room temperature.

Unit cell parameters were obtained through least-squares analysis of the experimental diffractometer settings of 25 high-angle reflections. Intensities were measured using Cu Kα radiation at a constant temperature with the θ-2θ variable scan technique and were corrected only for Lorentz-polarization factors. Background counts were collected at the extremes of the scan for half of the time of the scan.

Indexing and processing of the measured intensity data were carried out with the APEX2 program suite (Bruker AXS, Inc., 5465 East Cheryl Parkway, Madison, Wis. 53711 USA).

The final unit cell parameters were determined using the full data set. The structures were solved by direct methods and refined by full-matrix least-squares approach using the SHELXTL software package (G. M. Sheldrick, SHELXTL v6.14, Bruker AXS, Madison, Wis. USA.). Structure refinements involved minimization of the function defined by $\Sigma w(|F_o|-|F_c|)^2$, where w is an appropriate weighting factor based on errors in the observed intensities, $F_o$ is the structure factor based on measured reflections, and $F_c$ is the structure factor based on calculated reflections. Agreement between the refined crystal structure model and the experimental X-ray diffraction data is assessed by using the residual factors $R=\Sigma||F_o|-|F_c||/\Sigma|F_o|$ and $wR=[\Sigma w(|F_o|-|F_c|)^2/\Sigma w|F_o|]^{1/2}$. Difference Fourier maps were examined at all stages of refinement. All non-hydrogen atoms were refined with anisotropic thermal displacement parameters. Hydrogen atoms were introduced using idealized geometry with isotropic temperature factors and included in structure factor calculations with fixed parameters.

Powder X-Ray Diffraction (PXRD)

PXRD data were obtained using a Bruker C2 GADDS (General Area Detector Diffraction System) manual chi platform goniometer. The radiation was Cu Kα (40 KV, 40 mA). The sample-detector distance was 15 cm. Samples were placed in sealed glass capillaries with diameters of ≤1 mm. The capillary was rotated during data collection. Data were collected for approximately 2≤2θ≤32° with a sample exposure time of at least 1000 seconds. The resulting two dimensional diffraction arcs were integrated to create a traditional 1-dimensional PXRD pattern with a step size of 0.05 degrees 2θ in the approximate range of 2 to 32 degrees 2θ.

Differential Scanning calorimetry (DSC)

Differential scanning calorimetry (DSC) experiments were performed using a TA Instrument—model Q2000 or Q1000. The sample (about 1-10 mg) was weighed in an aluminum pan and the weight recorded accurately to a hundredth of a milligram before transferring the sample to the DSC. The instrument was purged with nitrogen gas at 50 mL/min. Data were collected between room temperature and 300° C. at a heating rate of 10° C./min. DSC plots were generated such that the endothermic peaks pointed down.

Thermal Gravimetric Analysis (TGA)

Thermal gravimetric analysis (TGA) experiments were performed using a TA Instrument—model Q5000 or Q500. The sample (about 10-30 mg) was placed in a previously tarred platinum pan. The weight of the sample was measured accurately and recorded to a thousandth of a milligram by the instrument. The furnace was purged with nitrogen gas at 100 mL/min. Data were collected between room temperature and 300° C. at a heating rate of 10° C./min.

Moisture Sorption Isotherms

Moisture sorption isotherms were collected in a VTI SGA-100 Symmetric Vapor Analyzer or TA Instrument VTI-SA+ Vapor Sorption Analyzer using approximately 10 mg of sample. The sample was dried at 60° C. until the loss rate of 0.0005 wt %/min was obtained for 10 minutes. The sample was tested at 25° C. and 4 or 5, 15, 25, 35, 45, 50, 65, 75, 85, and 95% RH. Equilibration at each RH was reached when the rate of 0.0003 wt %/min for 35 minutes was achieved or a maximum of 600 minutes.

Example 1: Preparation of tert-butyl ((4-cyano-1H-imidazol-2-yl)methyl)(ethyl)carbamate

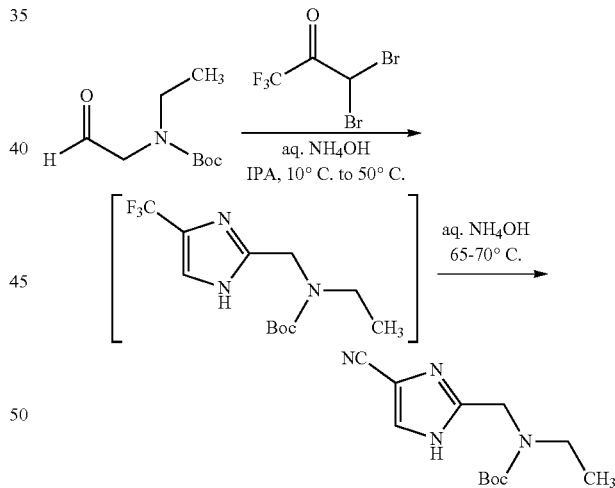

To a 2-L reactor was added tert-butyl ethyl(2-oxoethyl)carbamate (100 g, 1 eq) and IPA (7 vol) and the resulting mixture was cooled to 0-5° C. To this mixture was added aq. ammonium hydroxide (23 wt %, 5 vol). In a separate 500 mL was added H$_2$O (3 vol) followed by the addition of 3,3-dibromo-1,1,1-trifluoropropan-2-one (1.20 eq) at 20° C. The resulting mixture was stirred for 30 min after which it was added to the above IPA solution of tert-butyl ethyl(2-oxoethyl)carbamate over 1 h and maintaining an internal temperature below 30° C. Upon completion of the above addition NH$_4$OAc (3 eq) was added and the resulting mixture was heated to 45-50° C. for 12 h to afford a stream of tert-butyl ethyl((4-(trifluoromethyl)-1H-imidazol-2-yl)

methyl)carbamate. The stream was cooled to 20° C. and MTBE was added (5 vol). The layers were split and the organic stream was washed with aq. Na$_2$CO$_3$ (10 wt %, 5 vol). The layers were split and the organic stream was solvent swapped to IPA via distillation (final volume=4-5 vol). To this mixture was added aq. NH$_4$OH (5-10 wt %, 15 vol) and the mixture was heated to 65-70° C. for 15 h. An aq. K$_3$PO$_4$ solution was added (50 wt %, 3 eq) was added to adjust the pH to 11-12 and the resulting reaction mixture was heated for an additional 6 h. The reaction mixture was cooled to 20° C. and mixture of IPA/MTBE (1:1, 4 vol) was added. The layers were split and the aq layer was washed with IPA/MTBE (1:1, 4 vol). The combined organics were concentrated by distillation to ca. 4 vol and H$_2$O (16 vol) was added. The resulting slurry was cooled to 5° C. and held at that temperature for 12 h. The solids were filtered and washed with IPA/H$_2$O (1:4) to yield tert-butyl ((4-cyano-1H-imidazol-2-yl)methyl)(ethyl)carbamate (85 g, 85 wt %, 57% yield). The resulting low potency solids were re-slurried in hot CPME (2.5 vol) cooled to −5° C. and filtered to yield tert-butyl ((4-cyano-1H-imidazol-2-yl)methyl) (ethyl)carbamate (64 g, 97.5 wt %, 49% yield). M.P.=168 C. $^1$H NMR (400 MHz, d-6 DMSO): δ 8.02 (s, 1H), 4.38 (s, 2H), 2.60 (brs, 2H), 1.35 (m, 9H), 1.10 (t, J=8.0 Hz, 3H). $^{13}$C NMR (100 MHz, DMSO-d$_6$): δ 154.22 147.43, 127.44, 115.90, 111.11, 78.99, 41.71, 27.97, 13.08. UPLC/MS conditions: Column Ascentis Express C18 2.1×50 mm, 2.6 µm particles; Mobile Phase A: 0.05% TFA in CH$_3$CN:Water (5:95); Mobile Phase B: 0.05% TFA in Water: CH$_3$CN (5:95); Temperature: 40° C.; Gradient: 0-100% B over 2 min; stop time 2.5 min; Flow: 1.0 mL/min; LC RT: 1.116 min; LRMS (ESI) Calcd for [C$_{12}$H$_{18}$N$_4$O$_2$+H]$^+$ 251.1. Found 251.1.

Intermediate tert-butyl ethyl((4-(trifluoromethyl)-1H-imidazol-2-yl)methyl)carbamate: white solid, M.P.=100-101° C. $^1$H NMR (400 MHz, CDCl3): δ 10.42 (br s, 1H), 7.30 (s, 1H), 4.38 (s, 2H), 3.34 (q, J=8.0 Hz, 2H), 1.49 (s, 9H), 1.07 (t, J=8.0 Hz, 3H). $^{19}$F NMR 62.61. $^{13}$C NMR (100 MHz, CDCl3): δ 156.82 147.35, 130.8 (q), 121.67 (q: 125.64, 122.99, 120.34, 117.69), 116.77, 80.63, 44.24, 43.19, 28.19, 13.31. UPLC/MS conditions: Column Ascentis Express C18 2.1×50 mm, 2.6 µm particles; Mobile Phase A: 0.05% TFA in CH$_3$CN:Water (5:95); Mobile Phase B: 0.05% TFA in Water: CH$_3$CN (5:95); Temperature: 40° C.; Gradient: 0-100% B over 2 min; stop time 2.5 min; Flow: 1.0 mL/min; LC RT: 1.295 min; LRMS (ESI) Calcd for [C$_{12}$H$_{18}$F$_3$N$_3$O$_2$+H]$^+$ 294.1. Found 294.2.

Example 2: Preparation of tert-butyl ((4-cyano-5-iodo-1H-imidazol-2-yl)methyl)(ethyl)carbamate

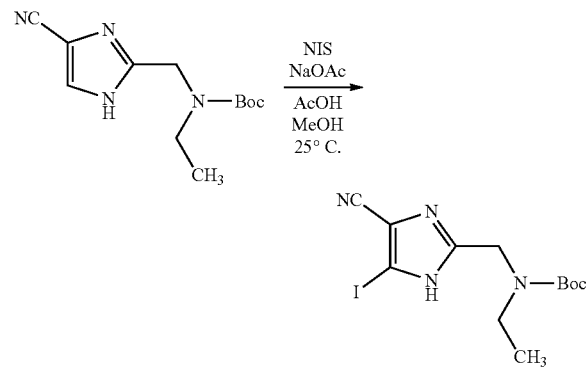

To a 1 L chemglass reactor with the jacket set to 20° C. was charged MeOH (200 mL) followed by tert-butyl ((4-cyano-1H-imidazol-2-yl)methyl)(ethyl)carbamate (50.0 g, 0.200 mmol), N-iodosuccinimide (53.9 g, 1.2 equiv.), NaOAc (24.6 g, 1.5 equiv.), and acetic acid (17.2 mL, 1.5 equiv.). The reactor was then rinsed with MeOH (150 mL). The reactor was heated to 35° C. and maintained overnight (16 h). Water (200 mL) was then charged, followed by tert-butyl ((4-cyano-5-iodo-1H-imidazol-2-yl)methyl) (ethyl)-carbamate seeds (500 mg). The slurry was maintained at 35° C. for 1 h, then cooled to 20° C. over 1.5 h. Water (275 mL) was added over 3 h and the slurry was maintained overnight (~16 h). The slurry was filtered and washed 3 times with 5 volumes of 2:1 water:MeOH. The white solids were dried at 50° C. overnight to yield tert-butyl ((4-cyano-5-iodo-1H-imidazol-2-yl)methyl)(ethyl)carbamate (69.0 g, 183 mmol) as a white solid in 91.7% yield. $^1$H NMR (500 MHz, DMSO-d$_6$) δ 13.49 (br s, 1H), 4.37 (br s, 2H), 3.22 (br s, 2H), 1.33 (m, 9H), 1.01 (t, J=6.9 Hz, 3H). Ultra-High Performance Liquid Chromatography (UHPLC) method conditions: Column: Supelco Ascentis Express C18, 2.7 µm, 2.1×50 mm; Mobile phase A: 0.01 M NH$_4$OAc in acetonitrile:water (5:95); Mobile phase B: 0.01 M NH$_4$OAc in acetonitrile:water (95:5); Temperature: 40° C.; Gradient: 0 min (0% B), 0.3 min (20% B), 3 min (34% B), 4 min (55% B), 4.5 min (100% B), 5.5 min (100% B); Flow: 1.0 mL/min; LC RT 2.44 min; LRMS (ESI) Calcd for [C$_{12}$H$_{18}$IN$_4$O$_2$+H]$^+$ 377.0. Found 377.0.

Example 3: Preparation of 2-chloro-5-(1-(tetrahydro-2H-pyran-2-yl)-1H-pyrazol-5-yl)aniline

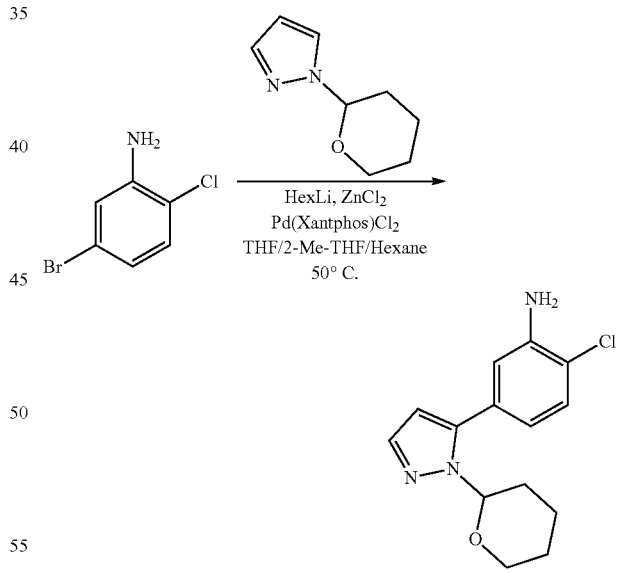

Into an inert chemglass reactor was charged THF (400 mL, 8.0 L/kg) and 1-(2-Tetrahydropyranyl)-1H-pyrazole (47.9 g, 1.3 equiv.). The solution was cooled to −10° C. Hexyllithium solution in hexane (140 mL, 2.3 M, 1.36 eq) was charged slowly so the internal temperature of the reaction was kept below <5° C. during the addition. ZnCl$_2$ solution in 2-Me-THF (180 mL, 1.9 M, 1.40 equiv.) was charged slowly so the internal temperature of the reaction was kept below <5° C. during the addition. The mixture was warmed to 25° C. 5-Bromo-2-chloroaniline (50.0 g, 1.0 equiv) and Pd(Xantphos)Cl$_2$ (1.85 g, 0.01 eq) were charged subsequently. The batch was heated to 50° C. and agitated for 4 h. The batch was cooled to 20° C. and was treated with ethylenediaminetetraacetic acid trisodium salt (EDTA.3Na, 155 g) solution in water (300 mL). The biphasic mixture was agitated for 2 h and allowed to settle. The organic layer was separated and washed with N-acetyl-L-cysteine (63.0 g, 0.58 equiv)/K$_3$PO$_4$ (65.1 g, 0.36 equiv) in water (300 mL, 6.0 L/kg). The biphasic mixture was agitated for 4 h and allowed to settle. The organic layer was separated and washed with brine (13 wt %, 250 mL). The biphasic mixture was agitated for 2 h and allowed to settle. The solution was concentrated to 6.0-7.0 L (6.0-7.0 L/kg) and the solvent was exchanged to toluene by performing constant volume distillation with toluene feed (600 mL, 12.0 L/kg). Upon solvent exchange completion, the solution was heated to 45° C. and heptane (150 mL, 3.0 L/kg) was charged over 30 min. The solution was agitated for 1 h at 45° C. and heptane (850 mL, 17.0 L/kg) was charged over 2 h. The resulting slurry was agitated for additional 1 h at 45° C. and cooled to 20° C. over 1 h. The slurry was continually agitated at 20° C. for 8 h and filtered. The wet cake was washed with 3:1 heptane:toluene (250 mL, 5.0 L/kg) and heptane (250 mL, 5.0 L/kg). The material was dried at 50° C. under vacuum for 12 h to give 2-chloro-5-(1-(tetrahydro-2H-pyran-2-yl)-1H-pyrazol-5-yl) aniline as a pale yellow solid (54.1 g, 81% yield). $^1$H NMR (400 MHz, CDCl$_3$) δ 7.59 (d, J=1.5 Hz, 1H), 7.33 (d, J=8.3 Hz, 1H), 6.92 (d, J=2.0 Hz, 1H), 6.84 (dd, J=8.1, 2.0 Hz, 1H), 6.29 (d, J=1.8 Hz, 1H), 5.21 (dd, J=10.4, 2.5 Hz, 1H), 4.24-4.07 (m, 3H), 3.60 (td, J=11.6, 2.4 Hz, 1H), 2.65-2.48 (m, 1H), 2.12-2.02 (m, 1H), 1.88-1.67 (m, 2H), 1.67-1.52 (m, 3H). UPLC/MS conditions: Column Ascentis Express C18 2.1×50 mm, 2.6 μm particles; Mobile Phase A: 0.01 M NH$_4$OAc in CH$_3$CN:Water (5:95); Mobile Phase B: 0.01 M NH$_4$OAc in Water: CH$_3$CN (5:95); Temperature: 40° C.; Gradient: 0-100% B over 2 min; stop time 2.5 min; Flow: 1.0 mL/min; LC RT: 1.37 min; LC/MS (ESI) Calcd for [C$_{14}$H$_{16}$ClN$_3$O+H]$^+$ 278.1. Found 278.1.

An example with an alternative workup procedure: into an inert chemglass reactor was charged THF (100 mL, 8.0 L/kg) and 1-(2-Tetrahydropyranyl)-1H-pyrazole (11.83 g, 1.3 equiv.). The solution was cooled to −7° C. Hexyllithium solution in hexane (35 mL, 2.3 M, 1.36 eq) was charged slowly so the internal temperature of the reaction was kept below <5° C. during the addition. ZnCl$_2$ solution in 2-Me-THF (44 mL, 1.9 M, 1.40 equiv.) was charged slowly so the internal temperature of the reaction was kept below <5° C. during the addition. The mixture was warmed to 25° C. 5-Bromo-2-chloroaniline (12.4 g, 1.0 equiv) was charged followed by a THF rinse (10 m, 0.8 L/kg). Pd(Xantphos)Cl$_2$ (0.46 g, 0.01 eq) was charged followed by a THF rinse (10 m, 0.8 L/kg). The batch was heated to 50° C. and agitated overnight. The batch was cooled to 20° C. To a separate chemglass reactor, water (100 mL, 8.0 L/kg) and ethylenediamine (24.0 mL, 358 mmol, 6.0 equiv) were charged subsequently. The coupling reaction stream was charged to the ethylene diamine solution at a rate of 2 mL/min. The biphasic mixture was agitated for 4 h and allowed to settle. The organic layer was separated and was concentrated to 6.0-7.0 L (6.0-7.0 L/kg). The solvent was exchanged to IPA by performing constant volume distillation with IPA feed (125 mL, 10.0 L/kg). Upon solvent exchange completion, the solution was heated to 55° C. and water (25 mL, 2.0 L/kg) was charged over 48 min. The batch was cooled to 45° C. and water (6.0 mL, 0.48 L/kg) was charged over 6 min. The solution was agitated for 1 h at 45° C. Additional water (68 mL, 5.44 L/kg) was charged over 2 h. The resulting slurry was agitated for additional 1 h at 45° C. and cooled to 20° C. over 1 h. The slurry was continually agitated at 20° C. overnight and filtered. The wet cake was washed with 2:3 IPA:water (60 mL, 5.0 L/kg) twice. The material was dried at 50° C. under vacuum overnight to give 2-chloro-5-(1-(tetrahydro-2H-pyran-2-yl)-1H-pyrazol-5-yl)aniline as a pale yellow solid (14.6 g, 88% yield).

Example 4: Preparation of tert-butyl ((4-amino-7-(1H-pyrazol-3-yl)-1H-imidazo[4,5-c]quinolin-2-yl)methyl)(ethyl)carbamate Dichloroacetic Acid Salt

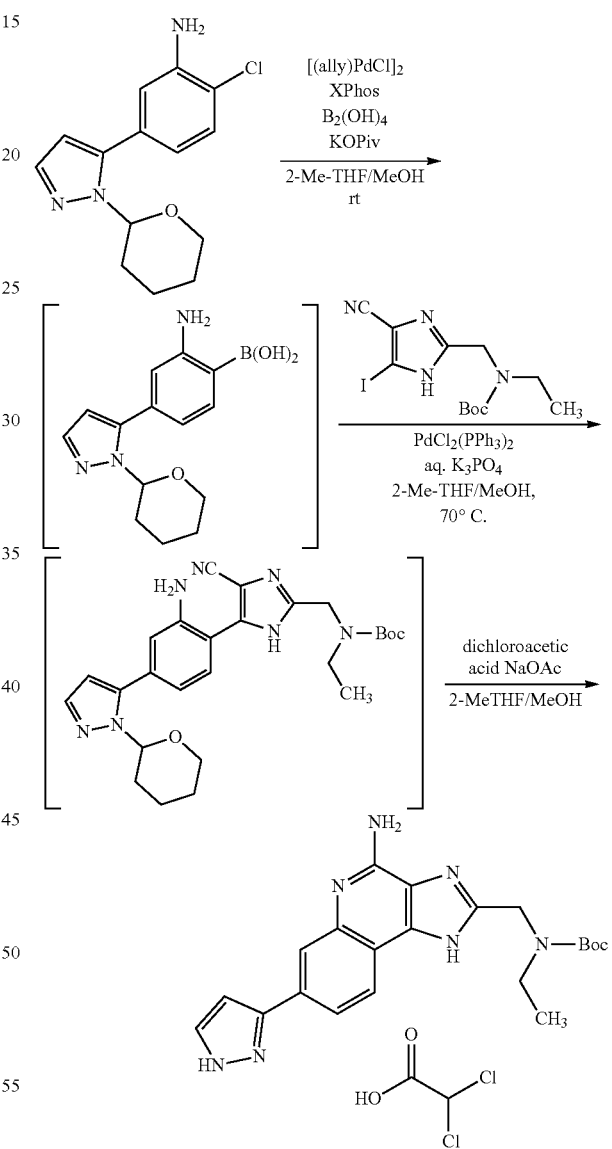

To a 250 mL reactor purged and maintained with an inert atmosphere of nitrogen, was added methanol (45 mL), 2-methyl-tetrahydrofuran (35 mL), 2-chloro-5-(1-(tetrahydro-2H-pyran-2-yl)-1H-pyrazol-5-yl)aniline (8.86 g, 32 mmol, 1.2 equiv), potassium pivalate (6.8 g, 48 mmol, 1.8 equiv), and tetrahydroxydiboron (4.4 g, 48 mmol, 1.8 equiv). The resulting solution was degassed by a nitrogen sparge for 30 minutes at 20° C. To a 20 mL vial, was added 2-dicyclohexylphosphino-2',4',6'-triisopropylbiphenyl (XPhos) (155 mg, 0.32 mmol, 0.012 equiv), allylpalladium chloride dimer (29.5 mg, 0.08 mmol, 0.0030 equiv), and 2-methyl-tetrahydrofuran (10 mL). The resulting solution was degassed by a nitrogen sparge for 30 minutes at 20° C. The catalyst solution was transferred under inert conditions from the 20 mL vial to the 250 mL reactor. The reaction was held at 20° C. for 4 hours. The reaction stream was cooled to 15° C., and degassed aqueous potassium hydroxide (3 M, 44 mL) was added under inert conditions over 15 minutes and the resulting mixture was held at 15° C. for 1 hour. To the reactor was added tert-butyl ((4-cyano-5-iodo-1H-imidazol-2-yl)methyl)(ethyl)carbamate (10 g, 27 mmol, L.R.), bis(triphenylphosphine)palladium dichloride (750 mg, 1.1 mmol, 0.040 equiv), and 2-methyl-tetrahydrofuran (5 mL). The mixture was stirred at 65° C. for 20 hours, then cooled to 20° C. and filtered to remove the solids. The resulting solution was then washed with potassium phosphate monobasic (10 wt %, 60 mL), followed by brine (15 wt %, 60 mL), and then distilled at a constant volume with n-butanol (70 mL), and diluted with methanol (100 mL). Dichloroacetic acid (27.4 g, 213 mmol, 8 equiv) and sodium acetate (4.4 g, 53 mmol, 2 equiv) were added and the resulting solution was stirred at 65° C. for 15 hours, then cooled to 20° C. over 2 hours. The solids were collected by filtration and washed with a mixture of dichloroacetic acid (3.4 g, 27 mmol, 1 equiv) and methanol (50 mL). This resulted in 10.0 g (70% yield) of tert-butyl ((4-amino-7-(1H-pyrazol-5-yl)-1H-imidazo[4,5-c]quinolin-2-yl)methyl)(ethyl)carbamate dichloroacetic acid salt as an off-white solid. $^1$H NMR (500 MHz, DMSO-$d_6$) δ 9.29 (br s, 1H), 8.29 (d, J=8.4 Hz, 1H), 8.20 (s, 1H), 7.95 (br d, J=8.4 Hz, 1H), 7.85 (br s, 1H), 6.81 (s, 1H), 6.28 (s, 1H), 4.70 (s, 2H), 3.23-3.01 (m, 1H), 1.43 (br s, 5H), 1.27 (br s, 4H), 1.11 (br s, 3H). UHPLC method conditions: Column: Supelco Ascentis Express C18, 2.7 μm, 2.1×50 mm; Mobile phase A: 0.01 M NH$_4$OAc in acetonitrile:water (5:95); Mobile phase B: 0.01 M NH$_4$OAc in acetonitrile:water (95:5); Temperature: 40° C.; Gradient: 0 min (0% B), 0.3 min (20% B), 2.5 min (20% B), 5 min (45% B), 6 min (100% B), 8 min (100% B); Flow: 1.0 mL/min; LC RT 1.96 min; LC/MS (ESI) Calcd for $[C_{21}H_{25}N_7O_2+H]^+$=408.2. found 408.2.

Intermediate (2-amino-4-(1-(tetrahydro-2H-pyran-2-yl)-1H-pyrazol-5-yl)phenyl)-boronic acid: $^1$H NMR (500 MHz, DMSO-$d_6$) (NOTE: exists as a mixture of diastereomers of dimer species) δ 9.20-9.14 (m, 0.69H), 8.75 (s, 0.66H), 7.87 (m, 1.53H), 7.66-7.48 (m, 2.26H), 7.39 (s, 0.79H), 7.12 (d, J=7.8 Hz, 0.74H), 6.78 (s, 0.74H), 6.72 (d, J=7.8 Hz, 0.70H), 6.46 (s, 1H), 6.39 (s, 1H), 6.12 (br s, 1H), 5.29 (t, J=9.0, 2H), 4.07-3.95 (m, 2H), 3.62-3.49 (m, 2H), 2.48-2.35 (m, 2H), 2.02-1.90 (m, 2H), 1.88-1.72 (m, 3H), 1.66-1.46 (m, 6H); UHPLC method conditions: Column Supelco Ascentis Express C18, 2.7 μm, 2.1×50 mm; Mobile phase A: 0.01 M NH$_4$OAc in acetonitrile:water (5:95); Mobile phase B: 0.01 M NH$_4$OAc in acetonitrile:water (95:5); Temperature: 40° C.; Gradient: 0 min (0% B), 0.3 min (20% B), 2.5 min (20% B), 5 min (35% B), 8 min (100% B); Flow: 1.0 mL/min; LC RT 1.10 min; LC/MS (ESI) Calcd for $[C_{14}H_{18}BN_3O_3+H]^+$ 288.1. found 288.1.

Intermediate tert-butyl ((5-(2-amino-4-(1-(tetrahydro-2H-pyran-2-yl)-1H-pyrazol-5-yl)phenyl)-4-cyano-1H-imidazol-2-yl)methyl)(ethyl)carbamate: $^1$H NMR (500 MHz, DMSO-$d_6$) δ 7.56 (s, 1H), 6.93 (s, 1H), 6.79 (br d, J=7.5 Hz, 1H), 6.41 (s, 1H), 5.76 (s, 1H), 5.28 (br d, J=9.6 Hz, 1H), 4.46 (br s, 2H), 4.01 (br d, J=11.3 Hz, 1H), 3.55 (br d, J=9.8 Hz, 1H), 2.48-2.36 (m, 1H), 2.00-1.91 (m, 1H), 1.80 (br d, J=12.7 Hz, 1H), 1.65-1.48 (m, 3H), 1.43 (br s, 5H), 1.34 (br s, 4H), 1.07 (br t, J=6.9 Hz, 3H). UHPLC method conditions: Column: Supelco Ascentis Express C18, 2.7 μm, 2.1×50 mm; Mobile phase A: 0.01 M NH$_4$OAc in acetonitrile:water (5:95); Mobile phase B: 0.01 M NH$_4$OAc in acetonitrile:water (95:5); Temperature: 40° C.; Gradient: 0 min (0% B), 0.3 min (20% B), 2.5 min (20% B), 5 min (45% B), 6 min (100% B), 8 min (100% B); Flow: 1.0 mL/min; LC RT 5.74 min; LC/MS (ESI) Calcd for $[C_{26}H_{33}N_7O_3+H]^+$ 492.3. found 492.3.

Alternative procedure: to a 250 mL reactor purged and maintained with an inert atmosphere of nitrogen, was added methanol (30 mL), 2-methyl-tetrahydrofuran (90 mL), 2-chloro-5-(1-(tetrahydro-2H-pyran-2-yl)-1H-pyrazol-5-yl) aniline (16.21 g, 58.5 mmol, 1.1 equiv), potassium pivalate (11.92 g, 85.1 mmol, 1.6 equiv). MeOH (20 mL) was used as a rinse. Tetrahydroxydiboron (7.62 g, 85.1 mmol, 1.6 equiv) was charged followed by a MeOH rinse (20 mL). The resulting solution was degassed by a nitrogen sparge for 30 minutes at 20° C. To a 20 mL vial, was added 2-dicyclohexylphosphino-2',4',6'-triisopropylbiphenyl (XPhos) (253 mg, 0.532 mmol, 0.0100 equiv), allylpalladium chloride dimer (49.5 mg, 0.133 mmol, 0.0025 equiv), and 2-methyl-tetrahydrofuran (xx mL). The resulting solution was degassed by a nitrogen sparge for 30 minutes at 20° C. The catalyst solution was transferred under inert conditions from the 20 mL vial to the 250 mL reactor. The reaction was held at 20° C. for 4 hours. The reaction stream was cooled to 10° C., and degassed anhydrous NaOMe (25 wt %, 61 mL, 266 mmol, 5.0 equiv) was added under inert conditions over 15 minutes and the resulting mixture was held at 10° C. overnight. To the reactor was added tert-butyl ((4-cyano-5-iodo-1H-imidazol-2-yl)methyl)(ethyl)carbamate (20 g, 53.2 mmol, L.R.), (PCy$_2$tBu)$_2$PdCl$_2$ (366 mg, 0.532 mmol, 0.010 equiv), and 2-methyl-tetrahydrofuran (20 mL). The mixture was stirred at 60° C. for 12 hours, then cooled to 20° C. over 2 h. The stream was filtered and the residual on the filter was washed with 2-Me-THF (20 mL). The combined stream was transferred to a 250 mL chemglass reactor. Dichloroacetic acid (26.3 mL 41.1 g, 319 mmol, 6 equiv) was charged over 15 min and stream is agitated for 2.5 h. Dichloroacetic acid (26.3 mL 41.1 g, 319 mmol, 6 equiv) was charged over 15 min and stream is agitated for 9.0 h. The batch was then cooled to 20° C. over 2 hours. The solids were collected by filtration. The wash solution was prepared beforehand: 1:1 2-Me-THF and methanol was mixed and water was added until the solution water level determined by karl Fischer reached 20 wt %. The wet cake was washed with the wash solution (100 mL, 5.0 L/kg) twice. This resulted in 18.78 g (70% yield) of tert-butyl ((4-amino-7-(1H-pyrazol-5-yl)-1H-imidazo[4,5-c]quinolin-2-yl)methyl)(ethyl)carbamate dichloroacetic acid salt as an off-white solid.

Example 5: Preparation of 2-((ethylamino)methyl)-7-(1H-pyrazol-3-yl)-1H-imidazo[4,5-c]quinolin-4-amine Bis-Hydrochloride Salt

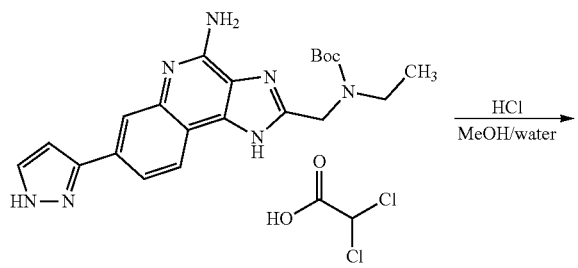

-continued

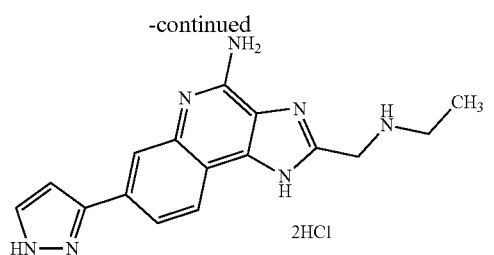

2HCl

To a 20-mL bottle were charged tert-butyl ((4-amino-7-(1H-pyrazol-3-yl)-1H-imidazo[4,5-c]quinolin-2-yl)methyl)(ethyl)carbamate 2,2-dichloroacetic acid salt (1 g, 1 equiv), MeOH (2.8 mL, 2.8 mL/g). The mixture was heated to 50° C. HCl (6N) (1.87 mL, 6 equiv) and water (3.12 mL, 3.12 mL/g) were mixed and then added to above mixture in portions over 90 min. Reaction mixture was aged at 50° C. overnight. The mixture was then cooled to 40° C. followed by seeding with 2-((ethylamino)methyl)-7-(1H-pyrazol-3-yl)-1H-imidazo[4,5-c]quinolin-4-amine bis-HCl salt (0.007 g, 0.01 equiv) and 30 min aging. MeOH (5.6 mL, 5.6 mL/g) was charged slowly and aged at 40° C. for additional 30 min. The slurry was cooled to 20° C. MTBE (9.6 mL, 9.6 ml/g) was charged to further de-saturate the mixture. The resulting slurry was filtrated. The wet cake was washed with a mixture of MeOH/MTBE (1/1) (3.0 mL, 3 mL/g), twice with MTBE (6.0 mL, 6.0 mL/g) and dried under vacuum at 50° C. overnight. 2-((Ethylamino)methyl)-7-(1H-pyrazol-3-yl)-1H-imidazo[4,5-c]quinolin-4-amine bis-HCl salt was obtained as a white solid (0.69 g, 98% yield). $^1$H NMR (400 MHz, DMSO-$d_6$) δ 13.97-13.77 (m, 1H), 9.69 (br s, 2H), 8.39-8.17 (m, 2H), 8.04 (dd, J=8.3, 1.5 Hz, 1H), 7.86 (d, J=2.3 Hz, 1H), 6.86 (d, J=2.3 Hz, 1H), 4.54 (br s, 2H), 3.24 (br d, J=4.3 Hz, 2H), 1.30 (t, J=7.2 Hz, 3H). UPLC/MS conditions: Column Ascentis Express C18 2.1×50 mm, 2.6 µm particles; Mobile Phase A: 0.05% TFA in CH$_3$CN:Water (5:95); Mobile Phase B: 0.05% TFA in Water: CH$_3$CN (5:95); Temperature: 40° C.; Gradient: 0-100% B over 2 min; stop time 2.5 min; Flow: 1.0 mL/min; LC RT: 0.81 min; LC/MS (ESI) Calcd for [C$_{16}$H$_{17}$N$_7$+H]$^+$ 308.2. Found 308.2.

Alternative conditions in IPA: to a 250-mL round bottom flask were charged tert-butyl ((4-amino-7-(1H-pyrazol-3-yl)-1H-imidazo[4,5-c]quinolin-2-yl)methyl)(ethyl)carbamate 2,2-dichloroacetic acid salt (10.0 g, 1 equiv), IPA (50 mL, 5.0 mL/g). HCl (2N) (8.7 mL, 1.0 equiv) was charged. The batch was heated to 60° C. and additional HCl (2N) (44 mL, 5.0 equiv) was charged over 2.5 h. The batch was agitated at 60° C. overnight. The batch is heated to 70° C. and IPA (50 mL, 5.0 L/kg) was charged. The batch was seeded with product (200 mg, 0.02 equiv), aged at 70° C. for 5 h and cooled to 20° C. over 6 h. The slurry was agitated at 20° C. overnight and filtered. The wet cake was washed with 2:1 IPA:water (50 mL, 5.0 L/kg) and IPA (50 mL, 5.0 L/kg). The cake was dried under vacuum at 50° C. overnight. 2-((Ethylamino)methyl)-7-(1H-pyrazol-3-yl)-1H-imidazo[4,5-c]quinolin-4-amine bis-HCl salt was obtained as a white solid (6.8 g, 97.9% yield).

Example 6: Preparation of N-((4-amino-7-(1H-pyrazol-3-yl)-1H-imidazo[4,5-c]quinolin-2-yl)methyl)-N-ethylacetamide (Compound 1)

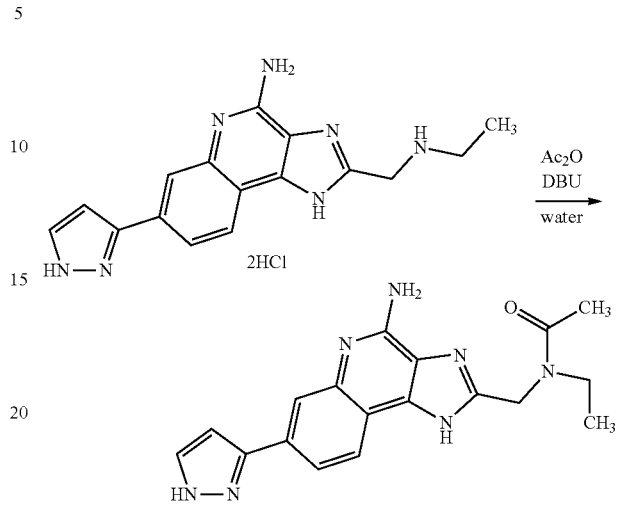

To a 10-L ChemGlass reactor 1 was charged water (4.54 L, 14 L/kg) and 2-((ethylamino)methyl)-7-(1H-pyrazol-3-yl)-1H-imidazo[4,5-c]quinolin-4-amine bis-HCl salt (0.324 kg). The solution was agitated for 15 min. NaOH (1N, 0.486 L, 1.5 L/kg) was charged to ensure range of pH 3-6. SiliaMeS Thiourea (0.081 kg, 0.25 kg/kg) was charged and solution was agitated for 16 h. The stream was polish filtered and transferred to the 10-L ChemGlass reactor 2. Water (1.944 L, 6.0 L/kg) was used to rinse through the reactor 1 and polish filter into reactor 2. 1,8-Diazabicyclo(5.4.0)undec-7-ene (0.389 kg, 1.2 kg/kg, 3 equiv) was charged to reactor 2 followed by charging acetic anhydride (0.096 kg, 0.296 kg/kg, 1.1 equiv) over 15 min at 25° C. The reaction mixture was agitated for 30 min. Additional 1,8-Diazabicyclo(5.4.0)undec-7-ene (0.194 kg, 0.6 kg/kg, 1.5 equiv) was charged to reactor 2. The reaction solution was heated to 60° C. and agitated for 3 h. The solution is seeded with N-((4-amino-7-(1H-pyrazol-3-yl)-1H-imidazo[4,5-c]quinolin-2-yl)methyl)-N-ethylacetamide (0.01 kg, 0.03 kg/kg) and aged for 60 min. Acetic acid (0.855 L, 1M, 2.64 L/kg, 1.0 equiv) was charged over 2 h. The resulting slurry was agitated for 1 h and cooled to 20° C. over 2 h. The slurry was filtered and the wet cake was washed with water (2×1.62 L, 2×5 L/kg) and acetone (1.62 L, 5 L/kg). The resulting wet cake was dried at 300 mbar and 30° C. for 2 hours using humidified nitrogen supply. N-((4-amino-7-(1H-pyrazol-3-yl)-1H-imidazo[4,5-c]quinolin-2-yl)methyl)-N-ethylacetamide was isolated as a white solid (0.232 kg, 91% yield), which was determined as Form A. $^1$H NMR (400 MHz, MeOH-$d_4$) δ 8.15-8.07 (m, 1H), 7.98 (s, 1H), 7.80-7.67 (m, 2H), 6.80-6.70 (m, 1H), 4.88-4.85 (m, 2H), 3.60-3.48 (m, 2H), 2.30-2.20 (m, 3H), 1.23 (t, J=7.2 Hz, 2H), 1.11 (t, J=7.2 Hz, 1H). UPLC/MS conditions: Column Ascentis Express C18 2.1×50 mm, 2.6 µm particles; Mobile Phase A: 0.05% TFA in MeOH:Water (20:80); Mobile Phase B: 0.05% TFA in MeOH:CH$_3$CN (20:80); Temperature: 40° C.; Gradient: 0-100% B over 2 min; stop time 2.5 min; Flow: 1.0 mL/min; LC RT: 0.84 min; LC/MS (ESI) Calcd for [C$_{16}$H$_{17}$N$_7$+H]$^+$ 350.1. Found 350.1.

Preparation described for Compound 112 in PCT/US2018/018484 also yielded the Form A of Compound A.

Form B of Compound 1 was obtained by dehydration of the Form A of Compound 1.

Alternative conditions using N-methylpyrrolidine and ethylenediamine in NMP: To a 250-mL ChemGlass reactor was charged 2-((ethylamino)methyl)-7-((1H-pyrazol-3-yl)-1H-imidazo[4,5-c]quinolin-4-amine bis-HCl salt (30 g) and N-methyl 2-pyrrolidinone (210 mL, 7 L/kg) followed by addition of N-methylpyrrolidine (22.4 g, 0.75 kg/kg, 3.5 equiv.) over 15 min. The system was aged for 18 h. Acetic anhydride (9.61 g, 0.320 kg/kg, 1.25 equiv.) was charged over 4h at 22° C. The reaction mixture was agitated for at least 4h to reach reaction completion. After reaction reached completion, water (30 g, 1 L/kg) was added to the reactor. The reaction was agitated for at least 30 min before charging ethylenediamine (13.6 g, 0.453 kg/kg, 3.0 equiv.). The reaction solution was agitated for 3h to completely convert over-acetylated impurities back to the main product. After impurity conversion an aqueous acetic acid solution (609 g, 1.5 wt %, 20.3 kg/kg, 2.0 equiv.) was added over 2h followed by seeding with N-((4-amino-7-(1H-pyrazol-3-yl)-1H-imidazo[4,5-c]quinolin-2-yl)methyl)-N-ethylacetamide (0.30 g, 0.01 kg/kg, 1.0 wt %) and aging the batch for at least 7 h at 25° C. The resulting slurry was filtered; the wet cake was washed with water (1×150 mL, 1×5 L/kg) once and acetone (2×150 mL, 2×5 L/kg) twice. The wet cake was then dried at 300 mbar and 30° C. for 2 hours using humidified nitrogen to supply N-((4-amino-7-(1H-pyrazol-3-yl)-1H-imidazo[4,5-c]quinolin-2-yl)methyl)-N-ethylacetamide as a white solid (25 g, 90% yield) which was determined as form A.

Alternative conditions using diisopropylethylamine and ethylenediamine in NMP: To a 100-mL ChemGlass reactor was charged 2-((ethylamino)methyl)-7-((1H-pyrazol-3-yl)-1H-imidazo[4,5-c]quinolin-4-amine bis-HCl salt (5 g) and N-methyl pyrrolidinone (40 mL, 8 L/kg) followed by addition of diisopropylethylamine (4.87 g, 0.973 kg/kg, 3.0 equiv.) over 15 min. and acetic anhydride (1.54 g, 0.307 kg/kg, 1.20 equiv.) over 4 h at 25° C. The reaction mixture was agitated for at least 4 h to reach reaction completion. After reaction reached completion, ethylenediamine (2.26 g, 0.453 kg/kg, 3.0 equiv.) and water (5 g, 1 L/kg) were added to the reactor. The reaction solution was agitated for 3h to completely convert over-acetylated impurities back to the product. After impurity conversion water (55 g, 11 L/kg) and acetic acid (1.51 g, 0.302 kg/kg, 2.0 equiv.) were mixed and added to the reaction stream over 1 h followed by seeding with N-((4-amino-7-(1H-pyrazol-3-yl)-1H-imidazo[4,5-c]quinolin-2-yl)methyl)-N-ethylacetamide (0.05 g, 0.01 kg/kg, 1.0 wt %) and aging the batch for at least 7 h at 25° C. The resulting slurry was filtered; the wet cake was washed with water (1×25 mL, 1×5 L/kg) once and acetone (2×25 mL, 2×5 L/kg) twice. The wet cake was then dried at 300 mbar and 30° C. for 2 hours using humidified nitrogen to supply N-((4-amino-7-(1H-pyrazol-3-yl)-1H-imidazo[4,5-c]quinolin-2-yl)methyl)-N-ethylacetamide as a white solid (4.2 g, 90% yield) which was determined as form A.

Example 7. Preparation of tert-butyl ((1H-imidazol-2-yl)methyl)(ethyl)carbamate

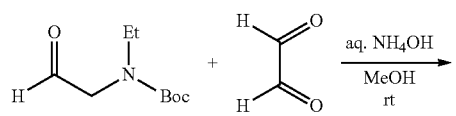

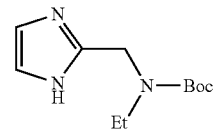

To a clear magnetically stirred mixture of 30 mL MeOH and 10 mL (148 mmol) NH$_4$OH were added 5.2 g (28 mmol) of neat tert-butyl ethyl(2-oxoethyl)carbamate. The resulting clear solution was cooled to 5° C. and 10 mL of 40% aq. glyoxal was added over 2 min. After glyoxal addition was complete the resulting clear yellowish reaction mixture was stirred at room temp for 18 h at which time it became a brownish thin slurry. The slurry was filtered and the solid was discarded. The filtrate was concentrated and the residue was partitioned between 50 mL water and 80 mL MTBE. The collected orange organic phase was concentrated to afford an orange oil weighing ca. 7 g. The crude product was flash chromatographed on a silica gel column eluting with a gradient of DCM/THF to afford 3.75 g (60% yield as-is) of the desired tert-butyl ((1H-imidazol-2-yl)methyl)(ethyl)carbamate as a beige solid: mp 90-91° C. $^1$H NMR (400 MHz, methanol-d4): δ 6.97 (s, 2H), 4.46 (s, 2H), 3.29 (brs, 2H), 1.46 (brs, 9H), 1.04 (brs, 3H). $^1$H NMR (400 MHz, DMSO-d$_6$) δ 11.79 (br s, 1H), 7.01 (br s, 1H), 6.91-6.73 (m, 1H), 4.35 (s, 2H), 3.25-3.12 (m, 2H), 1.40 (br s, 9H), 0.96 (t, J=7.1 Hz, 3H); UPLC/MS conditions: Column Ascentis Express C18 2.1×50 mm, 2.6 μm particles; Mobile Phase A: 0.05% TFA in CH$_3$CN:Water (5:95); Mobile Phase B: 0.05% TFA in Water: CH$_3$CN (5:95); Temperature: 40° C.; Gradient: 0-100% B over 2 min; stop time 2.5 min; Flow: 1.0 mL/min; LC RT: 0.837 min; LRMS (ESI) Calcd for [C$_{11}$H$_{19}$N$_3$O$_2$+H]$^+$ 226.1. Found 226.1.

Example 8. Preparation of tert-butyl ((4,5-diiodo-1H-imidazol-2-yl)methyl)(ethyl)carbamate

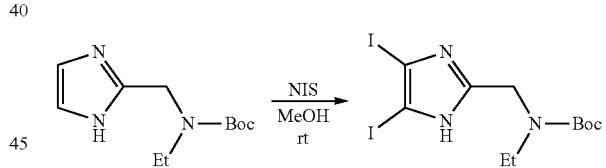

To a magnetically stirred clear cold solution of 1.35 g (6 mmol) tert-butyl ((1H-imidazol-2-yl)methyl)(ethyl)carbamate in 10 vol MeOH (14 mL) kept in a cooling bath (ice/water) were added at once 3 g (13.3 mmol) of NIS. The resulting reddish solution was stirred for 20 min at 0-4° C. and then 30 min at room temp by removing it from the cooling bath. The reaction mixture was concentrated and the residue was partitioned between 40 mL EtOAc and 20 mL of 10% w/w aq. NaHSO$_3$. The collected top light orange organic phase was concentrated to dryness and the residue was flash chromatographed over silica gel eluting with a gradient of EtOAc/DCM. The desired fractions were pooled and rotoevaporated to dryness. The residue was azeotroped with 100 mL of cyclohexane. There were obtained 2.2 g (77% yield as-is) of the desired tert-butyl ((4,5-diiodo-1H-imidazol-2-yl)methyl)(ethyl)carbamate as a white solid. $^1$H NMR (400 MHz, CDCl$_3$) δ 4.34 (s, 2H), 3.30 (q, J=7.1 Hz, 2H), 1.49 (s, 9H), 1.08 (t, J=7.1 Hz, 3H); UPLC/MS conditions: Column Ascentis Express C18 2.1×50 mm, 2.6 μm particles; Mobile Phase A: 0.05% TFA in CH$_3$CN:Water Example 9. Preparation of tert-butyl ((4-cyano-5-iodo-1H-imidazol-2-yl)methyl)(ethyl)carbamate

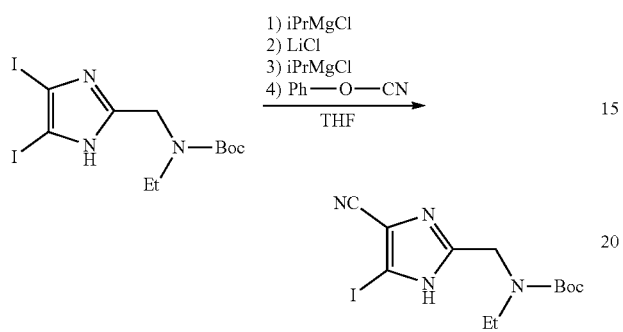

To a magnetically stirred yellowish solution of 960 mg (2 mmol) of tert-butyl ((4,5-diiodo-1H-imidazol-2-yl)methyl)(ethyl)carbamate in a 5 mL of anhydrous THF kept under $N_2$ at −20° C. (internal) were added 1.2 mL of 2M iPrMgCl/THF (2.4 mmol) with a syringe over 2 min. The resulting clear yellowish solution was stirred for 15 min at 0° C. in an ice/water bath. The clear yellowish solution was cooled down to −20° C. to −25° C. in an acetone/dry ice bath and 4 mL of 0.5M LiCl/THF were added in followed by 1.3 mL of 2M iPrMgCl/THF (2.6 mmol) with a syringe over 2 min. The resulting slightly brownish solution was stirred for 15 min at −20° C. to −25° C. and then at 0° C. for 10 min. The reaction mixture which was still a clear brownish solution at this point was cooled to −25° C. To this mixture was added 380 mg (3 mmol) of neat Ph-O—CN with syringe over 1 min. The resulting clear solution was stirred at −20° C. for 15 min, removed from the cooling bath and allowed to warm up to room temp. The resulting reddish solution was rotoevaporated and the residue was partitioned between 40 mL EtOAc and 20 mL 10% aq. citric acid. The collected top organic phase was flash chromatographed over silica gel eluting with gradient of EtOAc/DCM. Product rich fractions were pooled and rotoevaporated to dryness to afford 580 mg (77% as-is) of the desired tert-butyl ((4-cyano-5-iodo-1H-imidazol-2-yl)methyl)(ethyl)carbamate as a white solid. $^1$H NMR (400 MHz, CDCl$_3$): δ 10.75 (brs, 1H), 4.34 (s, 2H), 3.32 (q, 2H), 1.50 (m, 9H), 1.09 (t, J=8.0 Hz, 3H). The product's $^1$H NMR in CDCl3 was identical to $^1$H NMR of the one produced from step 2. UPLC/MS conditions: Column Ascentis Express C18 2.1×50 mm, 2.6 μm particles; Mobile Phase A: 0.05% TFA in CH$_3$CN:Water (5:95); Mobile Phase B: 0.05% TFA in Water: CH$_3$CN (5:95); Temperature: 40° C.; Gradient: 0-100% B over 2 min; stop time 2.5 min; Flow: 1.0 mL/min; LC RT: 1.311 min; LRMS (ESI) Calcd for $[C_{12}H_{18}IN_4O_2+H]^+$ 377.0. Found 377.0. The product's retention time was identical to the retention time of the one produced from step 2 on the given UPLC/MS method.

What is claimed is:

1. A compound having the following formula:

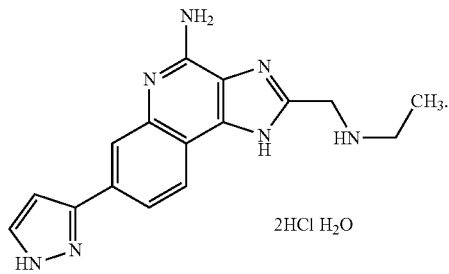 [SMILES: CCNCc1nc2c(N)nc3cc(-c4cc[nH]n4)ccc3c2[nH]1 ; "2HCl H2O"]

2HCl H$_2$O

2. A compound having the following formula:

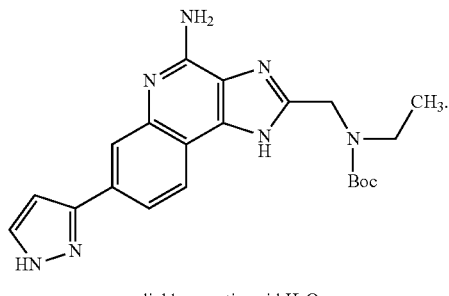

dichloroacetic acid H$_2$O

* * * * *